(12) United States Patent
Swartz et al.

(10) Patent No.: US 7,084,628 B2
(45) Date of Patent: Aug. 1, 2006

(54) METHODS AND APPARATUS FOR POST-EXPOSURE DETERMINATION OF IONIZING RADIATION DOSE

(75) Inventors: Harold M. Swartz, Lyme, NH (US); William F. B. Punchard, Sudbury, MA (US); Piotr M. Starewicz, Somerville, MA (US); Tadeusz M. Walczak, Hanover, NH (US)

(73) Assignees: Resonance Research Inc., Billerica, MA (US); Dartmouth University, Hanover, NH (US)

( * ) Notice: Subject to any disclaimer, the term of this patent is extended or adjusted under 35 U.S.C. 154(b) by 79 days.

(21) Appl. No.: 10/731,552

(22) Filed: Dec. 8, 2003

(65) Prior Publication Data

US 2004/0251899 A1    Dec. 16, 2004

Related U.S. Application Data

(60) Provisional application No. 60/432,177, filed on Dec. 9, 2002.

(51) Int. Cl.
*G01V 3/00* (2006.01)

(52) U.S. Cl. .................................. 324/316

(58) Field of Classification Search ............. 324/316, 324/300; 250/305

See application file for complete search history.

(56) References Cited

U.S. PATENT DOCUMENTS

| | | | |
|---|---|---|---|
| 5,233,303 A * | 8/1993 | Bales et al. | 324/316 |
| 5,494,030 A * | 2/1996 | Swartz et al. | 600/323 |
| 5,818,056 A * | 10/1998 | Pass | 250/458.1 |
| 6,791,324 B1 * | 9/2004 | Maier et al. | 324/316 |

OTHER PUBLICATIONS

Miyake M et al., "In vivo EPR dosimetry of accidental exposures to radiation: experimental results indicating the feasibility of practical use in human subjects", Appl Radiat Isot 52: pp. 1031-1038, (2000).*

Haskell EH et al., "Electron Paramagnetic Resonance Techniques and Space Biodosimetry", Radiat Res 148: pp. S51-S59, (1997).*

Oka T et al., "A High-sensitivity Portable Spectrometer for ESR Dosimetry", Appl Radiat Isot 47, No. 11/12: pp. 1589-1594, (1996).*

* cited by examiner

*Primary Examiner*—Diego Gutierrez
*Assistant Examiner*—Jeremiah Shipman
(74) *Attorney, Agent, or Firm*—David Prashker, Esq.

(57) ABSTRACT

The instant invention provides in-vivo methods and apparatus for radiation dosimetry assessment in individuals exposed to potentially harmful radiation, based on measurements in-situ of the teeth. The in vivo dosimetry assessment methods and apparatus utilize electron paramagnetic resonance (EPR) techniques; and employ an apparatus comprising an integrated EPR spectrometer system, an ergonomic magnet and a constructed resonator structure. In various aspects, the dosimetry assessment apparatus is configured to be easily portable and withstand potentially adverse mechanical effects of transportation and deployment in the field. The apparatus also is configured with a power supply that is compatible with both conventional AC line voltages and/or other sources of power suitable for field conditions; and may be easily operated by minimally trained technicians to quickly generate a readout of estimated radiation exposure dose.

22 Claims, 43 Drawing Sheets

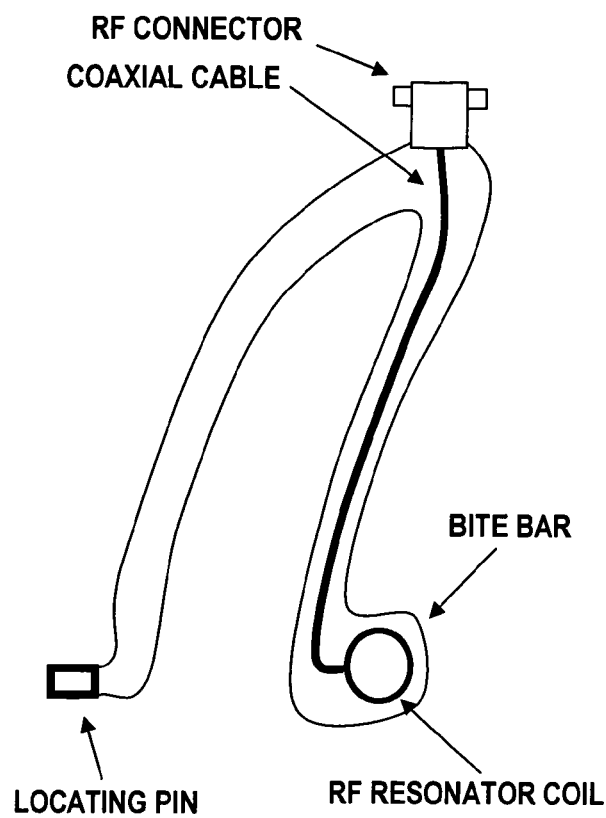
Fig. 6A          Fig. 6B
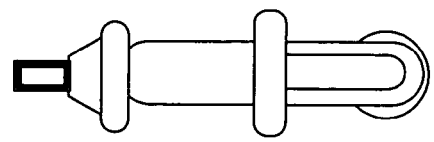
Fig. 6C

METHODS AND APPARATUS FOR POST-EXPOSURE DETERMINATION OF IONIZING RADIATION DOSE

PRIORITY FILING

The present invention was first filed as U.S. Provisional Patent Application Ser. No. 60/432,177 on Dec. 9, 2002.

FIELD OF THE INVENTION

The present invention relates generally to determining a person's exposure to potentially harmful ionizing radiation. More specifically, the invention is directed to methods and apparatus for conveniently and effectively measuring radiation exposure in vivo using electron paramagnetic resonance (EPR) techniques.

BACKGROUND OF THE INVENTION

In the post Cold War setting, a number of potential scenarios involving radiation exposure of humans is likely to result from a variety of diverse events—such as a limited nuclear exchange, a terrorist action using an improvised nuclear device, an accidental or intentional nuclear power plant release, or even a conventional explosive employed as a means for disseminating radioactive materials (Radiation Dispersal Device). In such scenarios, radioactive contamination may vary widely. Consequently, the exposure of individuals cannot be calculated and must be measured in the individual for an accurate assessment of risk.

Clearly, there are plausible circumstances in which specific populations potentially have been exposed to doses of ionizing radiation that could cause direct clinical effects within days or weeks, but where there is no clear knowledge as to the, magnitude of the exposure to individuals. Also, while it is likely that many of the exposed individuals will not have received clinically significant doses of radiation, others in the immediate vicinity may have been exposed to potentially life-threatening doses. It is therefore both appropriate and necessary to differentiate among persons and exposure doses sufficiently in order to classify individuals into subclasses for treatment and advice.

In addition, a rapid assessment of radiation doses received by victims is critical for accurate decision-making with respect to post-exposure treatment of exposure victims. It is generally appreciated that, for all but the highest exposure doses which cause prompt biological effects, a unique and challenging aspect of radiological injury is the delayed onset of clinical symptoms following exposure. In this regard, a common problem associated with relatively low to intermediate range exposure doses is that effective decisions regarding further action and/or treatment following victim exposure may be compromised by the lack of information and uncertainty of the dose quantity the victim received. For example, decisions concerning whether to evacuate an area or to return to duty may be difficult in the hours and days immediately following exposure if there is little or inadequate information regarding the ionizing radiation exposure dose.

In response to the need to plan for potential exposure of a large population to harmful radiation, minimal requirements have been established (e.g., by NATO and U.S. military) calling for accurate post-exposure radiation dose assessments for individuals exposed to radioactive contamination [see "Army Specific Military Requirements for Nuclear Weapons and Radiation Effects Information," FY01/02, 19 Jan. 2000: SMR 3.1.2a, priority 2, and draft NATO Standardization Agreement 2474 on recording of radiation doses for NATO forces, these documents being expressly incorporated by reference herein]. However, the conventional solutions proposed to date for assessing post-exposure doses have not resulted in generally practical and effective techniques.

The Conventional Approach for After-the-Fact Assessment of Radiation Exposure

Potentially, an after-the-fact assessment could be made from biological or physical changes. However, there are very few biological methods truly available for this purpose because of the immediate results of irradiation in-vivo. Even in high exposure dose instances, only a few persons exhibit biological manifestations. The one approach that has been widely used, the measurement of changes in the blood, is non-specific and time-consuming. After exposure, the number of circulating lymphocytes in the blood will decrease, but this manifestation cannot be used to provide a quantitative estimate of exposure dose. Also, certain changes in the chromosomes can be assessed, but this alternative procedure is time-consuming, is technically difficult, and is at best semi-quantitative.

There is one traditional method based on physical changes which is conventionally known and used for assessing radiation exposure. It involves electron paramagnetic resonance (or "EPR") spectroscopy techniques [which are also known as electron spin resonance ("ESR")] to assess exposure to ionizing radiation. These techniques measure long-lasting changes in a victim's hard tissues (e.g., teeth and bones) that result from radiation exposure.

Ionizing radiation generates large numbers of unpaired electron species. While most of these react immediately and disappear, in some materials in which diffusion is limited, the unpaired electrons can persist for long periods of time [Brady, J. M., Norman O. Aarestad and Harold M. Swartz (1968), "In Vivo dosimetry by electron spin resonance spectroscopy," Health Physics, 15:43–47]. This phenomenon has been recognized to occur in bone and teeth for more than 50 years. It was shown to be a feasible method for retrospective dosimetry and subsequently has been used widely for dosimetry in isolated teeth and bones. Teeth are especially attractive because the signal intensity is stronger in them, because of the higher amount of enamel.

Conventional EPR techniques are based on isolated teeth and bones. They require the use of high magnetic field, and therefore employ large magnets and bulky supporting equipment which are suitable only for in-vitro laboratory evaluation. Typically, the EPR technique uses a magnetic field to establish different energy levels for unpaired electrons in hard tissue, which are the result of radiation exposure and which therefore have a net magnetic moment because of electron spin. A radio-frequency (i.e., microwave) electromagnetic field then is applied to the previously exposed hard tissues via a resonator structure to obtain electron transitions between the different energy levels, as established by the magnetic field. A radiation dose then may be estimated based on the received signal intensity. Modulation of the magnetic field additionally may be employed to enhance the sensitivity of electron energy measurements.

Most dosimetry studies based on teeth and reported in the scientific literature have been carried out at conventional EPR frequencies (e.g., 9 GHz) for higher sensitivity and under conditions where some removal of aqueous components is possible [See for example, Harold M. Swartz, Robert P. Molenda and Robert T. Lofberg (1968), "Long-lived radiation-induced electron spin resonances in an aqueous biological system," Biochem. Biophysical Research Communications, 21:61–65]. Using this approach, it has been possible to measure doses in the range of centiGray (cGy) values in isolated teeth. While such data are useful for many purposes, this approach cannot meet in-vivo needs, because it usually would not be feasible to remove teeth from the population to be screened.

Many conventionally known EPR spectroscopy techniques used in connection with an assessment of radiation exposure are evaluated and discussed in detail within the scientific literature. Some representative publications include the following, each of which is expressly incorporated herein by reference: Harold M. Swartz, Robert P. Molenda and Robert T. Lofberg (1968), "Long-lived radiation-induced electron spin resonances in an aqueous biological system," Biochem. Biophysical Research Communications, 21:61–65; Brady, J. M., Norman O. Aarestad and Harold M. Swartz (1968), "In Vivo dosimetry by electron spin resonance spectroscopy," Health Physics, 15:43–47; Ikeya M. and Ishii H. (1989), "Atomic bomb and accident dosimetry with ESR: Natural rocks and human tooth in-vivo spectrometer," Appl. Radiat. Isotop.m 40:1021–1027; M. Miyake, K. J. Liu, T. Walczak, and H. M. Swartz, "In Vivo EPR Dosimetry of Accidental Exposures to Radiation: Experimental Results Indicating the Feasibility of Practical Use in Human Subjects," Appl. Rad. & Isotopes 52:1031–1038 (2000); Yamanaka C., Ikeya M. and Hara H. (1993), "ESR cavities for in vivo dosimetry of tooth enamel," Appl. Radiat. Isotope., 44: 77–80; Ikeya M. and Miki T. (1980), "Electron spin resonance dating of animal and human bones," Science, 207: 977–979; Polyakov V. Haskell E., Kenner G., Huett G., and Hayes R. (1995), "Effect of mechanically induced background signal on EPR on dosimetry of tooth enamel," Radiat. Measure., 24: 249–254; Pass B. and Aldrich J. E. (1985), "Dental enamel as an in vivo radiation dosimeter," Med. Phys. 12:305–307; Hoshi M., Sawada S., Ikeya M. and Miki T. (1985), "ESR dosimetry for A-bomb survivors," ESR dating and Dosimetry, 407–414 Ionics, Tokyo; Ishii H., Ikeya M. and Okano S. (1990), "ESR dosimetry of teeth of residents close to the Chernobyl reactor accident," J. Nucl. Sci. Tech. 27:1153–1155; and Romanyukha A. A., Regulla D., Vasilenko E. and Wieser A., (1994), "South Ural nuclear workers: Comparison of individual doses from retrospective EPR dosimetry personal monitoring," Appl. Radiat. Isot., 45:1195–1199.

It will be noted and recognized that among the publications cited above are some which employ the term "in-vivo" in their title or content; however, none of these report results in which the empirical measurements were made in-vivo using living human subjects. The true informational value of these printed publications must therefore be very carefully and critically considered.

In addition, oxygen monitoring—a related EPR technology—is described in the patent literature. This is illustrated by the apparatus and methodology for determining oxygen in biological systems disclosed by U.S. Pat. Nos. 5,833,601 and 5,494,000 respectively.

Also, a number of scientific publications describe magnetic design methods in a variety of forms. These scientific publications are represented by: Hawksworth, D., New Magnet Design for MR, Mag. Res. in Medicine 17, 27–32 (1991). For magnetic design see also: Montgomery, D. B., Solenoid Magnet Design, Krieger Publishing Co. Inc, Huntingdon, N.Y. 1980.

In addition, a number of publications are directed to methods of constrained or non-constrained optimization without any direct mention of magnets as such. These include: Brent, R. P., Algorithms for Minimization without Derivatives, Prentice-Hall, Englewood, N.J.; Bertsekis, D. P., 1982, Constrained Optimization and Lagrange Multiplier Methods, Academic Press; and Powell, M. J. D., 1964, An efficient Method for Finding the Minimum of a Function of Several Variables without Calculating Derivatives, Comp. J., 7, 155–162 (1964).

Lastly, the patent literature provides a variety of useful magnet assemblies. These are merely illustrated by U.S. Pat. Nos. 4,701,736; 4,985,679; and 6,208,142 respectively.

Accordingly, for purposes of an easier understanding and a better appreciation of the present invention, the text of each individual scientific publication and each issued U.S. patent identified above is expressly incorporated by reference herein.

Present Obstacles and Challenges

A number of substantive technical obstacles and major scientific challenges presently stand in the way of meaningful improvements and effective advances in this field in order to make sensitive and accurate measurements in-vivo in humans. Among the long-standing and well recognized problems are the following.

The conventionally known EPR spectrometer is a bulky, stationary apparatus which is useful only in the analytical laboratory environment and requires careful operation by highly skilled technicians. Among the EPR spectrometer adopted for in-vitro analyses of hard human tissues such as teeth, none of them is portable or transportable and none of them can be operated by minimally trained individuals.

The usual size and weight of a conventional magnet makes it difficult to meet the logistical requirements for rapid measurements and transportability. Also, the power requirements for the conventional, higher field, magnet typically make the idea of a portable magnet nearly impossible.

The resonator is another technical challenge, because of the irregular shape of the teeth. The EPR signal is located principally in the enamel of the teeth, so the optimization of the sensitive volume of the resonator includes probing the maximum amount of enamel. Typically, a good sampling of the enamel requires the testing of one to several teeth.

A fourth area of technical challenge is the need to optimize a weak signal, which includes eliminating the overlapping background signal. With isolated teeth, the in-vitro dose-response for the tooth in question can be determined with the use of added known doses, with extrapolation back to the original dose. This option, of course, cannot be used with teeth in vivo.

Clearly therefore, the development of a portable apparatus and methods able to detect and accurately measure post-exposure doses of ionizing radiation in the teeth of living subjects is viewed as an unforeseeable and unpredictable event by persons technically skilled in this field. Equally important, were such a portable apparatus and detection method brought into functional existence on a practical use basis, such a development would be recognized as being a major advance of unusual benefit and value. Such after-the-fact measurements could also then be utilized for quality control of therapeutic radiation treatments.

SUMMARY OF THE INVENTION

The present invention has multiple aspects. A first aspect provides a dosimetry assessment apparatus for determining the degree of exposure of a living subject to ionizing radiation, wherein said living subject has been previously exposed to an unknown but potentially harmful dose of ionizing radiation, said dosimetry assessment apparatus comprising:

a detection assembly able to target at least one chosen tooth in the mouth of a living subject and generate a test EPR spectrum from the targeted tooth, said assembly including
- (i) a magnetic field generator of predetermined structure, dimensions and configuration and whose capacities and operating parameters are controlled to generate a stable and substantially uniform magnetic field strength of about 10 to 100 mT with a magnetic field uniformity of about 0.25% and a selected magnetic modulation field of about +/−0.1 to 0.5 mT with a magnetic field uniformity of about +/−10% over the region of interest,
- (ii) a resonator construct of predetermined dimensions and configuration which is adapted for engagement with at least one chosen tooth in the mouth of the living subject and whose operation allows for the emission of a radiowave of appropriate frequency for EPR measurement which is applied on-demand through the substance of the chosen tooth, and
- (iii) an electron paramagnetic resonance (EPR) spectrometer which is integrated with said magnetic field generator and whose operation generates a test EPR spectrum which can show the presence and absence of a net magnetic moment within said substantially uniform magnetic field occurring in response to a radiowave of appropriate frequency being applied to the chosen tooth in the mouth of the living subject;

electronic detection equipment able to detect the presence and absence of a net magnetic moment within a test EPR spectrum;

electronic operating controls coupled to said detection assembly; and a power supply integrated within said detection assembly.

A second aspect of the invention provides a dosimetry assessment system for determining the degree of exposure of a living subject to ionizing radiation, said dosimetry assessment system comprising:

a basis for identifying at least one living subject suspected of having been previously exposed to an unknown but potentially harmful dose of ionizing radiation;

a dosimetry apparatus for measuring exposure to ionizing radiation in a living subject, said apparatus comprising a detection assembly able to target at least one chosen tooth in the mouth of a living subject, said assembly including
- (i) a magnetic field generator of predetermined structure, dimensions and configuration and whose capacities and operating parameters are controlled to generate a stable and substantially uniform magnetic field strength of about 10 to 100 mT with a magnetic field uniformity of about 0.25% and a selected magnetic modulation field of about +/−0.1 to 0.5 mT with a magnetic field uniformity of about +/−10% over the region of interest,
- (ii) a resonator construct of predetermined dimensions and configuration which is adapted for engagement with at least one chosen tooth in the mouth of the living subject and whose operation allows for the emission of a radiowave of appriorate frequency for EPR measurement which is applied on-demand through the substance of the chosen tooth,
- (iii) an electron paramagnetic resonance (EPR) spectrometer which is integrated with said magnetic field generator and whose operation generates a test EPR spectrum which can show the presence and absence of a net magnetic moment within said substantially uniform magnetic field occurring in response to a radiowave of appropriate frequency being applied to the chosen tooth in the mouth of the living subject,
- (iv) electronic operating controls coupled to said detection assembly, and
- (v) a power supply integrated within said detection assembly;

a library of EPR spectra for teeth before and after exposure to known doses of ionizing radiation;

comparison means for comparing a test EPR spectrum with said library of EPR spectra; and readable output equipment showing an exposure dose of ionizing radiation based on a comparison of test and library EPR spectra.

A third aspect of the invention is a dosimetry assessment method for determining the degree of exposure of a living subject to ionizing radiation, said dosimetry assessment method comprising the steps of:

identifying at least one living subject who is suspected of having been previously exposed to an unknown but potentially harmful dose of ionizing radiation;

obtaining a dosimetry apparatus for measuring exposure to ionizing radiation in a living subject, said apparatus being suitable for the targeting of at least one chosen tooth in the mouth of a living subject and comprising
- (i) a magnetic field generator of predetermined structure, dimensions and configuration and whose capacities and operating parameters are controlled to generate a stable and substantially uniform magnetic field strength of about 10 to 100 mT with a magnetic field uniformity of about 0.25% and a selected magnetic modulation field of about +/−0.1 to 0.5 mT with a magnetic field uniformity of about +/−10% over the region of interest,
- (ii) a resonator construct of predetermined dimensions and configuration which is adapted for engagement with at least one chosen tooth in the mouth of the living subject and whose operation allows for the emission of a radiowave of appropriate frequency for EPR measurement which is applied on-demand through the substance of the chosen tooth,
- (iii) an electron paramagnetic resonance (EPR) spectrometer which is integrated with said magnetic field generator and whose operation generates a test EPR spectrum which can show the presence and absence of a net magnetic moment within said substantially uniform magnetic field occurring in response to a radiowave of approriate frequency being applied to the chosen tooth in the mouth of the living subject,
- (iv) electronic equipment able to detect the presence and absence of a net magnetic moment within a test EPR spectrum,
- (v) electronic operating controls, and
- (vi) an integrated power supply;

targeting said dosimetry apparatus to at least one chosen tooth within the mouth of a living subject;

operating said dosimetry apparatus to obtain a test EPR spectrum from said targeted tooth within the mouth of a living subject, said test EPR spectrum showing the presence or absence of a net magnetic moment within said substantially uniform magnetic field; and detecting the presence or absence of a net magnetic moment of within said test EPR spectrum, wherein the presence of a net magnetic moment in said test EPR spectrum is a measure of the subject's previous exposure to ionizing radiation.

A fourth aspect of the invention provides a comparative dosimetry assessment method for determining the degree of exposure of a living subject to ionizing radiation, said comparative dosimetry assessment method comprising the steps of:

identifying at least one living subject who is suspected of having been previously exposed to an unknown but potentially harmful dose of ionizing radiation;

obtaining a dosimetry apparatus for measuring exposure to ionizing radiation in a living subject, said apparatus being suitable for the targeting at least one chosen tooth in the mouth of a living subject and comprising (i) a magnetic field generator of predetermined structure, dimensions and configuration and whose capacities and operating parameters are controlled to generate a stable and substantially uniform magnetic field strength of about 10 to 100 mT with a magnetic field uniformity of about 0.25% and a selected magnetic modulation field of about +/−0.1 to 0.5 mT with a magnetic field uniformity of about +/−10% over the region of interest, (ii) a resonator construct of predetermined dimensions and configuration which is adapted for engagement with at least one chosen tooth in the mouth of the living subject, whose operation allows for the emission of a radiowave of appropriate frequency for EPR measurement which is applied on-demand through the substance of the chosen tooth, (iii), an electron paramagnetic resonance (EPR) spectrometer which is integrated with said magnetic field generator and whose operation generates a test EPR spectrum which can show the presence and absence of a net magnetic moment within said substantially uniform magnetic field occurring in response to a radiowave of appropriate frequency being applied to the chosen tooth in the mouth of the living subject, (iv) electronic operating controls, (v) an integrated power supply, (vi) a reference data library comprising the EPR spectra of specimen teeth obtained before and after exposure to known doses of ionizing radiation; and (vii) comparison equipment for comparing a test EPR spectrum with said reference data library of EPR spectra;

targeting said dosimetry apparatus to at least one chosen tooth within the mouth of a living subject;

operating said dosimetry apparatus to obtain a test EPR spectrum from said targeted tooth within the mouth of a living subject; and comparing said test EPR spectrum with said reference data library of EPR spectra to detect the presence or absence of a net magnetic moment within said test EPR spectrum, wherein said comparison of EPR spectra provides a measure of the subject's previous exposure to ionizing radiation.

A fifth aspect of the invention offers a comparative dosimetry assessment method for determining the degree of exposure of a living subject to ionizing radiation, said comparative dosimetry assessment method comprising the steps of:

identifying at least one living subject who is suspected of having been previously exposed to an unknown but potentially harmful dose of ionizing radiation;

obtaining a dosimetry apparatus for measuring exposure to ionizing radiation in a living subject, said apparatus being suitable for the targeting of at least one chosen tooth in the mouth of a living subject and comprising (i) a magnetic field generator of predetermined structure, dimensions and configuration and whose capacities and operating parameters are controlled to generate a stable and substantially uniform magnetic field strength of about 10 to 100 mT with a magnetic field uniformity of about 0.25% and a selected magnetic modulation field of about +/−0.1 to 0.5 mT with a magnetic field uniformity of about +/−10% over the region of interest, (ii) a resonator construct of predetermined dimensions and configuration which is adapted for engagement with at least one chosen tooth in the mouth of the living subject, whose operation allows for the emission of a radiowave of appropriate frequency for EPR measurement which is applied on-demand through the substance of the chosen tooth, (iii) an electron paramagnetic resonance (EPR) spectrometer which is integrated with said magnetic field generator and whose operation generates a test EPR spectrum which can show the presence and absence of a net magnetic moment within said substantially uniform magnetic field occurring in response to a radiowave of appropriate frequency being applied to said chosen tooth in the mouth of the living subject, (iv) electronic operating controls, (v) an integrated power supply, (vi) a mathematical model library comprising predicted EPR spectra of teeth before and after exposure to known doses of ionizing radiation; and (vii) comparison equipment for comparing a test EPR spectrum with said mathematical model library of predicted EPR spectra;

targeting said dosimetry apparatus to at least one chosen tooth within the mouth of a living subject;

operating said dosimetry apparatus to obtain a test EPR spectrum from said targeted tooth within the mouth of a living subject; and comparing said test EPR spectrum with said mathematical model library of predicted EPR spectra to detect the presence or absence of a net magnetic moment within said test EPR spectrum, wherein said comparison of EPR spectra provides a measure of the subject's previous exposure to ionizing radiation.

It will be recognized and appreciated that the apparatus and method comprising the present invention uses an EPR spectrometer tuned to lower radiowave frequencies (0.3 to 3.0 GHz instead of the usual 9.0 GHz), which can accommodate a large object; and equally important, does not cause unacceptable heating due to non-resonant absorption of the microwave. A resonator construct has been specially designed that can engage teeth in situ within the mouth, thereby maximizing the amount of enamel that is targeted and probed since most of the radiation-induced EPR signal is in the enamel.

Also, to permit rapid and comfortable positioning of the subject, the invention offers an asymmetric magnet system that can comfortably and effectively provide the required magnetic field in the teeth in the human head. Special data gathering and data processing procedures have been developed to maximize sensitivity and provide an output usable by modestly trained personnel.

Lastly, the challenges for the data gathering/processing aspects include the relatively low sensitivity of lower frequency EPR and the presence of a small but significant background signal in unirradiated teeth. The components of the system have been designed to make it reasonably transportable by cart, with the total system weighing about 80 kg.

BRIEF DESCRIPTION OF THE DRAWING

The present invention may be more easily understood and better appreciated when taken in conjunction with the accompanying drawing, in which:

FIGS. 6A–6C respectively are illustrations of a disposable plastic probe holder with RF connection;

DETAILED DESCRIPTION OF THE INVENTION

Figure 1A:
FIGS. 1A–1C respectively are illustrations of a preferred disk-shaped magnet.

The present invention recognizes the critical need for in-vivo radiation dosimetry assessment methods as well as the concomitant requirement for a transportable apparatus that may be employed in the field quickly, easily and effectively following a potentially harmful radiation exposure incident. Accordingly, the various embodiments of the present invention are directed to in-vivo dosimetry and ionizing radiation assessment methods; and provide an apparatus that may be readily deployed—if and when necessary—in a portable/mobile form for use in field operations for the making of radiation exposure dose estimates and for post-exposure clinical decision making for the living individuals on-site.

It will be noted and appreciated that the present invention provides and employs a magnet with a region of sufficient homogeneity that is located appropriately in the mouth when the subject's head rests against the surface of the magnet. The preferred weight of the magnet and its power supply is about 80–100 kg, which is within the range of reasonable transportability on a cart, and enables the instrument to be brought to the site of the population that needs to be screened. The modest power requirements for the magnet and the spectrometer can be met by batteries.

Also, a suitable and transportable EPR spectrometer has been constructed and tested with human subjects who have received therapeutic radiation that resulted in significant dose to the teeth. The response of a large number of teeth provide a norm that can be used to estimate the dose directly. The output will be in the form of a specific dose with a specific estimate of the uncertainty. The accuracy is enhanced by making sequential or concurrent measurements at three sites within the mouth.

Lastly, the resonator of the apparatus can be prepared in multiple embodiments. Any of them is suitable and useful for direct engagement of one or more teeth in the mouth of the living subject. Thus, in its current state, the instrument can provide estimates of absorbed dose of ±25 cGy in the range of 100 to >1,000 cGy. This currently given range will be yet improved, with further improvements in the resonator, the algorithm for calculating dose, and the uniformity of the magnetic field. In its current state of development, this range is sufficient for most applications related to terrorism or nuclear warfare.

I. The Basis of Applicants' Invention

Applicants' invention and approach to solving the problem of how to determine the degree and quantum of ionizing radiation dose exposure in-vivo and for a single living subject relies upon the following:

1. The invention relies on the use and determination of electron paramagnetic resonance (EPR), otherwise known as electron spin resonance (ESR). Detection techniques such as EPR specifically and sensitively respond to the presence of unpaired electrons in living tissues.

2. Ionizing radiation is known to generate large numbers of unpaired electron species. While most of these unpaired species react immediately and quickly disappear, for some living tissues in which diffusion is limited, the unpaired electron species can persist for long time periods. This unpaired electron species phenomenon has been recognized to occur in-vitro in extracted bone and teeth for more than 50 years and has been shown to be a feasible method for retrospective dosimetry in isolated teeth. Teeth are an especially attractive target material because the signal intensity is stronger in them than in other tissues, and because of the higher amount of crystalline matrix present in tooth enamel.

3. With the recent development of lower frequency EPR (e.g., 1 GHz) for making measurements in vivo with good detection sensitivity, it has now become possible for the first time to assess the amount of irradiated dose absorbed in vivo. The lower frequency EPR measurement has greater tolerance for the presence of water in-vivo and also has the benefit of being able to be targeted at a relatively large sample volume. The feasibility of this approach has been shown in animals; and its potential for use in human subjects was demonstrated by making measurements in isolated human teeth and comparing these measurements with isolated rat teeth and with rat teeth measured in situ in vivo.

4. The present invention provides both methods and specialized apparatus for making post-exposure determinations of ionizing radiation in-vivo. The apparatus disclosed herein provides an in-vivo EPR dosimeter designed specifically for measuring the radiation dose in teeth in situ in the human mouth. The general approach of this technique and some of the technically challenging aspects of the development are: it uses a lower frequency EPR spectrometer (1.2 GHz), a specially designed resonator that will probe teeth in-situ in the mouth; it provides a magnet system that can comfortably and effectively applied to the human head; it includes data processing to maximize sensitivity and yields an output usable by modestly trained personnel; and it offers an instrumentation that is suitable for use at the site of the potential exposures.

5. The present invention provides apparatus and a method which will yield retrospective dose information for individuals which is sufficiently accurate and reliable to discriminate rapidly among the following criteria:

(a) In-vivo exposures that are very unlikely to cause any acute symptoms (<50 cGy);

(b) In-vivo exposures that are likely to lead to mild and delayed clinical symptomatology (75–150 cGy);

(c) In-vivo exposures that are likely to lead to moderate to severe clinical symptomatology (150–300 cGy);

(d.) In-vivo exposures that are likely to lead to early severe clinical symptomatology with a potential for lethal outcome (>300 cGy); and (e) In-vivo exposures that are very likely to lead to early death (>600 cGy).

6. Applicants' methods and apparatus also provide multiple benefits and major advantages. These include, but are not limited to:

(i) being relatively easy to implement/operate by personnel without extensive training and with minimal technical experience;

(ii) providing dose measurements in a format that can be used immediately by those typically responsible for medical emergencies and without specific training in radiation effects;

(iii) being ergonomically designed for patient comfort and high throughput;

(iv) requiring little maintenance and calibration despite being portable;

(v) being easy to transport and deploy in the field owing to a manageable weight and size for the apparatus as a whole.

(vi) being capable of measuring radiation-induced EPR signals in teeth within the human mouth at doses of clinical relevance (i.e., at doses that would lead to proximate clinical symptoms);

(vii) being capable of making the measurements quickly so that large numbers of people can be screened rapidly;

(viii) providing the measurements in a format that can be used immediately by typical personnel with responsibility for medical emergencies and without specific training in radiation effects.

II. Applicants' Invention as a Whole

The subject matter as a whole comprising the present invention can take physical form in a number of different embodiments and alternative formats. For these reasons, a range and variety of illustrative and exemplary embodiments for the invention are disclosed.

In one embodiment, the in vivo dosimetry assessment methods and apparatus utilizing EPR techniques employ an integrated EPR spectrometer, an ergonomically designed magnet, and a plurality of different resonator designs that facilitate ease and effectiveness of use. A dosimetry assessment apparatus according to this embodiment is configured to be easily transportable and withstand potentially adverse mechanical effects of transportation and deployment in the field. The apparatus also may be configured with a power supply that is compatible with both conventional AC line voltages and/or other sources of power (e.g., batteries) that are suitable for field conditions.

In another embodiment, the methods and apparatus according to the present invention are configured to be capable of measuring clinically significant doses of radiation in teeth after a victim has been exposed, based on EPR measurement. In this embodiment, doses capable of being measured range from less than approximately 50 centi-Gray (cGy) to well beyond 20 Gray (Gy). This is a significantly broad range of radiation which includes doses that are very unlikely to cause any acute clinical effects through those exposure doses expected to result in death for the person within hours.

Thus, as noted above, the essential elements of in-vivo EPR dosimetry assessment include: generation of a magnetic field of controlled operating parameters to establish different energy levels for unpaired electrons in the tissue to be analyzed; applying a RF/microwave electromagnetic field to obtain transitions between the energy levels established by the magnetic field; and measuring the energy transitions of unpaired electrons in the living tissue to assess the quantity of radiation dose. These capabilities may be provided by a unique magnet, an in-vivo adapted resonator structure, and a carefully calibrated EPR spectrometer respectively. In all embodiments of the present invention, each of these elements and components is essential for the methods and apparatus that provide quick, easy and effective dosimetry assessments in-vivo. For these reasons also, each of these essential elements and components will be described in detail hereinafter.

II. Essential Components of the Invention

The present inventions comprises three essential components, each of which can be prepared in multiple configurations and dimensions, in alternative embodiments and formats, and in a range of different operating parameters and capacities.

A. The Magnetic Field Generator

The first essential component part of the apparatus to perform in-vivo dosimetry assessments for an particular living subject is the magnetic field generator. The preferred embodiments of the magnet will present certain operating capacities and provide particular operating parameters.

The Magnet System

The preferred embodiments of the invention include a purpose-designed magnet to be used in a specific application of measuring the ionizing radiation exposure of personnel through EPR spectroscopy of human teeth in vivo. A concave, curved, disc-shaped, or asymmetrically configured magnet can encompass the human jaw and reduce the size and weight of the dosimetry system, making the system portable and mobile in field scenarios.

A preferred magnet design contains the following characteristics and properties:

(a) The magnet has predetermined dimensions and a fixed configuration; and produces a homogeneous region of field, remote from the surface of the device when located adjacent to the head of the subject.

(b) The magnet structure is relatively small in size and is convenient to use with potential for large throughput and ease of transport.

(c) One preferred embodiment of the magnet is disk-shaped, with an approximate diameter of 20 to 40 cm, and has a flat surface on one side for patient accessibility. The patient oriented side of the magnet has a durable surface that is easy to clean and disinfect. The magnet is supported from the opposite side which is heat-sunk.

(d) The electronic control system and power supplies are built into the base of the unit. The power required to energize the magnet and the electronic control system (and any other any component of the invention) can be obtained alternatively from a battery, or from capacitors, or from a fuel cell, or by solar power.

(e) The magnet also contains an integrated assembly for field sweep with the range of +/−1 mT (10 Gauss), field modulation of +/−0.1 to 0.5 mT (1 to 5 Gauss), and field control and temperature monitoring.

For the ease of converting these SI magnetic field units into cgs magnetic field units, please take note of the following:

1.0 Gauss=0.0001 Tesla (T) or 0.1 mT
    10 Gauss=0.001 Tesla (T) or 1.0 mT
    100 Gauss=0.01 Tesla (T) or 10.0 mT
    1,000 Gauss=0.1 Tesla (T) or 100 mT
    10,000 Gauss=1.0 Tesla (T) or 1,000 mT The preferred magnet system, including the size and configuration of the magnet and its ability to provide effective and rapid access for the human head, is based on the use of a disc-shaped magnet system with a remote region of appropriate field uniformity located at the teeth that are being measured. The magnet system will provide a positioning device (locating hole with a latch and a bite-bar) with removable fixture for precise alignment of the jaw of the person being evaluated with respect to the uniform volume of the magnetic field.

Magnet Field Strength and Uniformity

The direction of the magnetic flux lines preferably will be perpendicular to the plane of the magnet. The field of view, (FOV), will be a spherical volume of diameter 15 to 20 mm, whose center will be located about 20 mm from the surface of the magnet. The field strength at the center of the FOV will be 40 mT, (400 Gauss), and the field uniformity over its volume will be 0.1 mT, (1 Gauss), peak-to-peak, i.e. 0.25%.

Field Modulation

To achieve the magnetic field modulation of the dosimeter appropriate for the operation at 0.1 to 0.5 mT (or +/−1 to 5 Gauss), the following is utilized:

(i) The incorporation of capabilities for variable modulation frequencies, so that the modulation frequency that minimizes microphonics can be chosen for the particular resonator and conditions (in contrast to the usual situation in which only a single modulation frequency is available for the EPR measurements).

(ii) Modulation coils designed and constructed to fit the requirements for providing effective magnetic field modulation within the human mouth with field uniformity of +/−10%.

(iii) The implementation of a transportable configuration having (a) a system with overall weight of 100 kg (220 lbs) or less, so that it can be readily transported; and
    (b) power requirements that can be met by batteries.

ILLUATRATIVE AND EXAMPLARY EMBODIMENTS

In the simplest use context, the magnet field generator is composed and formed of at least one, and sometimes two or more, kinds of magnetic materials—whose intrinsic properties cause or result in the establishment of a discernible magnetic flux density over a known area or volume by means of ferromagnetism. Such conventionally known intrinsic magnetic matter includes iron, steel, nickel, cobalt and various rare earth alloys.

In a more preferred context, the magnetic field generator is a purposefully designed construction of an electromagnet capable of generating magnetic flux densities of specified strengths and operating parameters. A number of different electromagnetic designs and constructs are available.

One preferred embodiment of a magnet is configured such that its coaxial coils are positioned asymmetrically across the plane perpendicular to the z-axis that runs through the center of the homogeneous field region. This particular magnet design enables a reduction in the overall size and weight of a dosimetry assessment system according to the present invention, allowing the system to be suitable for a variety of field scenarios.

Preferably, the magnet is designed as a substantially asymmetrical circular device that is configured in the round to produce an essentially homogenous field, remote from the surface of the magnet and located adjacent the head of the subject. For example, in the most preferred form, the magnet is disk-shaped; has an approximate outer diameter of 30 to 40 cm; includes a flat, easy-to-clean surface on one side for patient accessibility; and is supported and heat-sunk on the other side of the magnet. Such an embodiment is illustrated by FIGS. 1A–1C respectively.

Figure 1B:
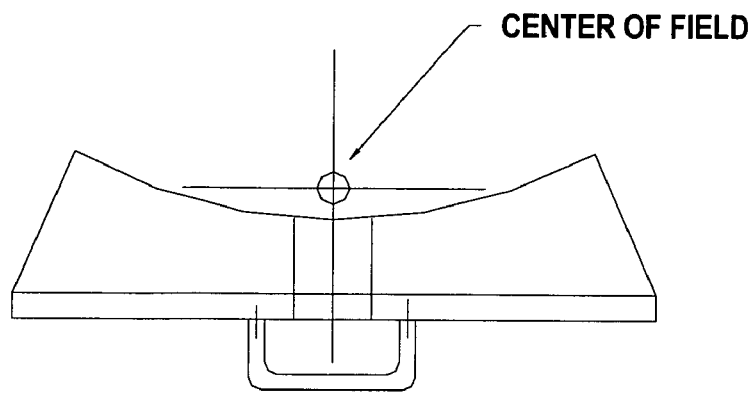
Figure 1C:
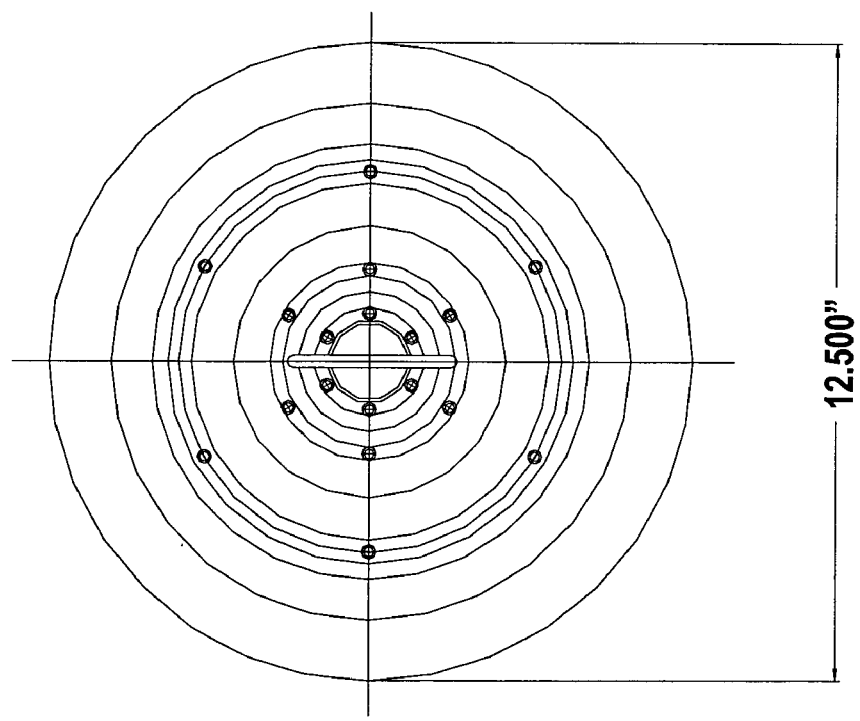

Also, the asymmetrical, circular magnet illustrated by FIGS. 1A–1C respectively is typically associated with an electronic control system and power supply built into a base unit coupled to the magnet. The electronic control system of the magnet is desirably configured to implement magnetic field variations in a range of approximately +/−1.0 mT (or 10 Gauss); to provide a field modulation of +/−0.1 to 0.5 mT (or from 1 to 5 Gauss); and to offer a field control and temperature monitoring capability.

Figure 2:
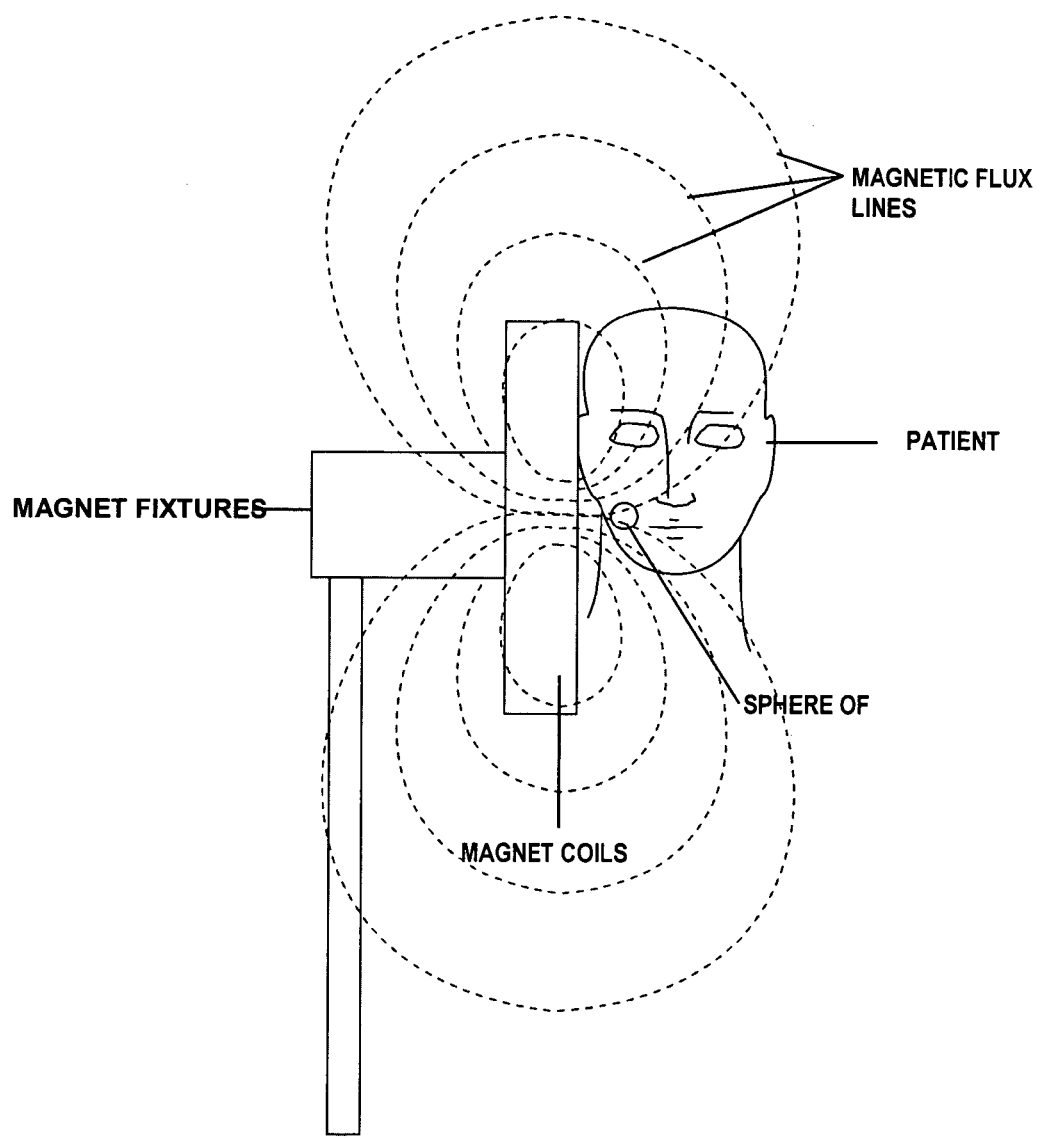
FIG. 2 is a diagram of orientation and patient positioning with respect to an asymmetric magnet.
Figure 3A:
FIGS. 3A–3E respectively are illustrations of different resonator constructs.
Figure 3B:
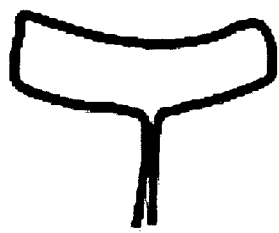
Figure 3C:
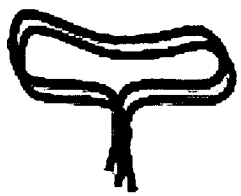
Figure 3D:
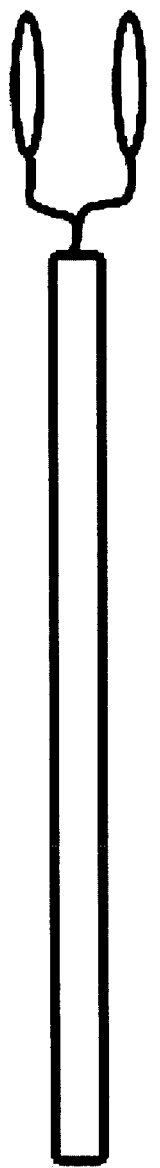
Figure 3E:
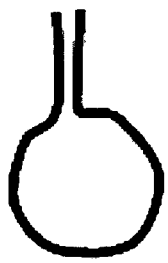

Moreover, as shown in FIG. 2, the preferred embodiment of the asymmetric, disk-shaped magnet is patient oriented and positioned such that the direction of magnetic flux lines lies perpendicular to the frontal plane of the magnet. In this embodiment, the magnet is configured to generate a field strength of approximately 40 mT (or 400 Gauss), with a region of uniformity over a 15 to 20 mm diameter spherical volume (DSV), whose center is located approximately 20 mm from a surface of the magnet. In addition, the field uniformity generated by the magnet over that volume is better than approximately 0.1 mT (or 1.0 Gauss) peak-to-peak, or about 2,500 ppm (0.25%).

In alternative embodiments, the magnet may include a plurality of electrical conductors divided into groups and carrying electric currents, which produce different magnetic fields of desired magnitude and spatial and temporal distribution over desired regions of space. In this construction format, the currents or current densities in the groups of conductors may or may not be of the same magnitude and polarity.

It will also be appreciated that a number of different geometries are possible for the magnet conductors according to the invention. For example, one or more groups of conductors may have a solenoidal geometry. Other examples, however, will employ one or more groups of conductors having a 'fingerprint' geometry of axial extent mounted on the surface of a cylinder or of radial extent mounted on the surface of a disc, or both.

Also, the groups of conductors may include a layer of wound wires, spiral wound tapes, radially subdivided discs. The axes of the groups may be coaxial, or parallel, but not coaxial. Furthermore, the axes of two or more groups of conductors may intersect at an arbitrary angle, or not; and the axes of two or more groups of conductors may lie at an arbitrary angle, but not be intersecting as such.

In other structural aspects, the magnet may be configured such that the conductors are superconductive and no resistive power is dissipated. The magnets also may be configured such that (a) any resistive power dissipation is minimized; or (b) the magnetic stored energy is minimized. Alternatively, a desired combination of the resistive power dissipation and the magnetic stored energy may be minimized.

Furthermore, for the benefit of the intended user of the present invention, a number of additional choices, variables, and construction possibilities are provided by the listing of Table 1 below. It will be expressly understood, however, that the listing of alternative parameters and capabilities provided by Table 1 is merely representative, illustrative, and exemplary of the construction alternatives for the magnetic field generator.

TABLE 1

Magnet System Variables

Alternative Parameters And Capabilities the conductors may be superconductive, including high critical temperature superconductors;
the spatial distribution of the magnetic field is such that it is homogeneous over a desired region;
the desired region is located within the axial extent of the groups of conductors;
the desired region is located partially outside of the axial extent of the groups of conductors;
the desired region is located totally outside of the axial extent of the groups of conductors;
the magnetic field is constant with respect to time;
the magnetic field varies with respect to time;
the magnetic field due to one set of conductors is constant with respect to time and that of another set of conductors varies with respect to time;
sets of conductors produce spatially non-uniform magnetic fields of desired spatial variation, which can be independently energized and which can operate either continuously at constant gradient strength or in a pulsed mode in which the gradient strength varies with respect to time;
no additional means of cooling is incorporated;
any heat dissipated in the coil windings is removed by air-cooling;
any heat dissipated in the coil windings is removed by liquid cooling.

Alternative Energy Sources For The Power Supply power required to energize any component of the magnet system is obtained from a power supply;
power required to energize any component of the magnet system is obtained from a battery;
power required to energize any component of the magnet system is obtained from capacitors;
power required to energize any component of the magnet system is obtained from a fuel cell;
power required to energize any component of the magnet system is obtained by solar power.

Magnetic Design Parameters

One underpinning of the present invention relating to the magnet is directed to a method of determining coil design parameters for the magnetic field generator using multiply-constrained nonlinear optimization techniques. The use of such refinement techniques facilitates the design of a magnet that generates highly uniform fields with reduced power requirements.

It will be recognized and appreciated that simultaneously optimizing resistive power requirements and constraining magnetic field uniformity requires the ability to manipulate a distribution of coils and of turns within a coil set. To this end, a distribution of coil turns that minimizes the desired objective function and at the same time satisfies the imposed constraints can be found by Fourier synthetic techniques. It is well known that any function satisfying Dirichlet's conditions can be expanded in a series of sines and cosines of different frequencies with appropriate amplitudes, i.e., as a Fourier series. (Dirichlet's conditions are satisfied by most functions that occur in practice). Similarly, any function can be synthesized from a series of sines and cosines with appropriate amplitudes. For example, any continuous radial distribution of current density on the surface of a disc can be represented as a smooth function of cylindrical radius, rho, using a Fourier series whose variable is rho.

The amplitudes of the terms in the Fourier series is determined in such a way that, for example, the resistive power dissipation is minimized while at the same time field uniformity constraints are satisfied. The smooth distribution of current density so obtained is then closely approximated by a distribution of unevenly spaced conductors, each carrying the same current.

In the refinement technique as presently implemented, the axial and radial positions, and the axial and radial dimensions of a set of coils, as well as the coil current densities are determined in such a way that a desired objective function is minimized while appropriate constraints are satisfied. The technique used to calculate the optimization variables, i.e., the amplitudes of the terms in the Fourier series, or the coil positions, shapes and current densities, etc, is described below. The problem to be solved is highly non-linear; and objective function gradient evaluations are impracticable analytically, if not impossible. This obstacle precludes the use of many efficient function minimization methods.

In view of the foregoing, the present invention first employs an algorithm to find the minimum value without regard to constraints. In one aspect of this embodiment, the algorithm is implemented as a variant of the conjugate direction method disclosed by Powell [see Brent, R. P., 1973, "Algorithms for Minimization without Derivatives," Prentice-Hall, Englewood, N.J.; and Powell, M. J. D., 1964, "An efficient Method for Finding the Minimum of a Function of Several Variables without Calculating Derivatives," Comp. J., 7, 155–162, both of which are expressly incorporated herein by reference]. This algorithm does not require any information concerning the derivatives, with respect to the optimization variables, of the objective function (in this case the resistive power); thus only function evaluations are required.

The technique then incorporates specific constraints. This outcome is achieved by using a modified objective function which is the sum of the true objective function and the product of a penalty function and an adjustable numerical multiplier. The penalty function is such that its value increases as the extent of a constraint violation increases. The true objective function is the resistive power; and the constraint is such that the field uniformity should be better than a preset desired value. Then, provided the numerical multiplier is large enough, minimization of the modified objective function—i.e., the sum of the resistive power and the penalty involving the field uniformity—will favor coil configurations where the field uniformity is closer to the desired value. One instance of a suitable algorithm involving such a modification utilizes Bertsekas's augmented Lagrangian multiplier modification of the exterior penalty method [see Bertsekas, D. P., 1982, "Constrained Optimization and Lagrange Multiplier Methods," Academic Press, which is expressly incorporated herein by reference].

The technique then proceeds iteratively, by solving each of a sequence of unconstrained minimizations of the modified objective function. In each iteration the modified objective function is minimized and progress is made towards satisfying the field uniformity constraints. Between iterations the value of the numerical multiplier applied to the penalty function is appropriately adjusted upward to progressively drive the value of the constraint violation towards zero. Ultimately, the field uniformity is driven to be within specification so that the penalty term is zero and the process then proceeds to minimize the resistive power only.

Constraints other than field uniformity also may be applied during the solution process; examples of other constraints include, but are not limited to, constraints on parameters such as maximum current density, coil dimensions and locations, and stored energy.

Once having obtained such a solution, the method further determines thermal and mechanical characteristics of the proposed coil design. For example, in various aspects the method may make adjustments to coil length, conductor thickness; and also repeat the algorithmic process multiple times to obtain an optimal manufacturable coil design substantially meeting a set of desirable design specifications.

Exemplary approximate values of coil design parameters resulting from the method of this embodiment are given below in Table 2. The values set forth in Table 2 are provided primarily for purposes of illustration; and these values reflect merely preliminary design considerations based on the theoretical power and size assumptions. In particular, these values are based on a coil design including a coil former of 254 mm (or 10 inches) OD machined to accommodate square cross-section copper wire windings.

TABLE 2

| FUNCTION | VALUE | UNITS |
| --- | --- | --- |
| Wire size | 13 | AWG |
| Number of coils | 4 | |
| Turns | 12–144 | |
| Resistance | 897 | milliohm |
| Inductance | 8.84 | millihenry |
| Field strength | 0.04 | tesla |
| Operating current | 54.4 | ampere |
| Operating voltage | 48.8 | volt |
| Current density | 1630 | Amp/cm$^2$ |
| Resistive power | 2.65 | kW |

The Generated Magnetic Field

As discussed above, the magnetic field produced by the magnet may be modulated to increase measurement sensitivity. Accordingly, for purposes of practicing the present invention, a method for achieving a magnetic modulation field within +/−0.1 to 0.5 mT (1 to 5 Gauss) is desirable. This range includes the incorporation of capabilities for variable modulation frequencies, so that a modulation frequency that reduces or minimizes microphonics can be chosen for a particular resonator and conditions (in contrast to conventional modulation techniques in which only a single modulation frequency is available for an EPR measurement).

In effect, modulation coils should be designed and constructed to provide effective magnetic field modulation within the human mouth with a magnetic field uniformity of +/−10% over the view of view.

The magnet is configured to provide effective and rapid access for the human head by incorporating an essentially flat design with a region of appropriate magnetic field uniformity located at the teeth that are being measured. Such access and positioning is shown by FIG. 2.

Also, as shown by FIG. 5, a positioning device may be employed together with the magnet (e.g., a locating hole with a latch and a bite-bar) for precise alignment of the jaw of the person being evaluated with respect to the volume of the uniform magnetic field (discussed further in connection with FIG. 4 below).

B. The Resonator Construct

The present invention provides resonator constructs that allow and facilitate in vivo post-exposure dosimetry assessment. By definition, a resonator is a structure comprising inductive and capacitive elements (such as a coil and capacitor) forming an electrically resonant circuit tuned to the frequency of the expected EPR signal. It is generally connected to the spectrometer using a coaxial transmission line of known impedance (e.g., 50 ohms). The impedance of the resonant circuit is adjusted to that of the transmission line and the spectrometer electronics.

For the present invention, the resonator construct can be considered as comprising two principal parts: the body of the resonator, containing matching and tuning circuit elements; and the inductive coil, which typically takes form as a loop of wire that is placed in contact with the tooth of interest. Accordingly, a number of novel resonator constructions and unique designs comprising inductive coils and matching/tuning circuits are provided by the present invention which are suitable for rapid and useful dosimetry assessment of radiation exposure via EPR measurements in the field within minutes of exposure.

For example, the preferred resonance construct can emit and apply a radiowave on-demand in the frequency range from about 0.3 to 3.0 GHz. The circuitry of the resonator is constructed to emit radiowaves which are directed and applied to the substance of the chosen tooth.

Moreover, the resonator construct of the present invention has features that enable it to fit within the human mouth and achieve high accuracy and sensitivity. Several desirable configurations of resonators are described below. Merely to demonstrate and illustrate the range and variety of resonator constructs useful with the present invention, FIGS. 3A–3E are provided.

A specific resonator configuration can be chosen for particular use circumstances from among the following:

(i) A loop specially shaped to fit well on surface of teeth within the mouth of human subjects;

(ii) An extended loop that can fit over two or more teeth;

(iii) Multiple loop configurations that will obtain signals from several teeth simultaneously; and (iv) A resonator with fluid or flexible solid surfaces which has very low loss of the radio-frequency field, that will provide excellent transmission of microwaves and signal between the resonator and the teeth; and produce an essentially ideal geometry that overcomes the irregular and variable shape of teeth.

(v) A special patient positioning fixture incorporating an optimized resonator design is an unique aspect of this invention. This feature will allow in vivo measurement, as well as rapid, reproducible assessment of personnel radiation exposure via EPR measurement in the field within minutes of exposure.

FIG. 3 as a whole is an illustration of several different resonator coil designs according to the present invention. Various features of the illustrated resonators shown by FIGS. 3A–3E facilitate fit within the human mouth and achieve high accuracy and sensitivity in dose measurements. Representative examples of suitable resonator designs according to the present invention include a loop specially shaped to fit well on the surface of teeth as shown by FIG. 3A; an extended loop that can fit over two or more teeth as shown by FIG. 3B; and multiple loop configurations that obtain signals from several teeth concurrently or simultaneously as shown by FIGS. 3C–3E. In some embodiments, a resonator may be configured with fluid or flexible solid that has very low loss of the radio-frequency field and that provides efficient transmission of microwaves and signal between the resonator and the teeth (i.e., producing essentially ideal geometry that overcomes the irregular and variable shape of teeth). Some illustrative fluids and flexible solids include those listed by Table 3 below.

TABLE 3

| Illustrative Fluids And Flexible Solids |
| --- |
| Fluids |
| Silicone oil; Paraffin; Water (non-ionic – low conductivity) |
| Flexible solids |
| Polyethylene; Nylon; Teflon; Polystyrene; Polyvinylchloride |

Figure 4:
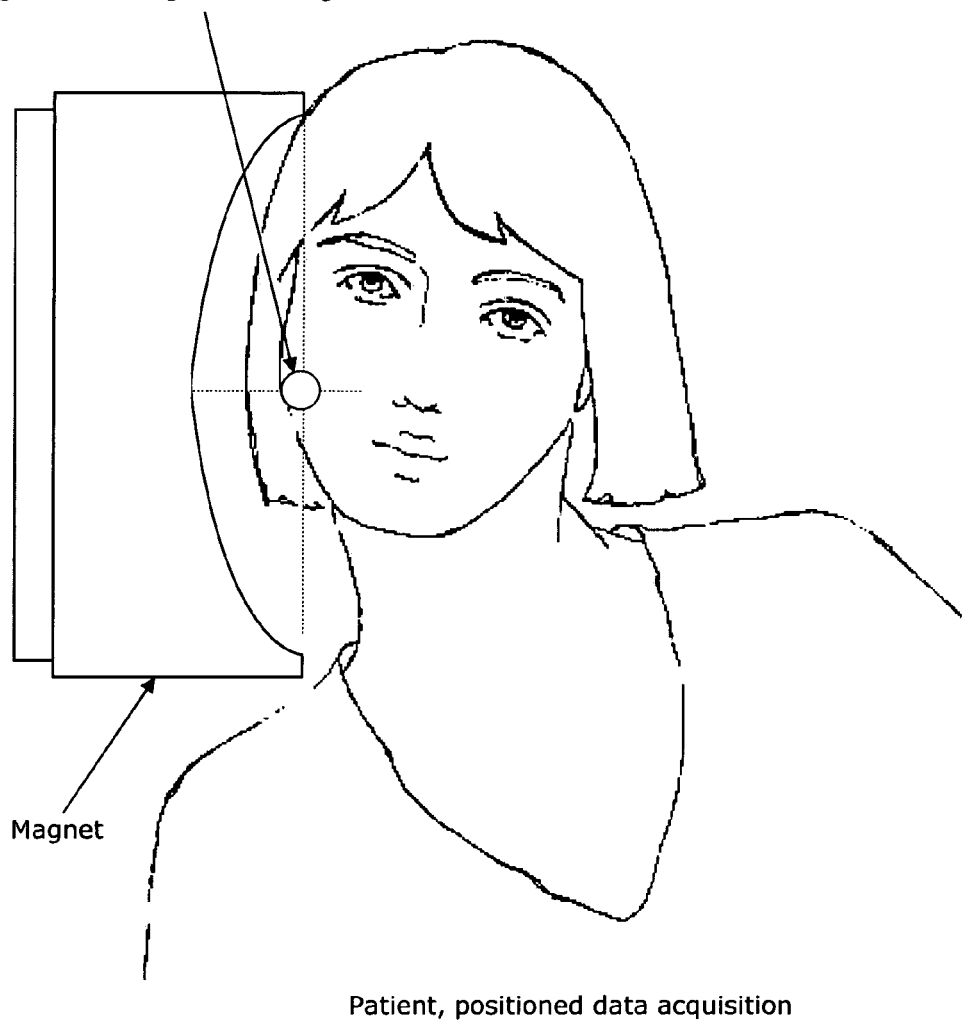
FIG. 4 is an illustration showing the relative positions of a living subject with respect to the magnetic field generator.
Figure 5A:
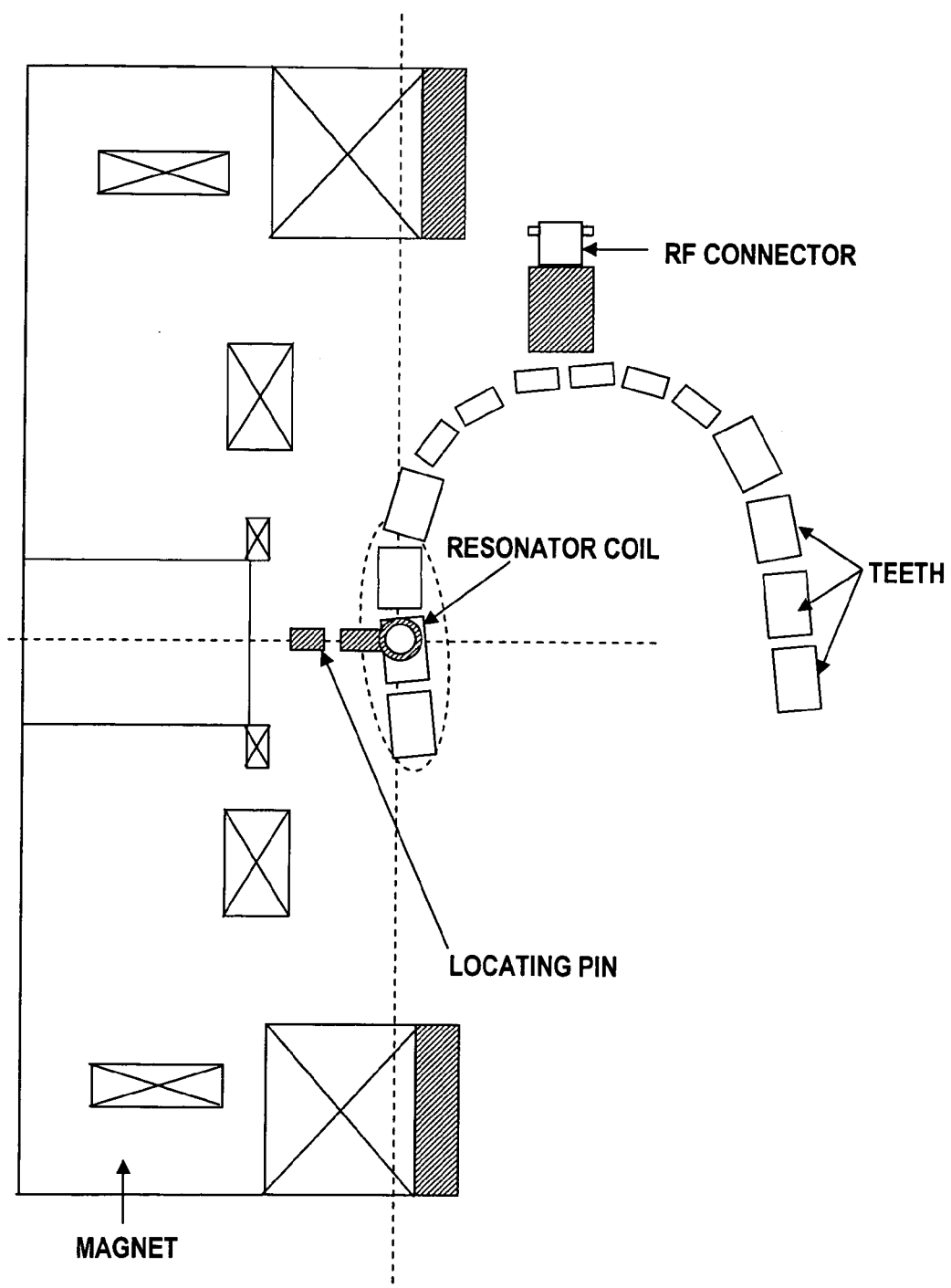
FIGS. 5A and 5B respectively are illustrations of positioning the apparatus of the invention with respect to the resonator construct with positioning bar and locating pin when situated on the patient's teeth.
Figure 5B:
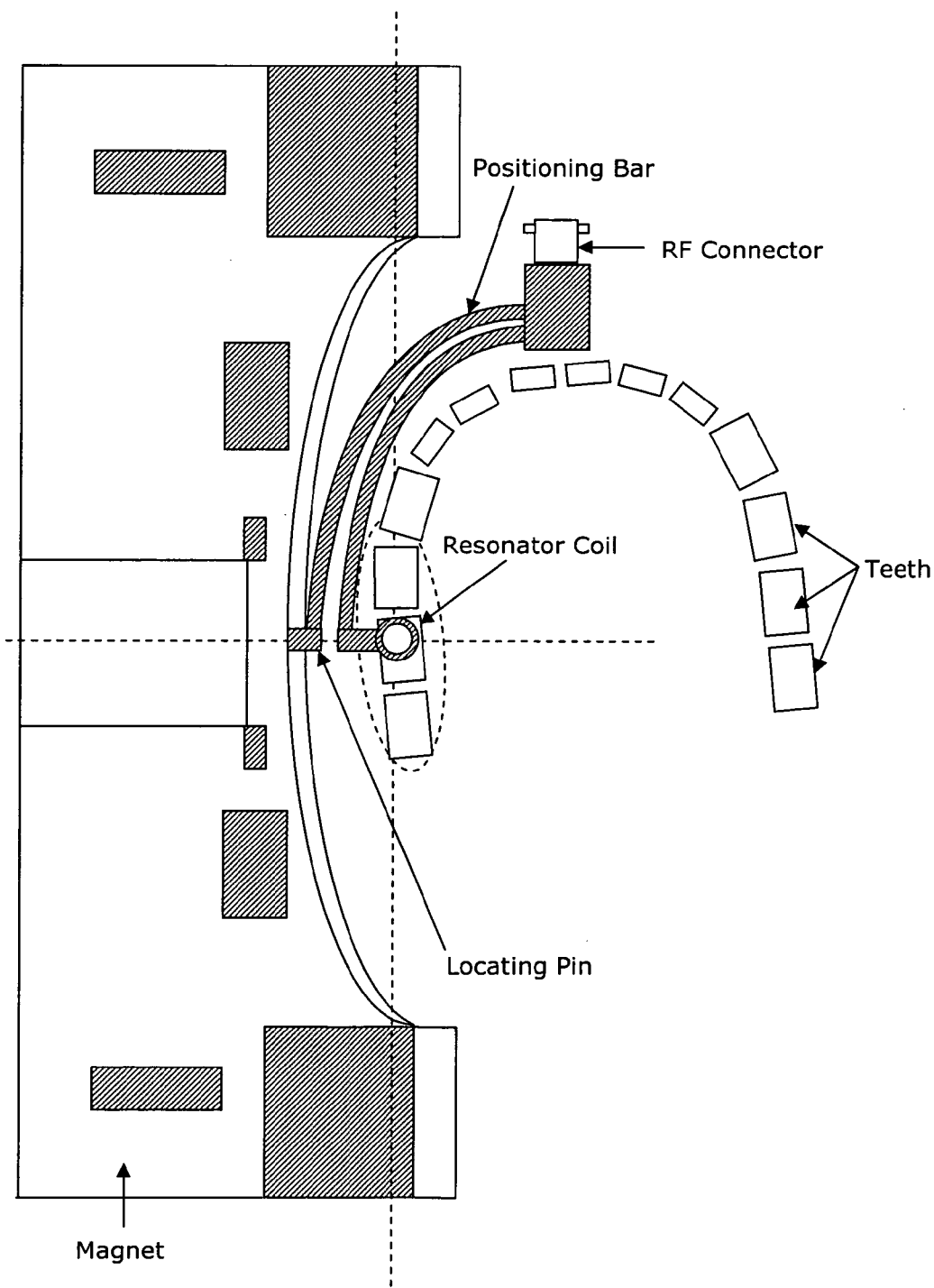

Moreover, as shown by FIG. 4, a resonator design may be implemented together with a subject-positioning fixture that facilitates placement of a subject with respect to the magnet system of FIG. 1. Also, as illustrated by FIGS. 5A and 5B respectively, the resonator structure may be implemented as a probe holder including a bite bar enclosing the resonator coil and coaxial cable; and be attached to an RF connector, together with a positioning bar and locating pin that engages with the magnet. If desired, the probe holder may be formed of disposable materials (e.g., made of plastic) as is shown by FIGS. 6A–6C respectively.

C. The EPR Spectrometer

An essential capability for the apparatus is to obtain and to process an EPR signal in order to detect and measure the specific radiation-induced signals within teeth; and to enable the prior radiation dose to be determined with explicit calculation of the uncertainty of the measurement. This is achieved by the use of an EPR spectrometer; and the empirical data resulting from such EPR spectra measurements is graphically shown by FIGS. 7A and 7B respectively.

In this aspect of the invention, the EPR spectra are obtained at two different microwave powers via an automated control system. Then, based on the knowledge of the nature of the spectra (as described further below), the magnitudes of both the radiation-induced signal and the intrinsic background signal in the teeth are each determined through an automated computer program. This determination is based on the known shape of the radiation-induced signal, the known shape of the background signal, the different g-factor of the background signal, and the different power saturation of the background signal permitting the determination of the signal due to the radiation.

The EPR spectrometer can be utilized in a variety of different formats. These preferably include the following:

(i) the uncertainty in the measurement of the radiation induced signal is calculated;

(ii) pulsed EPR techniques are employed for data acquisition;

(iii) the signal-to-noise ratio is enhanced by a unique method of scanning, which uses repetitive scanning of the spectrum for only the region of the maxima and minima of the radiation-induced and the background signals;

(iv) the characteristics of the radiation-induced signal and the background signal are obtained as described below, and these are used as the library against which the measurement of each subject is compared to compute the radiation-induced dose and the uncertainty in its measurement.

A Preferred Format

Figure 7A:
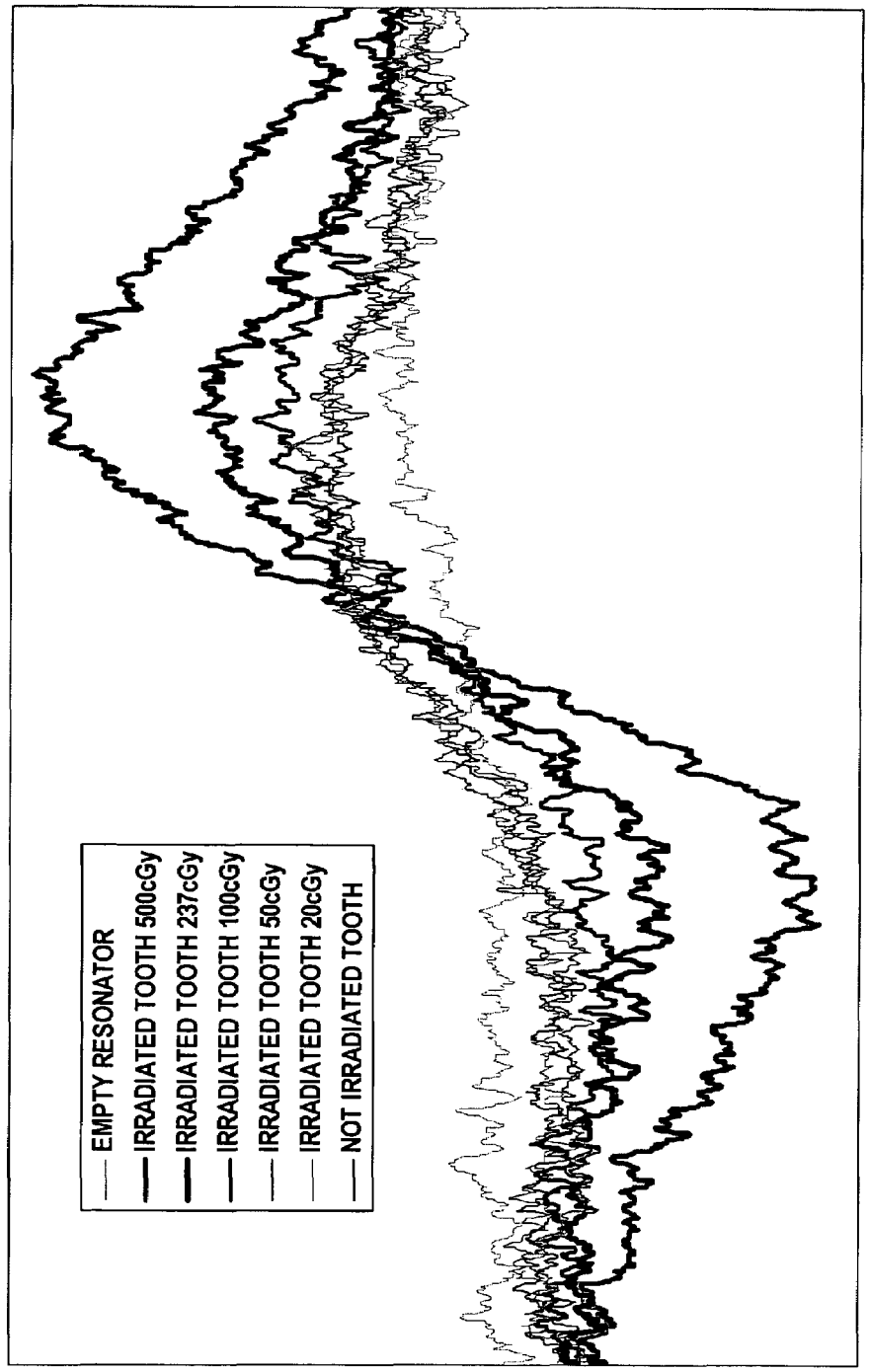
FIGS. 7A and 7B respectively are graphs showing EPR spectra obtained from human teeth exposed to different doses of ionizing radiation.
Figure 7B:
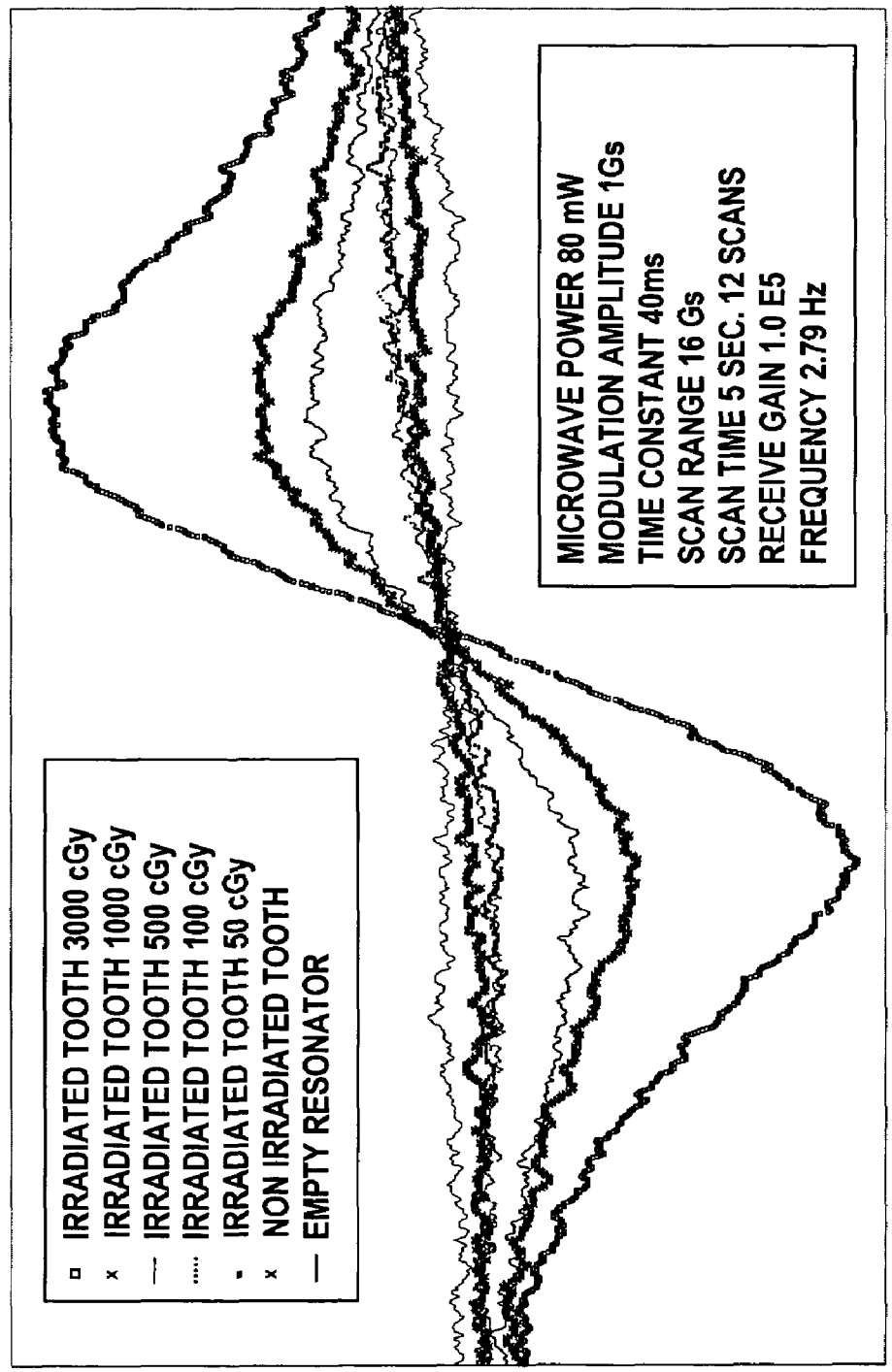

As illustrated by FIGS. 7A and 7B, a library of EPR spectra of isolated human teeth before irradiation and after irradiation with known doses is intentionally created. This library is then used as a reference standard to provide the initial data for the program to calculate the radiation induced signals subsequently measured in-vivo. Each spectrum is the average of 10 spectra taken at different orientations of tooth in magnetic field. The doses of irradiation illustrated by FIG. 7 as a whole are 50, 100, 300, 500, and 700 cGy.

In substance, each 700 cGy spectrum is fitted using the EW Voigt program (based on the fitting of two centers of Lorentzian line shapes). The mean of the parameters of fitting 700 cGy spectra are derived and used for the subsequent calculations. These standard parameters are then used to fit the lower dose spectra. Each of the 50–500 cGy spectra is fitted using a standard set of parameters to derive signal intensity of each spectrum of irradiated teeth. The signal intensity is normalized by dividing by $(ab)^{3/2}$, where a and b are dimensions of the tooth.

Subsequently, the data from the in vitro irradiated teeth are used to develop a calibration of signal intensity (Y) versus dose (X). Assuming that the signal intensity (Y) is a linear function of the dose (X), one uses the linear regression $Y=b_0+b_1X+\epsilon$, where $b_0$ is the intercept; $b_1$ is the slope; and $\epsilon$ is the error term. Employing a least squares procedure, one can estimate $b_0$ and $b_1$ from the calibration data and obtain the predicted value as: $Y=b_0+b_1X$. Using the inverse regression method, one then can determine the dose of an experimental measurement from the signal intensity of that measurement. A more detailed explanation of this procedure is given hereinafter.

The data from the in vitro irradiated teeth used to calculate the radiation induced signals then is adjusted based on their relation to the data that are obtained from the in vivo measurements on teeth irradiated in vivo in patients undergoing radiation therapy. These unique data will provide dose response relationships in each tooth, by making weekly measurements during the course of radiation therapy. By measuring at more than one site in these patients, estimates can be established for the variability in dose-response calculated from known doses in different teeth in the mouth of the same individual.

Calibration and Field Usage

The use of patients undergoing radiation therapy will provide a well-characterized radiation dose-response relationship—via measurements made weekly over the course of radiation therapy. Such determinations facilitate calibration of the in-situ response to radiation of human teeth measured and irradiated in-vivo.

In yet another aspect of the invention, the configuration and prior calibration of the EPR spectrometer will facilitate operation in the field by modestly trained individuals. For example, an EPR spectrometer may be configured such that the operator can push a single button to take a dose reading. The EPR spectrometer also may include an optional button that indicates the time over which the measurement is taken. Also, the EPR spectrometer may be configured such that the dose measurement is provided in the form of a dose with an estimate of the range of values that are within a 95% probability of being correct. This would include information on the clinical implications of the doses within the range that pertain to the subject being measured.

Having thus described at least one illustrative embodiment of the invention, various alterations, modifications, and improvements will readily occur to those skilled in the art. Such alterations, modifications, and improvements are intended to be within the spirit and scope of the invention.

III. The Methodology of the Invention

The method of operation for the present invention utilizes electron paramagnetic resonance (EPR) to measure exposure to ionizing radiation by means of the long-lived changes induced in hard tissues such as teeth and bones. It uses a modified EPR technique in terms of using a magnetic field to establish different energy levels for unpaired electrons, which have a net magnetic moment because of the spin. A limited radio-frequency electromagnetic field is applied to obtain transitions between the energy levels as established by the magnetic field. Modulation of the magnetic field is used to enhance the sensitivity of the procedure.

The present method is capable of measuring clinically significant doses of radiation after exposure based on EPR measurements in teeth. The dose range that can be measured using the invention is from less than 50 cGray (cGy) to greater than 20 Gray (Gy). This determination of doses covers the entire clinical range of exposures, from those doses of radiation that are very unlikely to cause any acute clinical effects through those radiation doses expected to result in death of the person within hours.

A preferred method for obtaining and processing the EPR signal is provided which will achieve the required sensitivity for the specific radiation-induced signals in teeth, thereby enabling the dose to be determined with explicit calculation of the uncertainty of the measurement, and serve as an aid in clinical decision-making. This preferred method comprises the following:

(a) The spectra are obtained at two different microwave powers via an automated control system. Then, based on the knowledge of the nature of the spectra as described below, the magnitudes of both the radiation-induced signal and the intrinsic background signal in the teeth are each determined through an automated computer program. This determination is based on the known shape of the radiation-induced signal, the known shape of the background signal, the different g-factor of the background signal, and the different power saturation of the background signal permitting the determination of the signal due to the radiation.

(b) The uncertainty in the measurement of the radiation induced signal is calculated by the same program.

(c) The signal-to-noise is enhanced by a unique method of scanning, which uses repetitive scanning of the spectrum for only the region of the maxima and minima of the radiation-induced and the background signals.

(d) The characteristics of the radiation-induced signal and the background signal are obtained as described herein and these are used as the library against which the measurement of each subject is compared to compute the radiation-induced dose and the uncertainty in its measurement.

(e) A library of EPR spectra of isolated human teeth before irradiation and after irradiation with known doses is created and used to provide the initial data for the program to calculate the radiation induced signals. Each spectrum is the average of 10 spectra taken at different orientations of tooth in magnetic field. The doses of irradiation are 50, 100, 300, 500, and 700 cGy. Each 700 cGy spectrum is fitted using the EW Voigt program (based on the fitting of two centers of Lorentzian line shapes). The mean of the parameters of fitting 700 cGy spectra are derived and used for the subsequent calculations. These standard parameters are then used to fit the lower dose spectra. Each of the 50–500 cGy spectra is fitted using a standard set of parameters to derive signal intensity of each spectrum of irradiated teeth. The signal intensity is normalized dividing by $(ab)^{3/2}$, where a and b are dimensions of the tooth.

(f) The data from the in vitro irradiated teeth are used to develop a calibration of signal intensity (Y) against dose (X). Assuming that the signal intensity is a linear function of the dose, one uses the linear regression $Y=b_0+b_1X$, where $b_0$ is the intercept, $b_1$ is the slope, and $\epsilon$ is the error term. Employing a least squares procedures, one can estimate $b_0$ and $b_1$ from the calibration data and obtain the predicted value as $Y=b_0+b_1X$. Using the inverse regression method, one can then determine the dose (X) of an experimental measurement from the signal intensity of that measurement.

(g) The data from the in vitro irradiated teeth used to calculate the radiation induced signals then will be adjusted based on their relation to the data that are obtained from the in vivo measurements on teeth irradiated in vivo in patients undergoing radiation therapy. These unique data will provide dose response relationships in each tooth, by making weekly measurements during the course of radiation therapy. By measuring at more than one site in these patients, the user also will be able to establish an estimate for the variability in dose-response calculated from known doses in different teeth in the mouth of the same individual.

The configuration of the spectrometer that makes it feasible to be operated and utilized in the field by modestly trained individuals includes the following:

(1) Computer control of operational parameters such that the operator can push a single button to operate the spectrometer to take the reading. The operator also will have an optional button that indicates the time over which the measurement will be taken.

(2) Output of the measurement in the form of a dose with an estimate of the range of values that are within a 95% probability of being correct, including information on the clinical implications of the doses within the range that pertains to the individual in whom the measurement has been made.

It is suggested and recommended that the use of patients undergoing radiation therapy provides a well-characterized radiation dose-response relationship though measurements made weekly over the course of radiation therapy. This provides a calibration of the response to radiation of human teeth measured and irradiated in-situ under in-vivo conditions.

Alternative Formats of the Methodology

A. Accurate Determination of the Radiation Dose Via Tooth Dosimeter Using EPR Measurements:

Unlike previous efforts to measure accurately the radiation dose, the present invention (a) accounts for tooth measurements and (b) computes standard error prediction (error analysis). The exposed radiation dose is determined using the inverse of the calibration equation that relates a characteristic of the EPR signal to the radiation dose and the tooth size. The calibration equation is derived from experimental data where the given radiation dose is known.

To compute the standard error of prediction the concept of inverse regression in combination with delta-method is used (N. R. Draper and H. Smith, Applied Regression Analysis, New York: Wiley, 1998). Confidence intervals and ROC curve for dose may be computed as well.

The key to a successful dose determination is an adequate choice of the EPR signal characteristic. Previously investigators took the amplitude (the difference between maximum and minimum EPR signal). Although the amplitude and dose are somewhat correlated, better results may be obtained if other specific/sensitive points on the EPR signal are taken.

Since the ends of the EPR signal are greatly affected by the microphonic/background signal, the representative region or point(s) on the signal curve is concentrated around the center point (512, 0) where the curve intersects the abscissa. Moreover, since the EPR signal should go through the center regardless of the radiation dose, the sensitive point should be at a certain distance from the center. Extensive computer computations that simultaneously process the available experimental data (a 1024×17 matrix) are used to locate the area/points on the EPR curve that minimizes the error of the dose prediction. Mathematically, it was found that the most error-free area resides to the left of the center in the neighborhood of 450th signal point (+/−50 points).

Also, the final model for the calibration curve has the form $S=a*A+b*D*(A-c)$, where S is the EPR signal intensity at a sensitive point, A is the area of the tooth (an estimate of the enamel amount), D is the radiation dose, and a,b,c are regression parameters to be estimated. These parameters have the following interpretation: Parameter a estimates the EPR signal at zero radiation dose (background), parameter b estimates the rate at which signal increases with the dose, parameter c adjusts the tooth size for the enamel amount. After the coefficients are determined the dose is calculated as $D=(S-a*A)/[b(A-c)]$.

Several methods have been compared in terms of the precision of the dose measurement: (a) traditional, where the radiation dose is correlated to the parameters of the Lorentz curve; (b) three-point; (c) two-point; (d) one-point on the EPR curve.

The one-point approach yields the standard error of the dose determination equal to 30 cGy, whereas the conventional method gives 100 cGy. Furthermore, for the analyzed data, one is able to determine whether tooth was exposed to greater or less than 150 cGy with zero prediction error.

B. A Mathematical Model Library Approach to Radiation Dose Prediction Measurement Item 1: Find a quantity which characterizes the EPR signal (traditionally, amplitude), say S.

Item 2: By doing in vitro experiments on teeth with known radiation dose (D) find the relation between S and D, say a function S=F(D).

Item 3: Estimate parameters (coefficients) of this function, e.g. derive the calibration equation.

Item 4: If the EPR signal is derived, recover/predict/assess the dose by inverting the calibration equation, i.e. solve S=F(D) for D.

Item 5: Carry out the error analysis: given uncertainty of the calibration equation and signal S determine the uncertainty of the dose D.

Each of these items will be described in detail hereinafter.

Item 1: Error Analysis for the Dose Assessment

In this section, an outline is given as to how to assess the radiation dose (D) and its standard error based on calibration equation, which relates D with a characteristic of the EPR signal shape (S), e.g. amplitude or slope.

Mathematical Formulation

To simplify, it is assumed that S and D are related through a linear relationship $$S = a + bD + \epsilon \quad (1)$$

where a is the intercept term, b is the slope, and $\epsilon$ is the error term. Let a and b be estimates with known covariance matrix C derived from calibration. Let S be an estimate of the characteristic for a tooth we want to find D. Then the estimate of dose is $$D = \frac{S-a}{b} \quad (2)$$

Mathematically, the problem reduces to the assessment of the SE of D. To solve this problem we use the method of "inverse regression", Draper and Smith (1998).

Solution

Use the delta-method to find the SE of D, Rao (1973):

$$SE_D = \frac{1}{b} \sqrt{SE_S^2 + \sigma_a^2 + \frac{a^2 \sigma_b^2}{b^2} - \frac{2a\sigma_{ab}}{b}} \quad (3)$$

As a word of caution, the relative error analysis $$\frac{SE_D \%}{D}$$

may be valid for high dose, such as >500 cGy. But for low dose it is not. Indeed, $SE_D$ does not vanish but D→0 which inflates the relative error to infinity.

Nonlinear Relationship

The derivation of D and its SE is possible for nonlinear relationship as well:

$$S = F(a, b; D) + \epsilon \quad (4)$$

where F is an arbitrary function (e.g. power or exponential) and a and b are parameters to estimate. Then the recovered dose D is the solution to the equation S=F(a,b:D). To find the standard error SE, one applies the linear regression:

$$F(a, b; D) \simeq F(\hat{a}, \hat{b}; D) + (a - \hat{a})\frac{\partial F}{\partial a} + (b - \hat{b})\frac{\partial F}{\partial a}, \quad (5)$$

where partial derivatives are computed at $\hat{a}$ and $\hat{b}$.

Item 2. Calibration Equation

Calibration equation relates to characteristic S of the EPR signal to given radiation dose. The main question: what is S?

We discuss three possible approaches:

S is a parameter of a model for the EPR signal—nonlinear estimation/fit

S is the slope of the EPR signal at the center.

S is the amplitude and/or the slope between maximum and minimum points.

S is the sensitive point of the EPR signal curve (one-point analysis).

Figure 8:
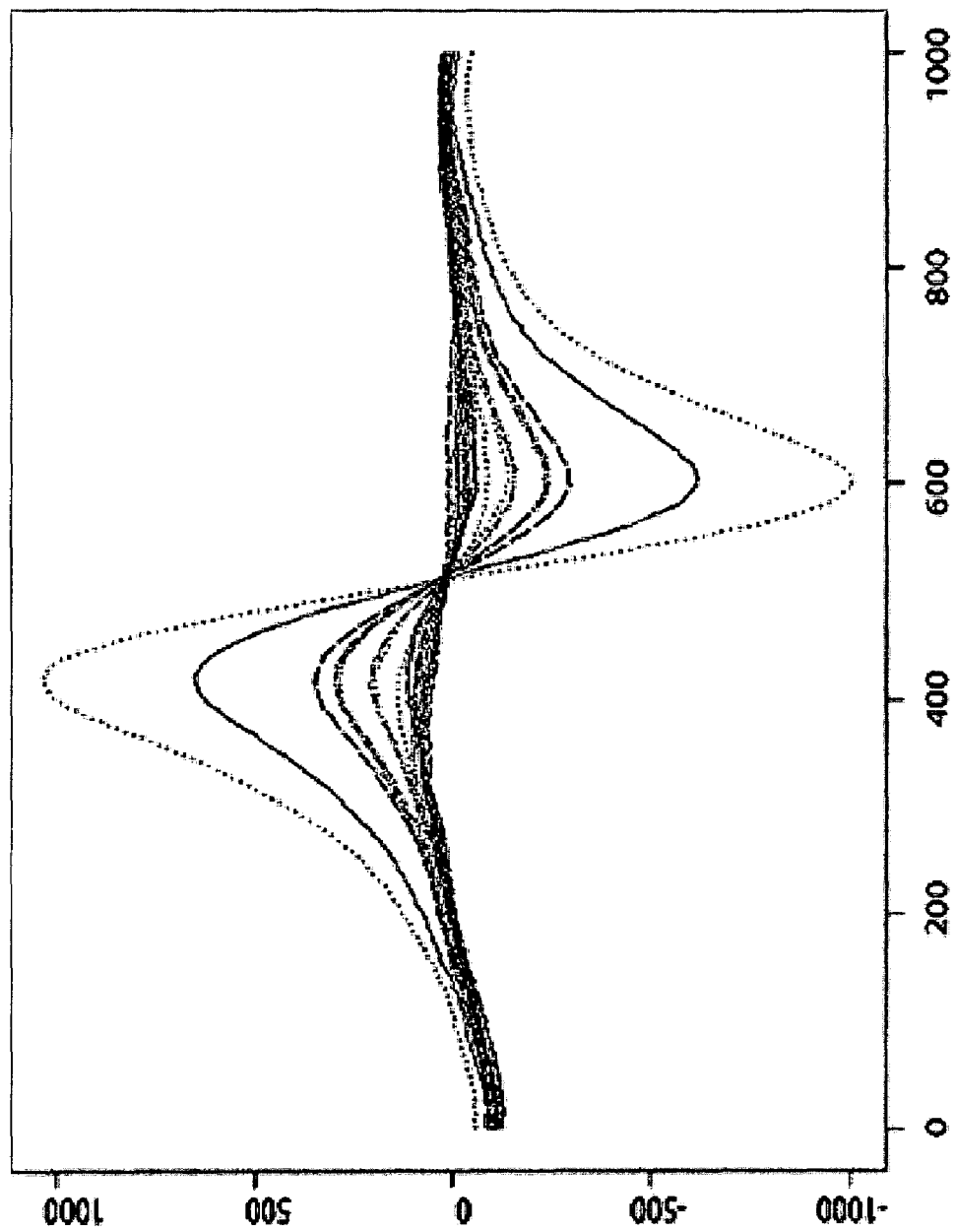
FIG. 8 is a graph illustrating mean data obtained using the present invention.

The answer is revealed by FIG. 8 which shows the Mean Data. It will be noted and appreciated that the left end of the data in FIG. 7 does not vanish. Also, the LW shape is asymmetric. On this basis, therefore, it is suggested that the analysis be confined to a limited interval, such as the (200, 800) interval of the curve.

Item 3. Modeling of the EPR Signal Slope

Several shapes for the EPR signal may be suggested:

1. Lorentz Derivative $$S_L(x) = -a_1 \frac{(x-a_2)}{[a_3 + (x-a_2)^2]^2}$$

2. Gaussian Derivative $$S_G(x) = -a_1(x-a_2)e^{-a_3(x-a_2)^2}$$

3. Linear Combination of the Above $$S(x) = aS_L(x) + (1-a)SG(x).$$

Figure 9:
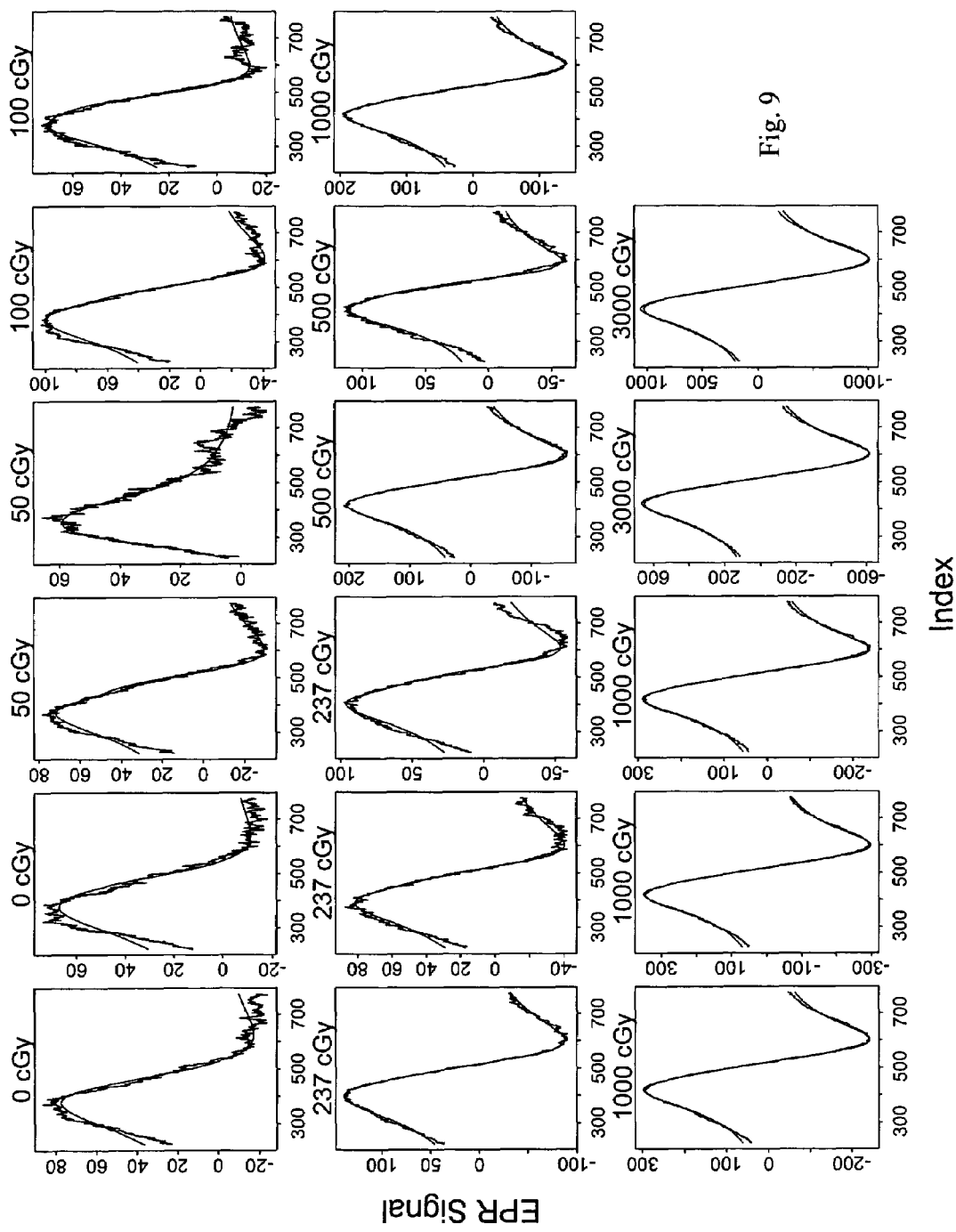
FIG. 9 is a series of graphs showing the EPR signal from teeth exposed to radiation doses ranging from 0–3000 cGy.
Figure 10:
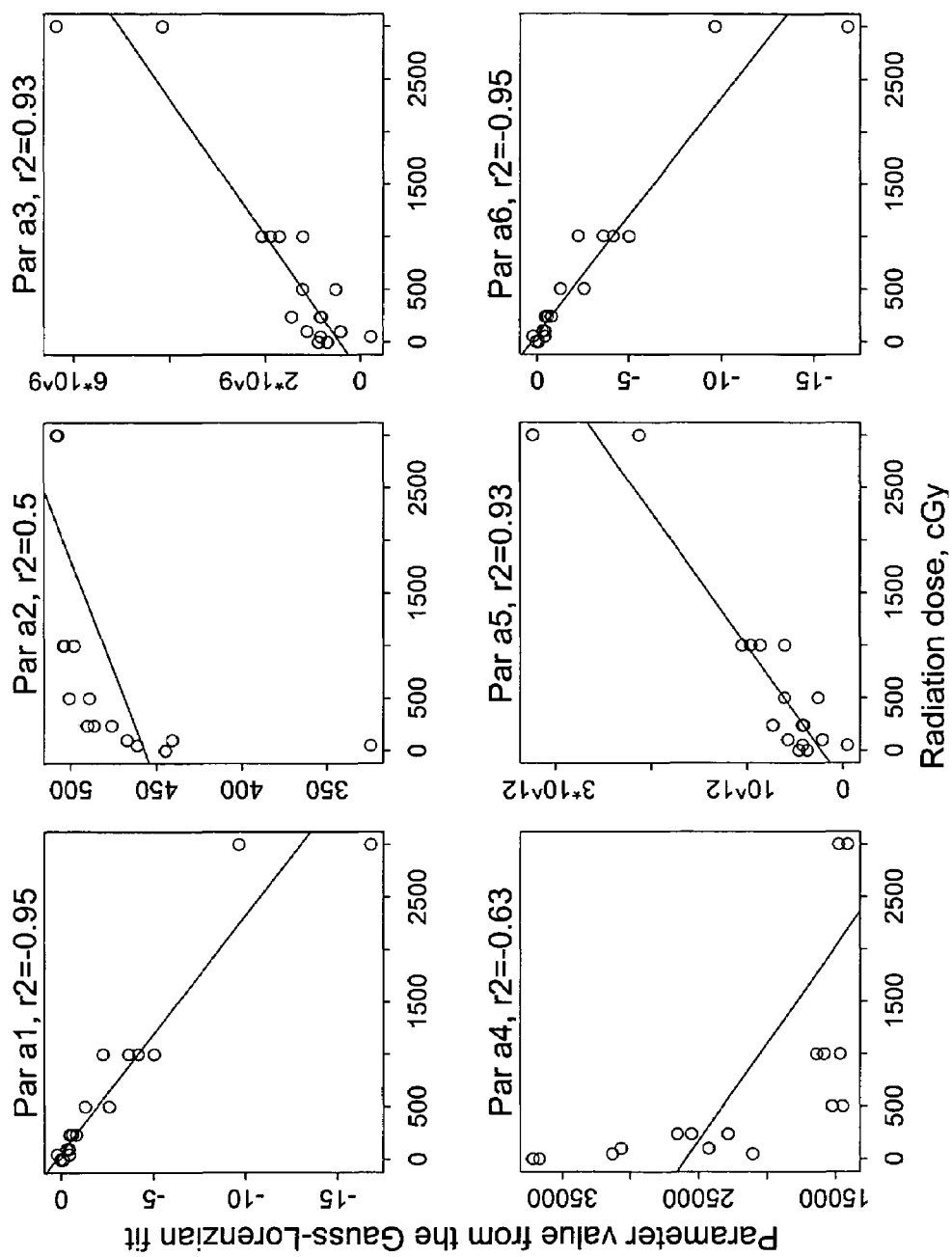
FIG. 10 is a series of graphs showing the linear fit of six operating parameters for the EPR signal as a function of radiation dose.

The tooth radiation exposure data shown by FIG. 9 overall reveals a very good fit by a linear combination of the Lorentz and Gaussian derivatives. Moreover, an almost perfect fit exists for this linear combination of derivatives at the high dose of ionizing radiation. This is demonstrated by the graphs of FIG. 10 as a whole, in which the linear fit of six different parameters of the EPR signal to radiation dose is given. The a1 parameter appears to be the most promising for use.

Item 4. Vertical Shift Approach, S

Figure 11:
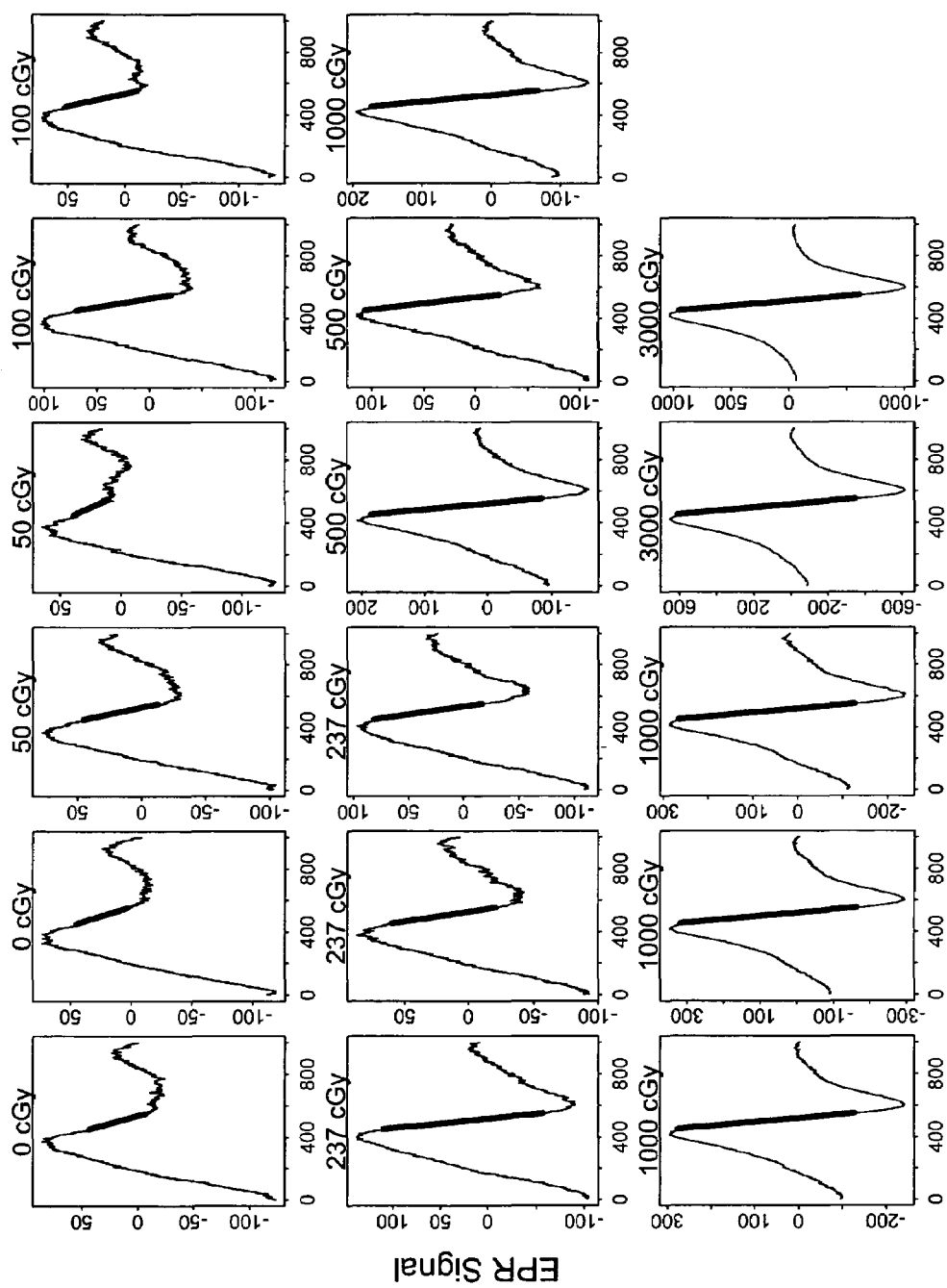
FIG. 11 is a series of graphs showing the linear function fit of the EPR signal at the center.
Figure 12:
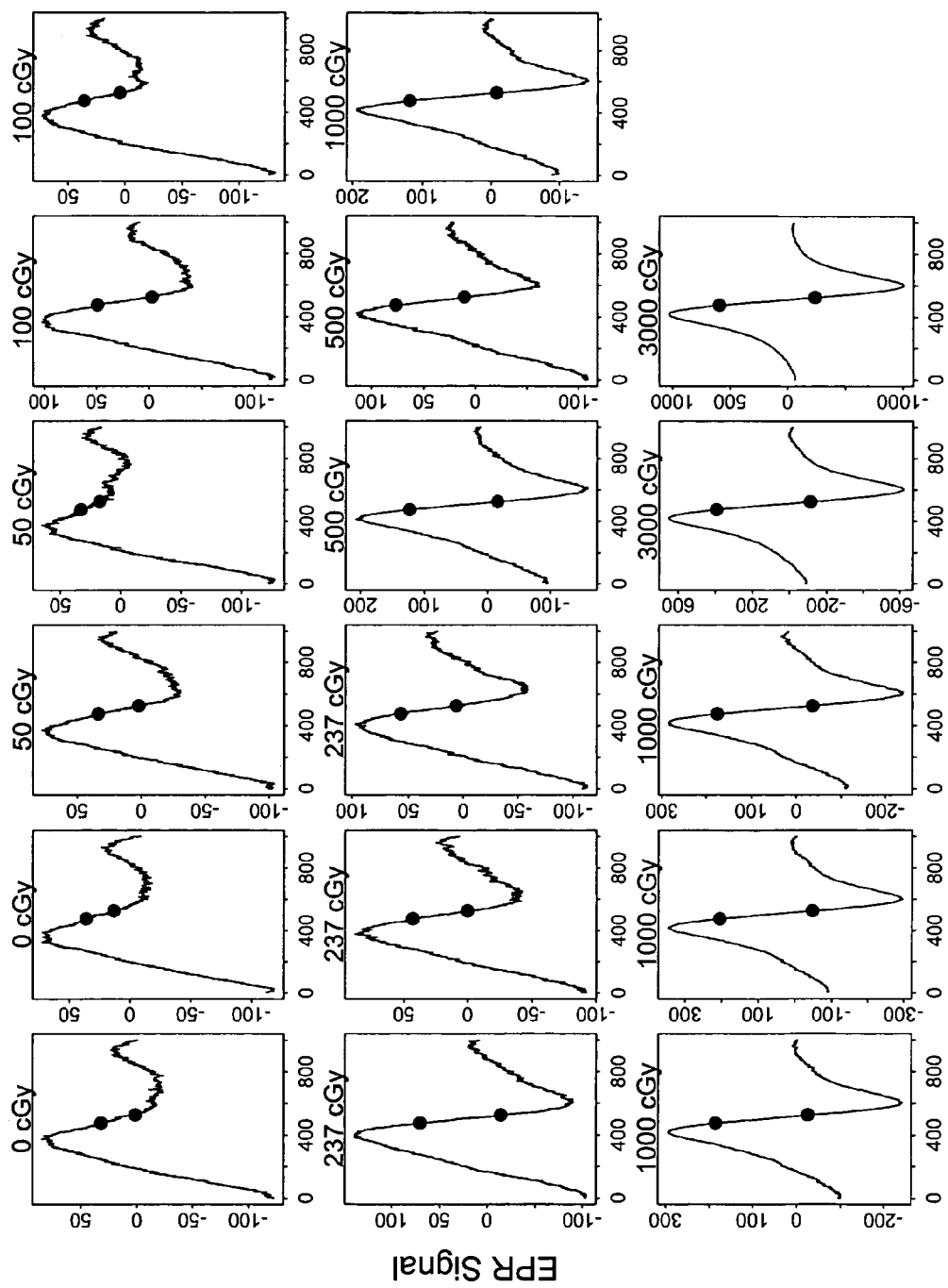
FIG. 12 is a series of graphs showing the presence of three data points in the center of the EPR signal.

A straight line is fitted to data in the center, $(512-n_0, 512+n_0)$. Then the suggested EPR signal characteristic (S) is the intercept of that line. FIGS. 11 and 12 present such data where $n_0=50$. As shown by FIG. 11 overall, the linear function fits the EPR signal at the center of the data curve. Similarly, as illustrated by FIG. 12, three data points in the center of the EPR signal can be used as a reliable estimate of the intercept.

Item 5. Adjusting for the Enamel Area of the Tooth

The intensity/strength of the EPR signal depends on the enamel area—more enamel higher intensity. The relationship between the vertical shift and dose is then adjusted as $$S=a_0A+a_1D(A-a_2),$$

where S is the EPR signal intensity.

The above-given parameters have the following interpretation:

$a_0$ is due to microphonic effect/non-irradiated tooth, depends on the enamel amount/area A.
$a_1$=dose rate
$a_2$=dose rate for tooth size adjustment
Coefficients $a_0$, $a_1$ and $a_2$ are found from linear regression:

$$S=a_0A+a_1(A\times D)-a_2D.$$

After the coefficients are determined, the dose is estimated as $$D = \frac{S - a_0 A}{a_1(A - a_2)}$$

Thus, an adjustment for the tooth size is the key for accuracy. This is empirically demonstrated by the comparative data given by Table M1 below.

TABLE M1

Prediction results based on three-point analysis

| Tooth | Dose | Pred | SE | L. Cl 95% | U. Cl 95% |
|-------|------|------|-----|-----------|-----------|
| MA | 0 | 24 | 9 | 6 | 42 |
| MC | 0 | 26 | 9 | 9 | 44 |
| M13 | 50 | 40 | 9 | 22 | 58 |
| M15 | 50 | 50 | 10 | 30 | 70 |
| M16 | 100 | 107 | 9 | 90 | 124 |
| M18 | 100 | 87 | 10 | 68 | 106 |
| M19 | 237 | 216 | 8 | 200 | 232 |
| M20 | 237 | 152 | 9 | 134 | 171 |
| M21 | 237 | 246 | 9 | 228 | 264 |
| M1 | 500 | 475 | 8 | 460 | 491 |
| M3 | 500 | 503 | 12 | 479 | 527 |
| M4 | 1000 | 1019 | 23 | 974 | 1065 |
| M5 | 1000 | 1061 | 9 | 1044 | 1077 |
| MT1 | 1000 | 990 | 8 | 975 | 1006 |
| MT2 | 1000 | 1034 | 9 | 1017 | 1050 |
| M7 | 3000 | 2975 | 32 | 2917 | 3038 |
| M9 | 3000 | 3002 | 23 | 2957 | 3047 |

Item 6: One-Point Analysis

Observations

The ends of the EPR signal are not sensitive to the radiation dose.

The middle (x=512, y=0) is not sensitive to the radiation dose.

Thus, there should exist a point on the EPR curve signal which is the most sensitive (predictive) to the radiation dose! Thus, the essential question is—how to find this point?

Figure 13:
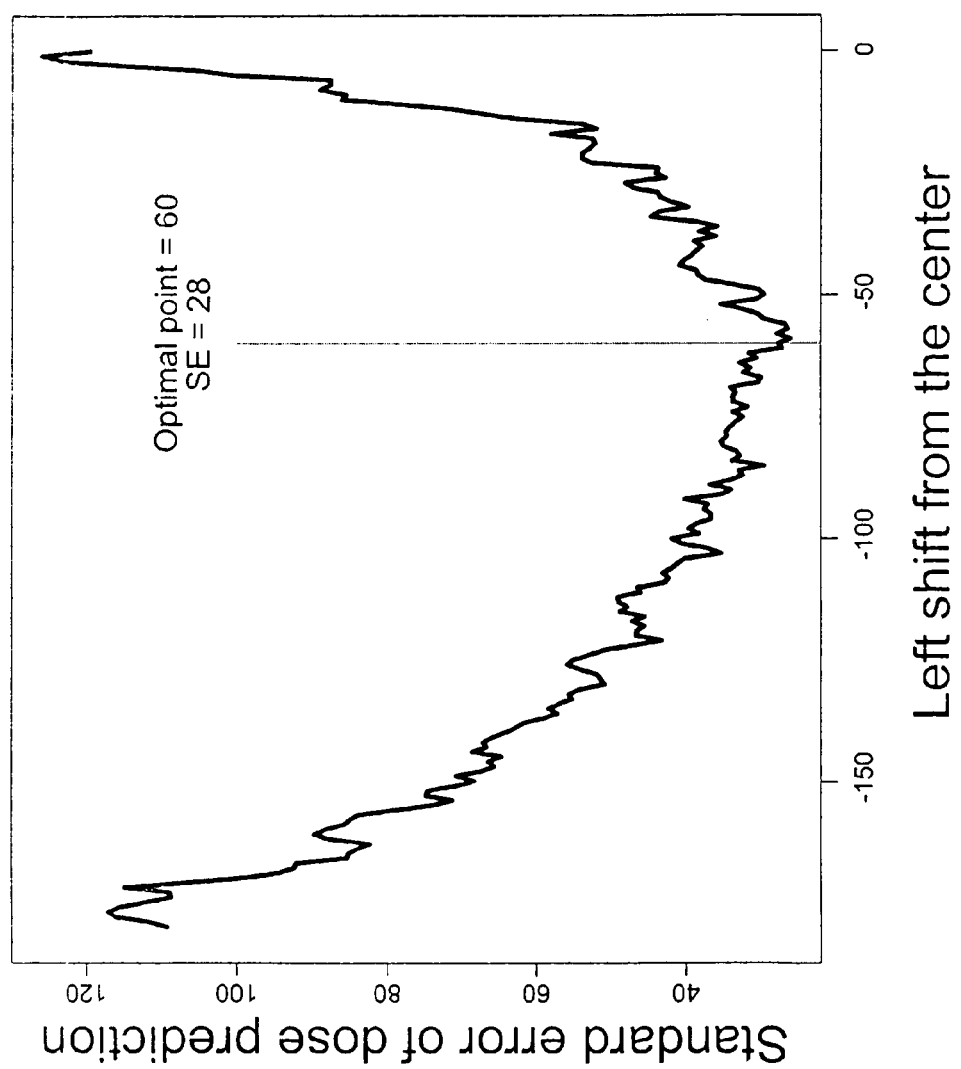
FIG. 13 is a graph showing the search for an optimal predictive data point on the EPR signal.

The search for an optimal predictive point on the observed EPR signal is illustrated by FIG. 13. As shown therein, the optimal point is a shift of 60 left from the middle.

The one-point model:

$$S_{-60}=0.345\times A+0.0031\times D\times(A-38.26),$$

$$R^2=0.999$$

with the dose prediction:

$$D = \frac{S_{-60} - 0.345 \times A}{0.0031 \times (A - 38.26)}$$

Figure 14:
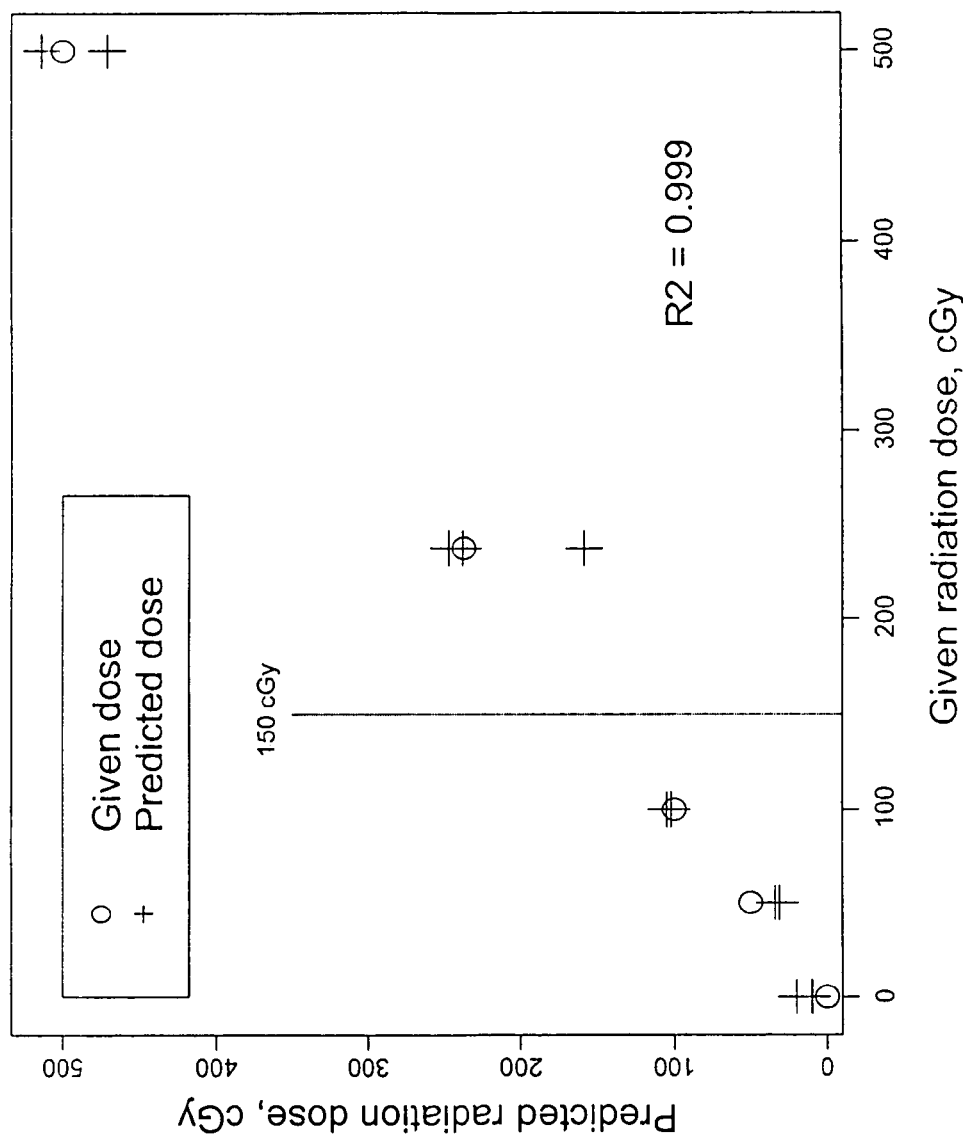
FIG. 14 is a graph showing prediction radiation dose results as a function of radiation doses up to 500 cGy.

In the one-point model system, a comparison of an empirically given radiation dose with a mathematically predicted radiation dose is shown by FIG. 14 and Table M2. Note that FIG. 14 provides an accurate correlation of prediction results with empirical data in the exposure range of up to 500 cGy. Also, the comparison of data provided by Table M2 reveals a very reliable and accurate correlation between the predicted and empirically-obtained data.

TABLE M2

Methods comparison via SE of the dose prediction

| Tooth | Dose | Vert. shift | 3 point shift | Ampl. conven. | 1 point |
|-------|------|-------------|---------------|---------------|---------|
| MA | 0 | 16 | 24 | 129 | 20 |
| MC | 0 | 15 | 26 | 86 | 10 |
| M13 | 50 | 32 | 40 | 97 | 34 |
| M15 | 50 | 49 | 50 | 250 | 31 |
| M16 | 100 | 99 | 107 | 128 | 105 |
| M18 | 100 | 104 | 87 | 243 | 102 |
| M19 | 237 | 221 | 216 | 144 | 238 |
| M20 | 237 | 148 | 152 | 182 | 159 |
| M21 | 237 | 262 | 246 | 266 | 247 |
| M1 | 500 | 486 | 475 | 357 | 471 |
| M3 | 500 | 516 | 503 | 444 | 514 |
| M4 | 1000 | 1031 | 1019 | 938 | 1031 |
| M5 | 1000 | 1064 | 1061 | 929 | 1048 |
| MT1 | 1000 | 996 | 990 | 889 | 1004 |
| MT2 | 1000 | 1016 | 1034 | 896 | 1024 |
| M7 | 3000 | 2970 | 2975 | 3089 | 2972 |
| M9 | 3000 | 3002 | 3002 | 3061 | 3001 |
| St. Error | | 31 | 31 | 99 | 28 |

Finally, Table M3 reveals the number of test cases needed to predict an exposure of 150 cGy using the one-point algorithm.

TABLE M3

Number of cases to predict 150 cGy for the One-point algorithm

| # teeth with < 150 cGy | # teeth predicted < 150 cGy |
|------------------------|------------------------------|
| 6 | 6 |
| # teeth with > 150 cGy | # teeth predicted > 150 cGy |
| 11 | 11 |

Specificity (<150 cGy prediction)=6/6=100%

Sensitivity (>150 cGy prediction)=11/11/=100%

IV. Clinical Measurement of Post-Exposure Radiation Doses

The Problem

There are plausible circumstances in which populations potentially have been exposed to doses of ionizing radiation that could cause direct clinical effects within days or weeks, but there is no clear knowledge as to the magnitude of the exposure to individuals. Moreover, it is likely that many of the individuals will not have received clinically significant doses of radiation, while others may have been exposed to potentially life-threatening doses.

The range of clinical symptoms for the various doses and exposures to ionizing radiation are given by Table C1 below.

TABLE C1

| Dose Range (cGy) | Initial Symptoms | Time of Initial Symptoms (Begin/End) |
|---|---|---|
| 0–75 | None to slight incidence of transient headache and nausea. Vomiting in up to 5% of personnel in upper part of dose range. | 6 hours/12 hours |
| 75–125 | Transient mild nausea and vomiting in 5–30% of personnel | 3–5 hours/1 day |
| 125–300 | Transient mild to moderate nausea and vomiting in 20–70% of personnel. Mild to moderate fatigability and weakness in 25–60% of personnel | 2–3 hours/2 days |
| 300–530 | Transient moderate nausea and vomiting in 50–90% of personnel. Mild to moderate fatigability in 60–90% of personnel | 2 hours/3–4 days |
| 530–830 | Moderate to severe nausea, vomiting in 80–100% of personnel. Moderate to extreme fatigability in 90–100% of personnel. | Within the first hour/ days to weeks |

Data excerpted from STANAG No. 2083. Commander's Guide on Nuclear Radiation Exposure of Groups The clinical method obtains retrospective dose on individuals sufficient to rapidly discriminate among:
Exposures that are very unlikely to cause any acute symptoms (<50 cGy);
Exposures that are likely to lead to mild and delayed clinical symptomatology (75–150 cGy);
Exposures that are likely to lead to moderate to severe clinical symptomatology (150–300 cGy);
Exposures that are likely to lead to early severe clinical symptomatology with a potential for lethal outcome (>300 cGy); and
Exposures that are very likely to lead to early death (>600 cGy).

The Characteristics of the Instrument:
Can provide the measurements within 5 minutes;
Will be moderately portable (total weight about 100 kg or 220 lbs.);
Power requirements of 1.0–1.5 kW (peak, during 30 sec. intervals, total duty cycle about 10%);
Electromagnetic radiation is unlikely to perturb the instrument (except at the operating frequency of 1.2 GHz);
One button operation with readout in dose; and
Rugged construction.

Figure 15A:
FIGS. 15A–15C respectively are illustrations of the present invention in an in-vivo clinical use setting.
Figure 15C:
Figure 15B:
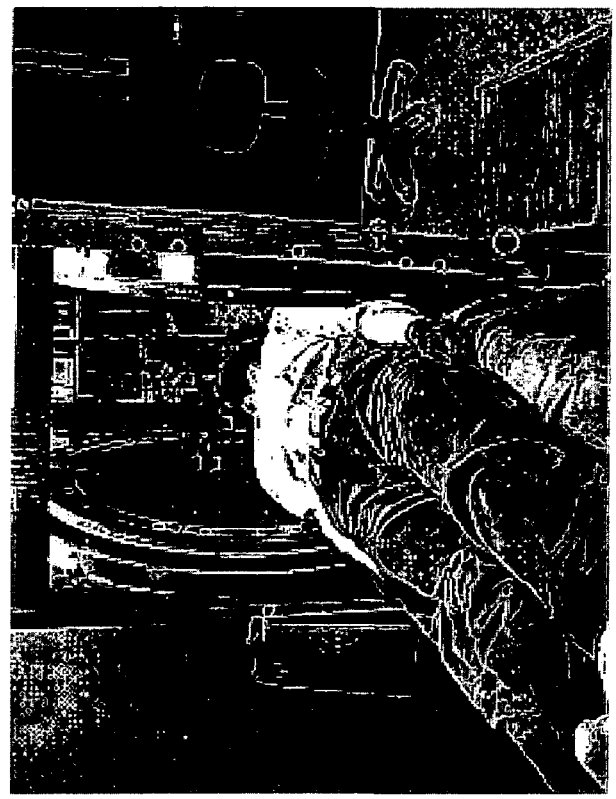
Figure 16A:
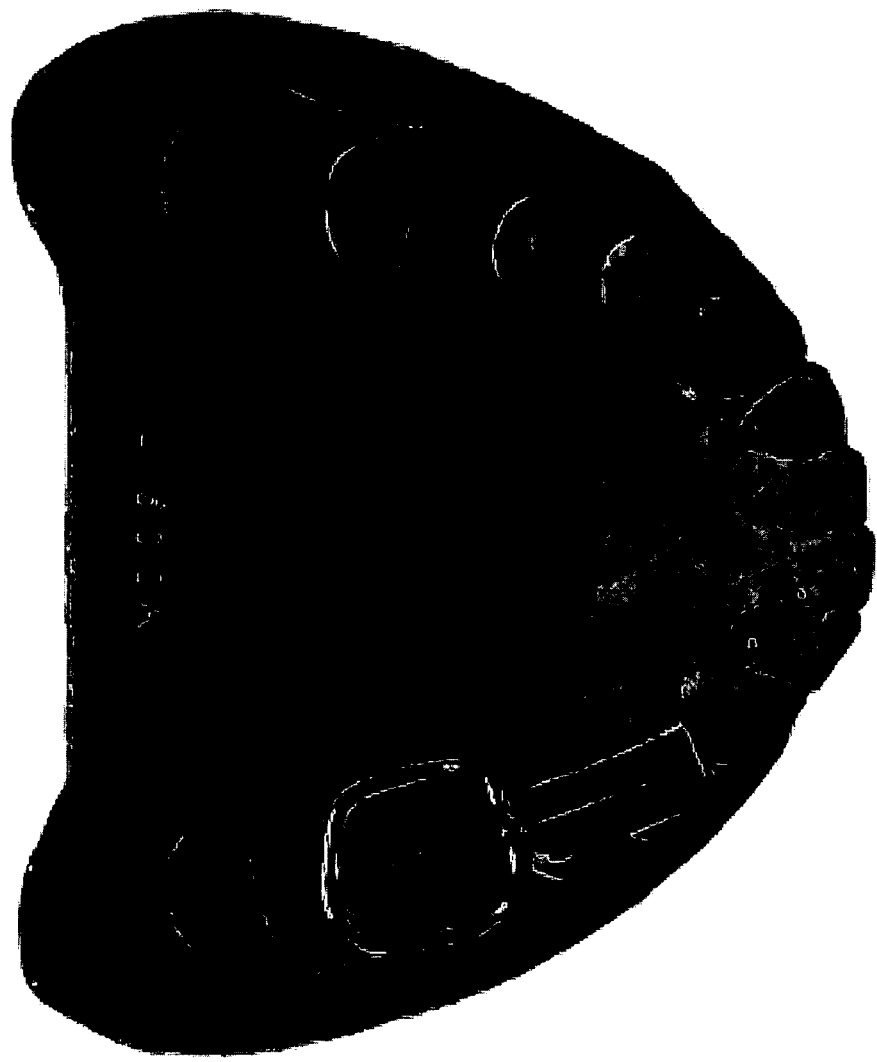
FIGS. 16A–16C respectively are illustrations of resonator coils in loop form for use with molar teeth.
Figure 16B:
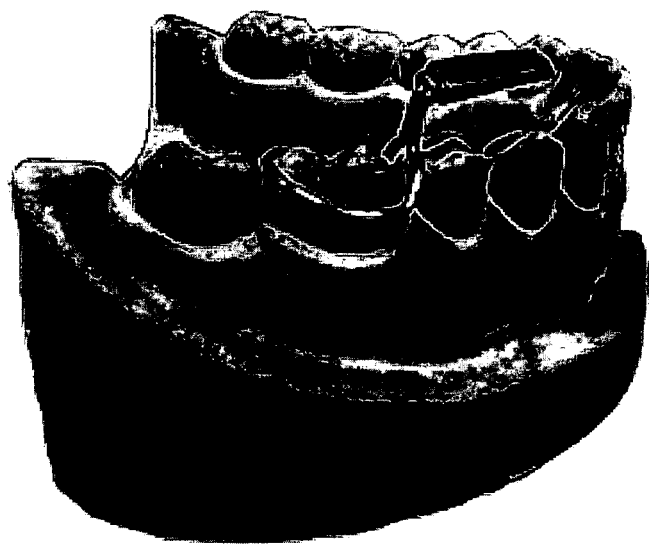
Figure 16C:
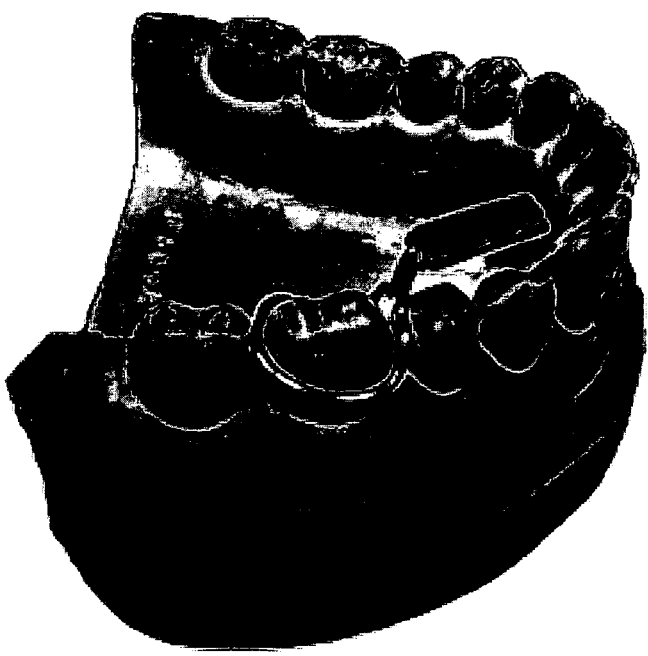
Figure 17A:
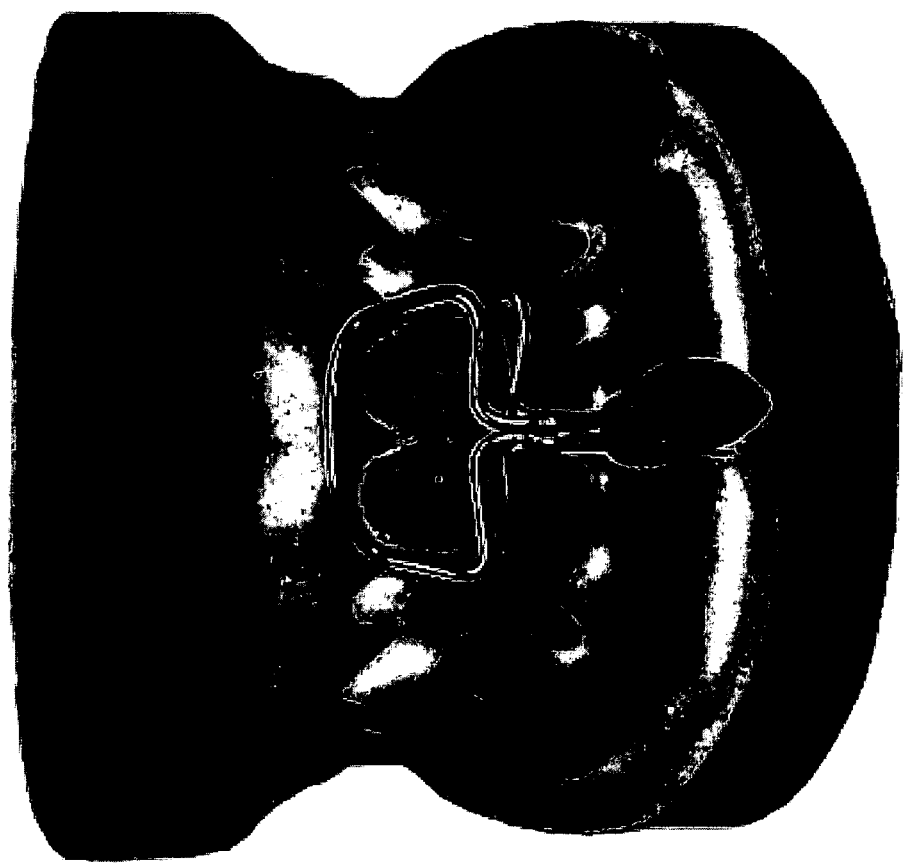
FIGS. 17A–17C respectively are illustrations of resonator coils in loop form for use with incisor teeth.
Figure 17B:
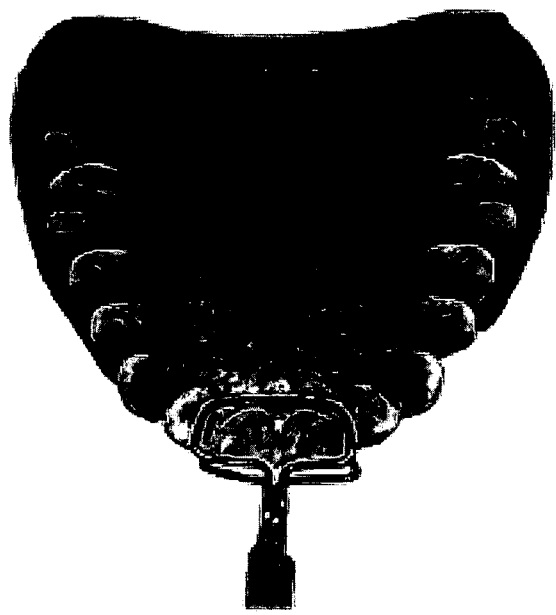
Figure 17C:
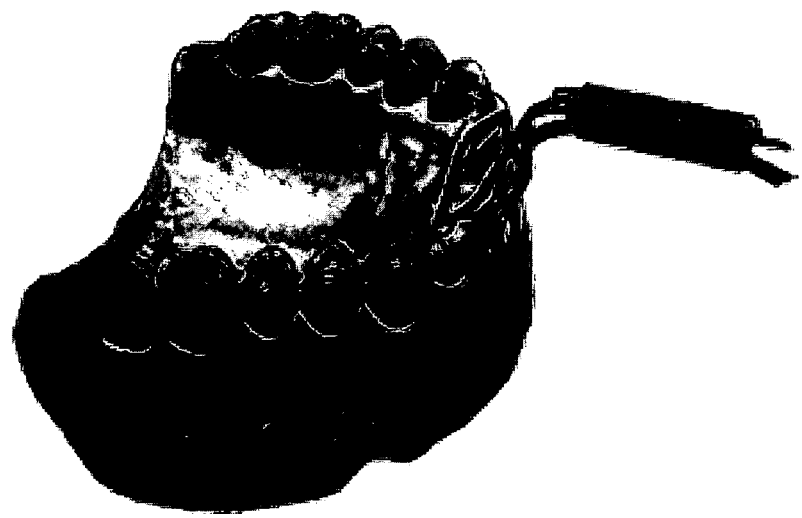

The clinical apparatus and intended setup in the field is shown by FIGS. 15A–15C respectively. The resonator construct as it would be positioned in the human mouth for measurement of molars is shown by FIGS. 16A–16C; and is positioned for measurement of incisors as shown by FIGS. 17A–17C respectively.

Clinical Evaluation 1

Figure 18:
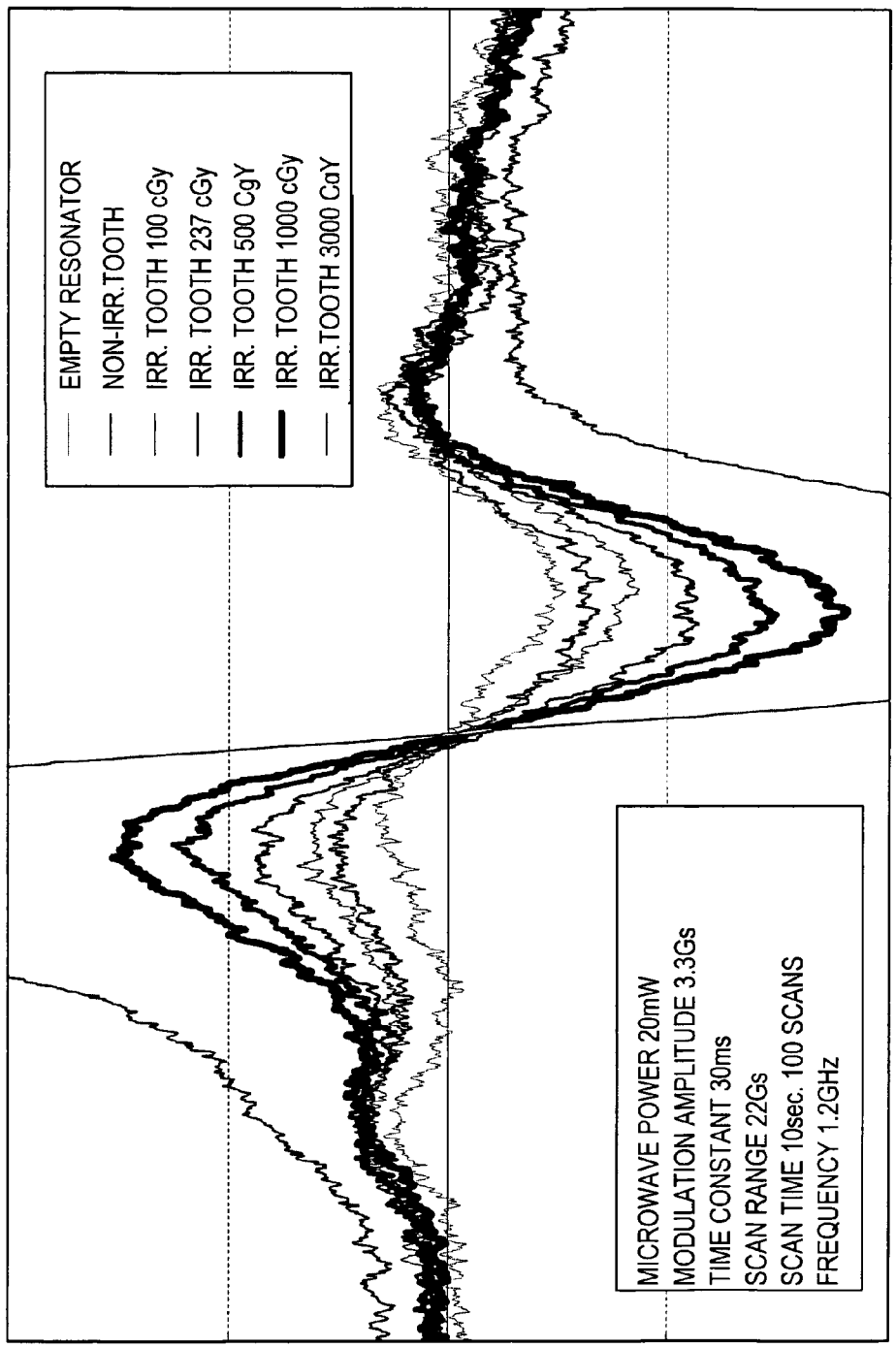
FIG. 18 is a graph showing EPR spectra of human teeth at L-band over varying doses of radiation.
Figure 19:
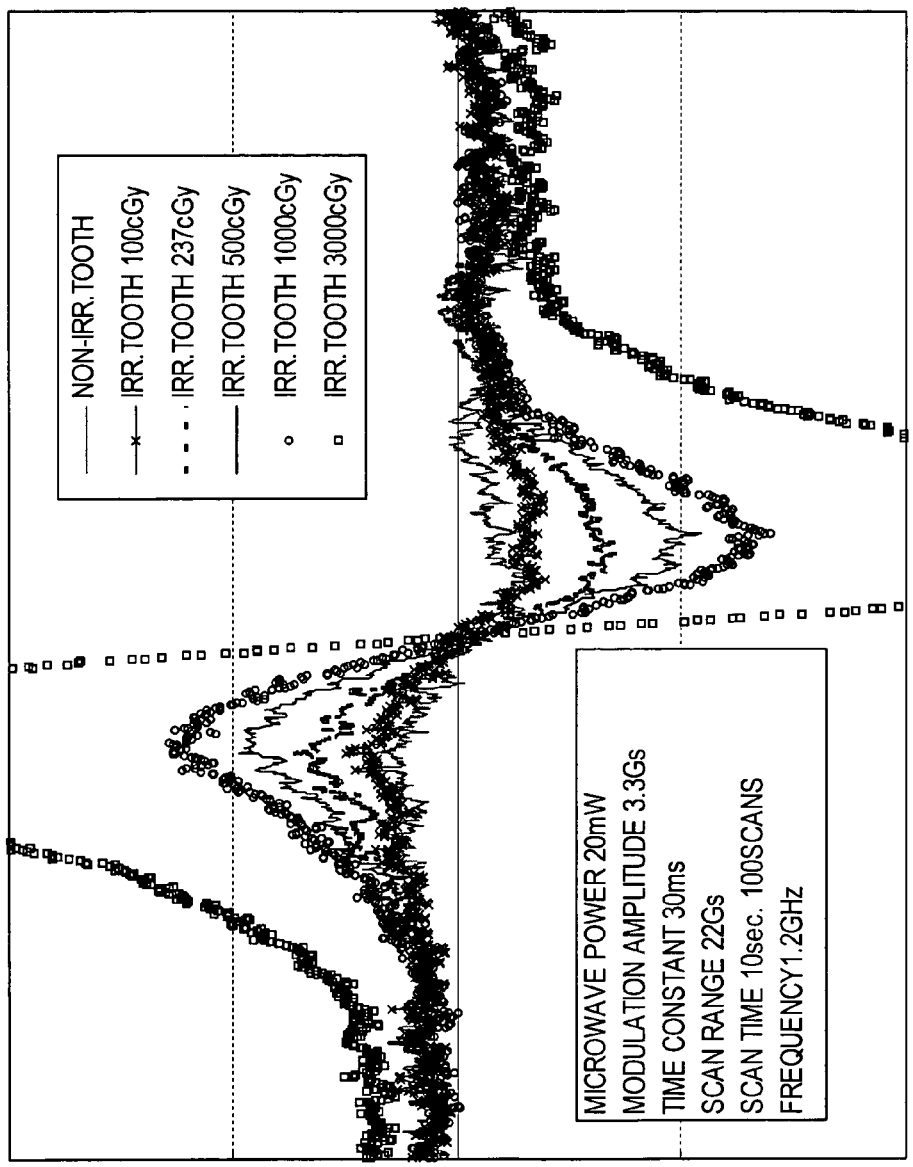
FIG. 19 is a graph showing the EPR spectra of FIG. 18 after subtraction of signal from an empty resonator.
Figure 20:
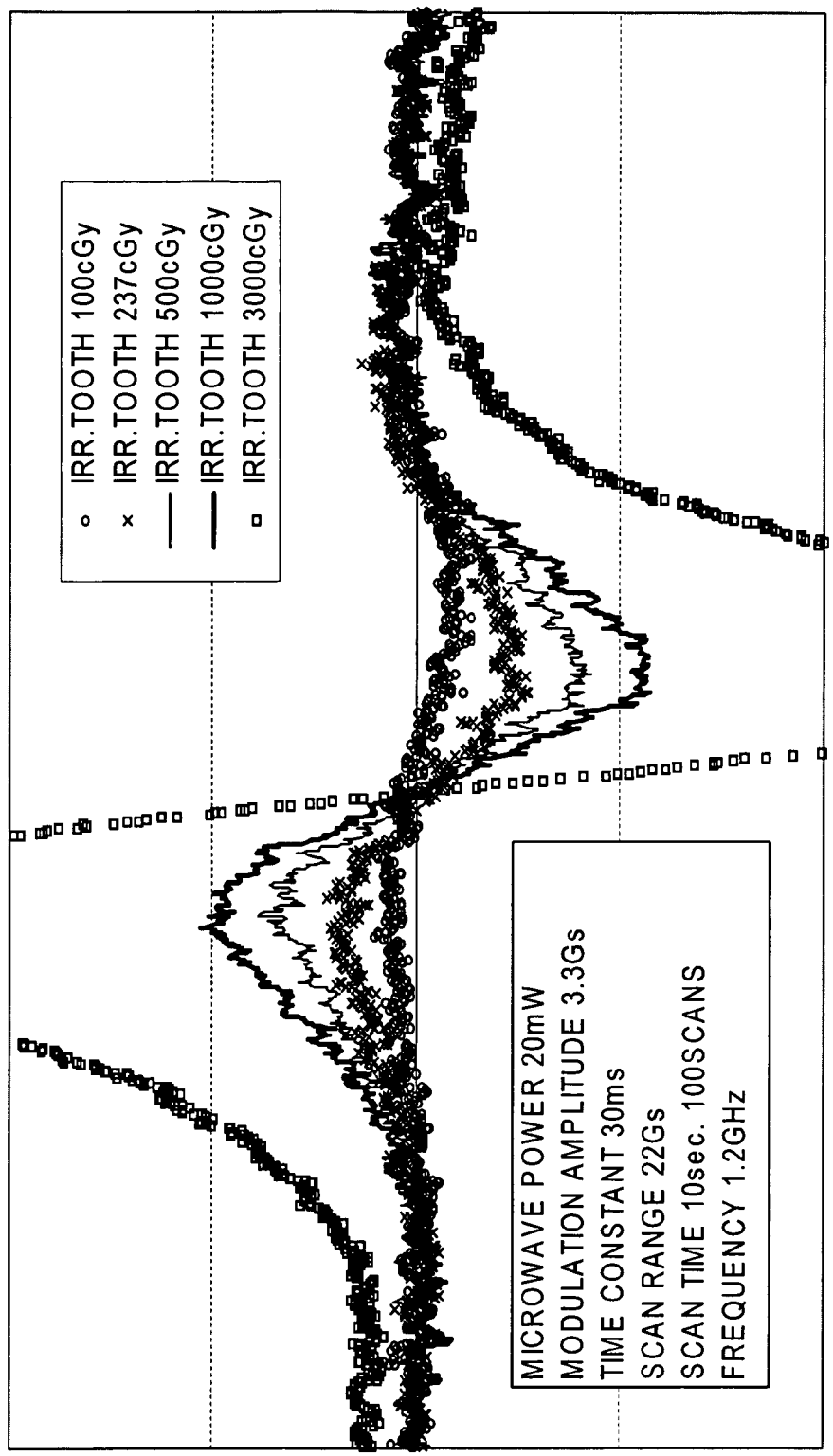
FIG. 20 is a graph showing the EPR spectra of FIG. 18 after subtraction of signal from non-irradiated teeth.
Figure 21A:
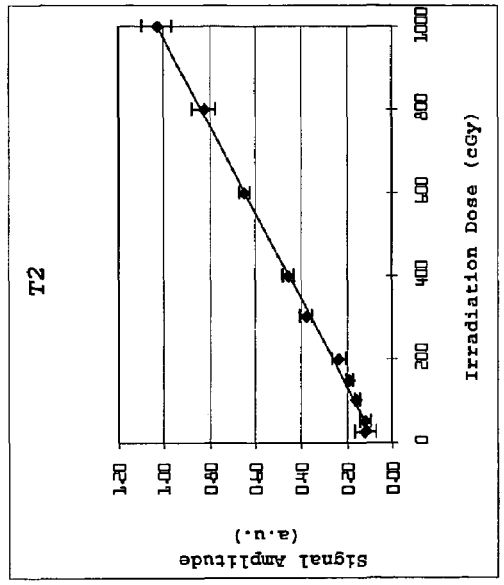
FIGS. 21A–21D respectively are graphs showing a dose response relationship of EPR signal to irradiation dose.
Figure 21B:
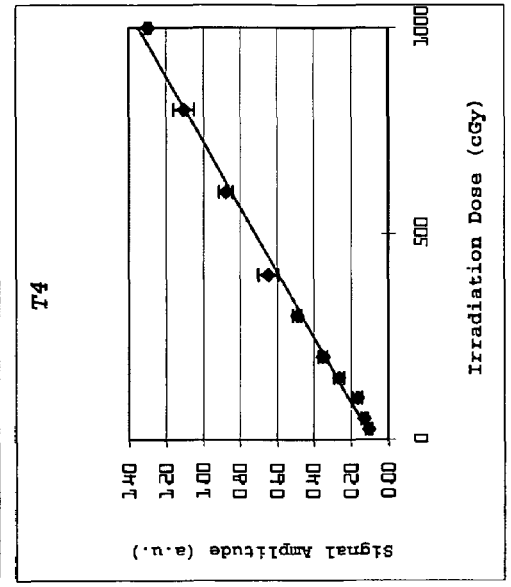
Figure 21C:
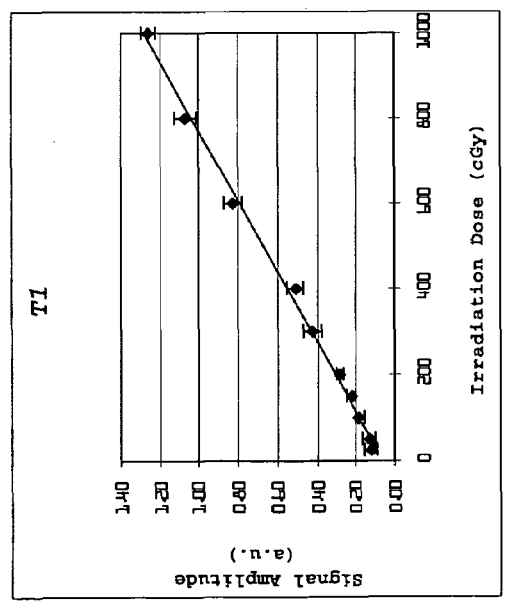
Figure 21D:
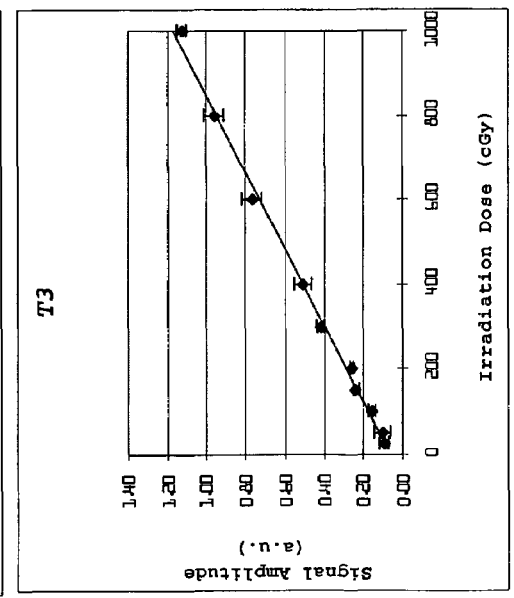

A series of in-vitro evaluations were performed on extracted human teeth which were irradiated with doses ranging from 100–3000 cGy. The resulting EPR spectra of human teeth at L-Band is graphically shown by FIG. 18. For comparison purposes, the EPR spectra obtained after subtraction of background signal from an empty resonator is shown by the graph of FIG. 19. Similarly, the EPR spectra obtained after subtraction of signal from non-irradiated teeth is illustrated by FIG. 20.

Figure 22:
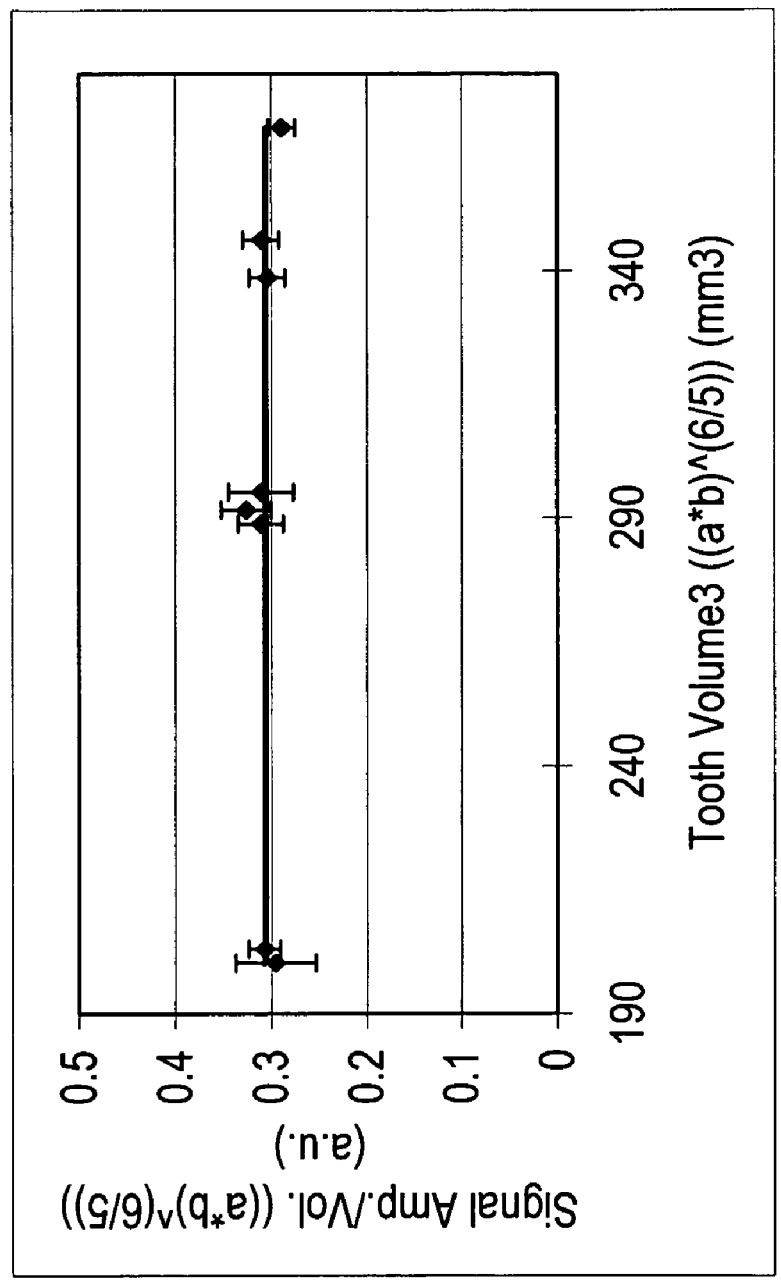
FIG. 22 is a graph showing connections of EPR signal for variations in the volume of human teeth.
Figure 23A:
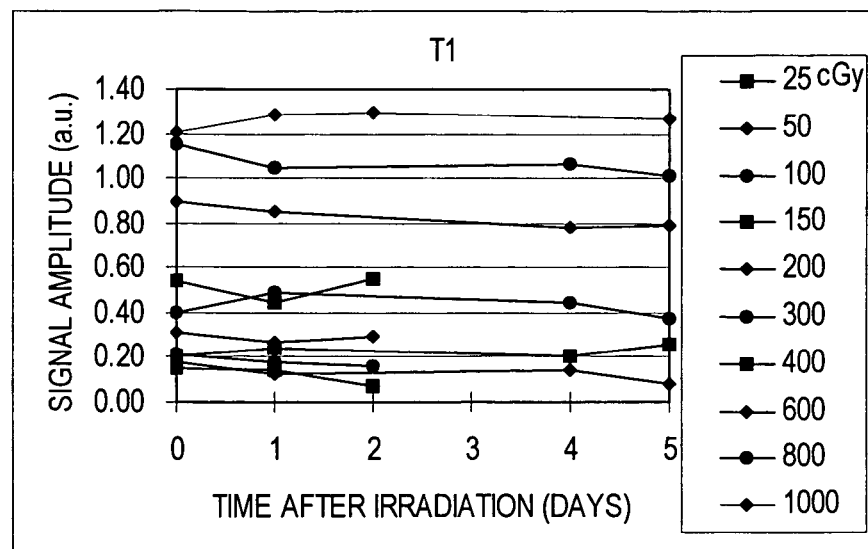
FIGS. 23A–23D respectively are graphs showing the time course of EPR signal after irradiation.
Figure 23B:
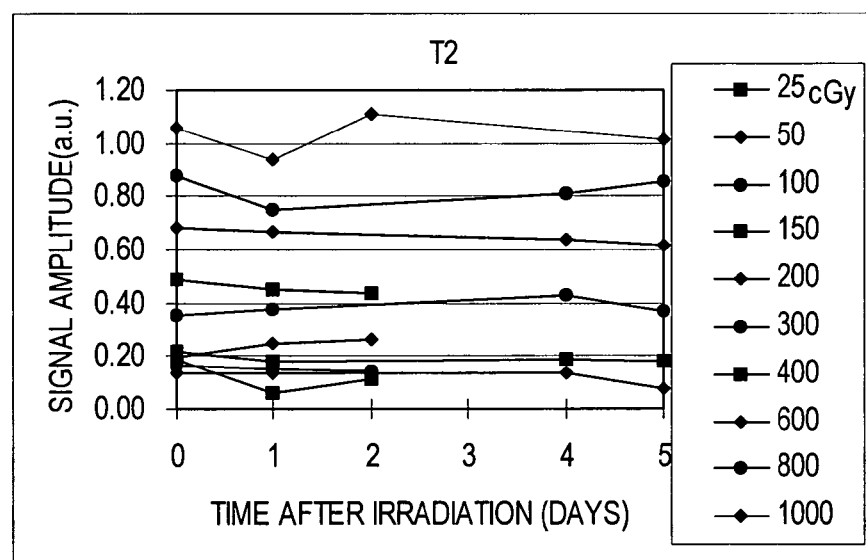
Figure 23C:
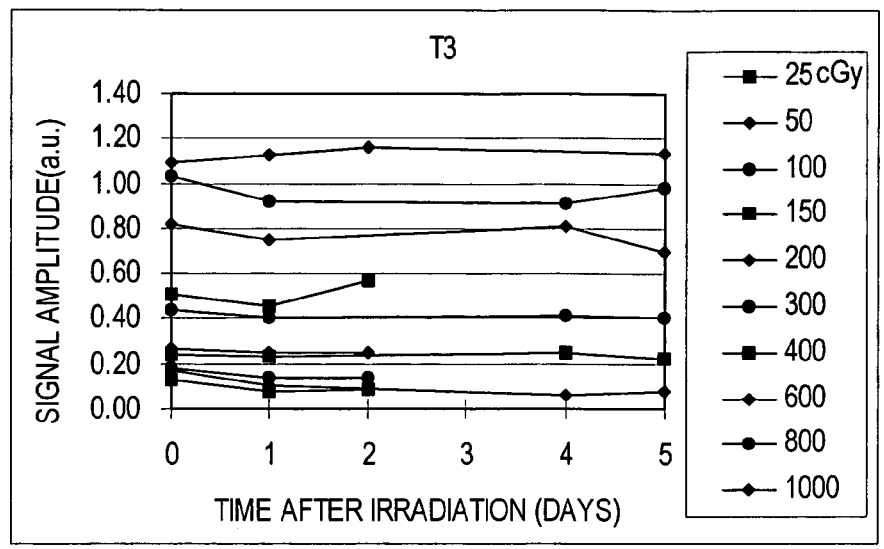
Figure 23D:
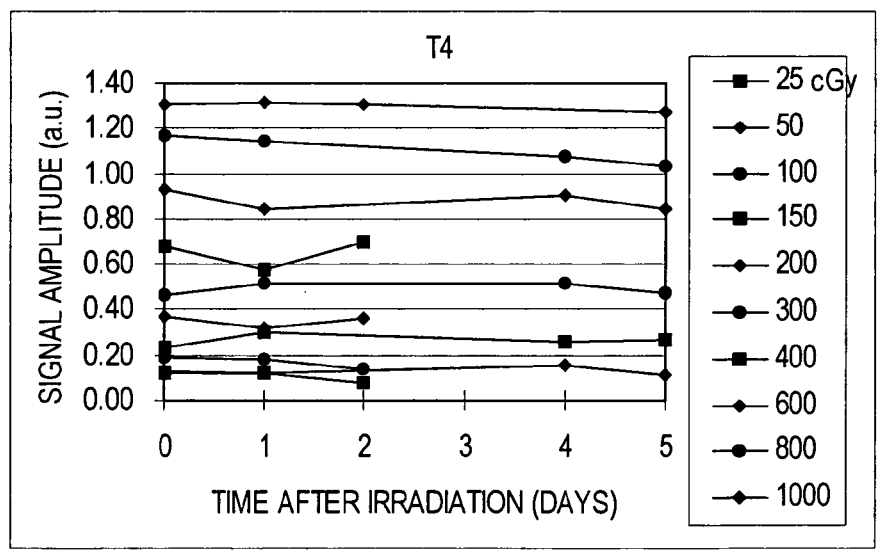
Figure 24A:
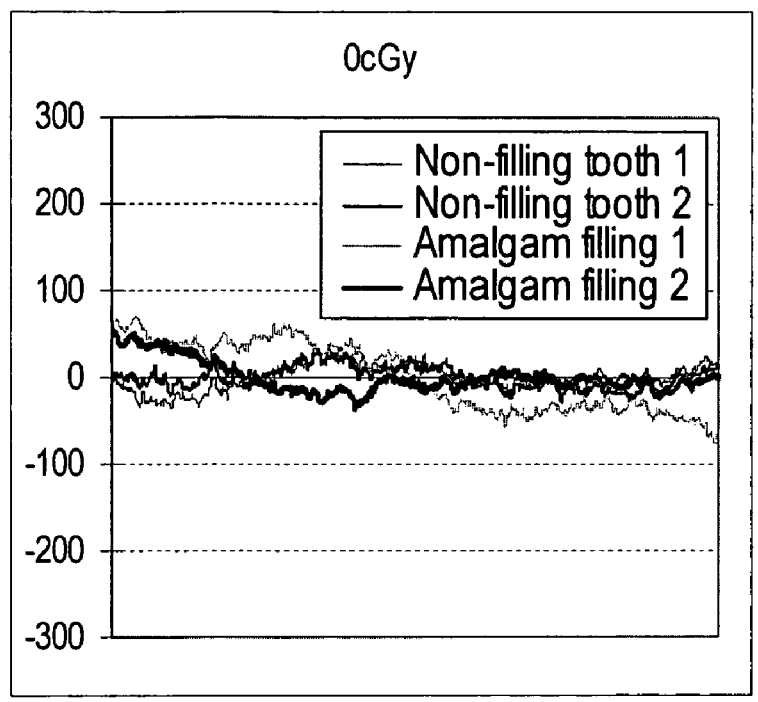
FIGS. 24A–24E respectively are graphs showing the EPR spectra of teeth with amalgam.
Figure 24B:
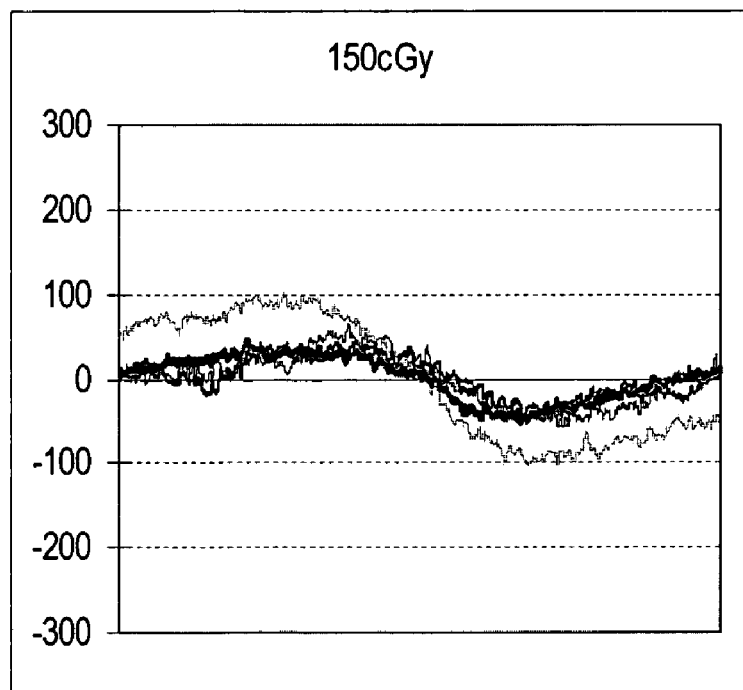
Figure 24C:
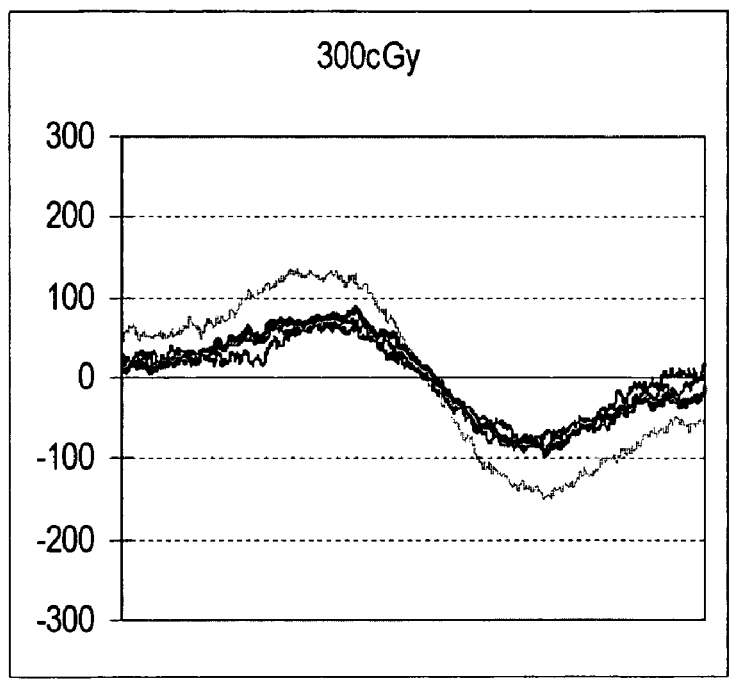
Figure 24D:
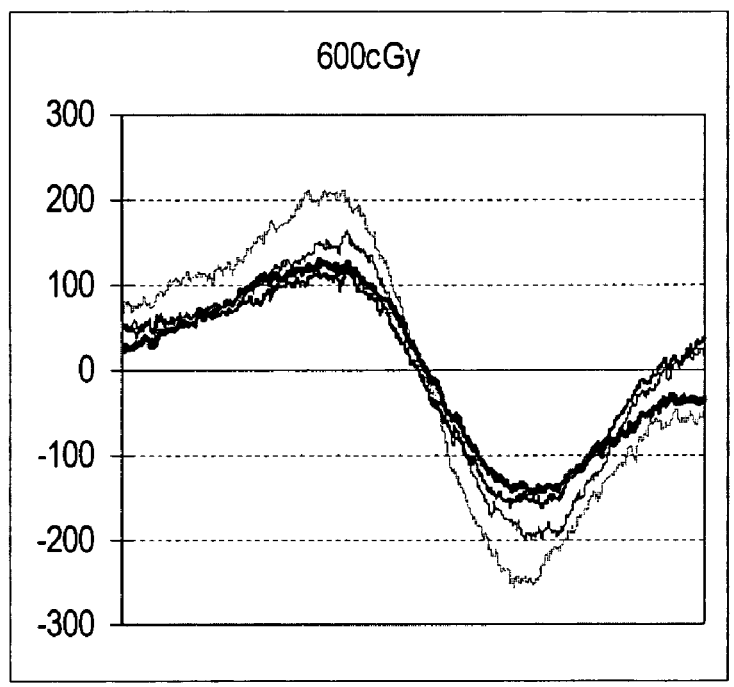
Figure 24E:
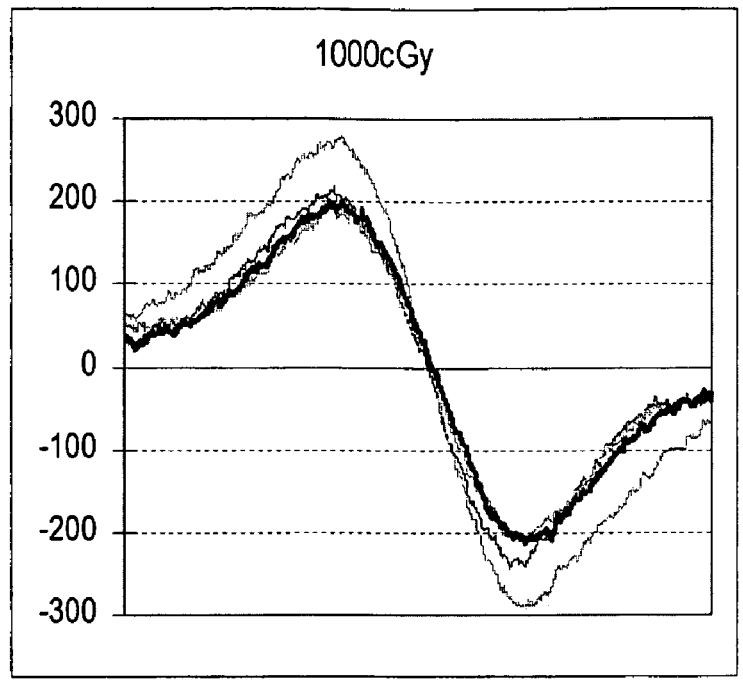

The data empirically obtained in-vitro was then evaluated to show signal amplitude in a close response relationship, as illustrated by the graphs of FIGS. 21A–21D respectively. Again for comparison purposes, the appropriate corrections for variations in the volume of human teeth is presented graphically by FIG. 22; and the time course after irradiation of signal is revealed by the graphs of FIGS. 23A–23D respectively. The EPR spectra of human teeth with amalgam was also empirically evaluated in-vitro and is graphically shown by FIGS. 24A–24E respectively.

Another set of evaluations was performed in-vivo using living human patients. The resulting empirical data obtained in-vivo is presented by FIGS. 25 and 28–31 respectively.

Figure 25:
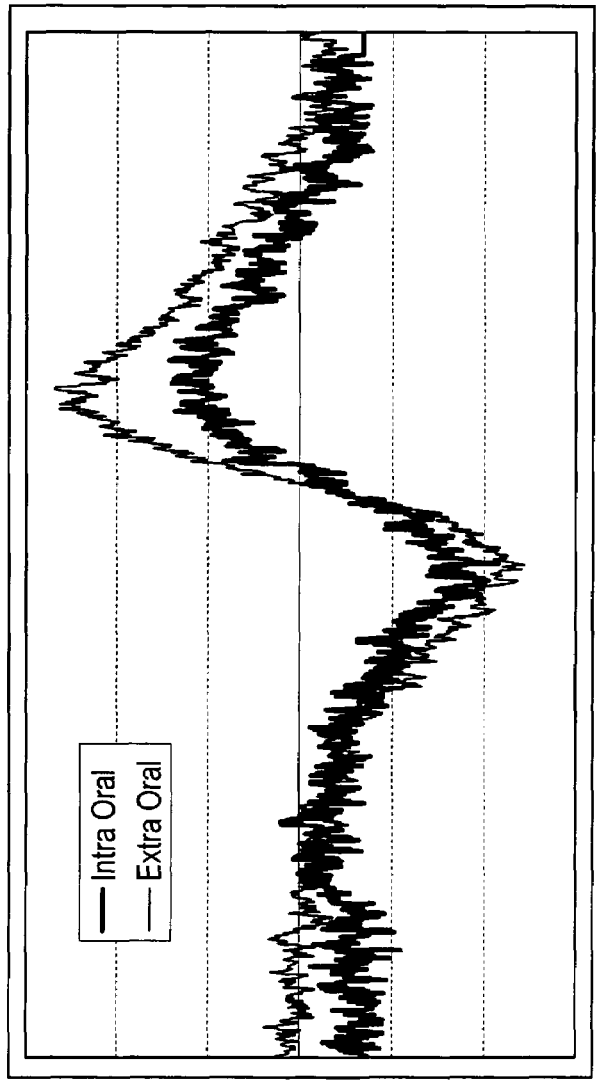
FIG. 25 is a graph and table showing EPR signal sensitivity in the human mouth.
Figure 28B:
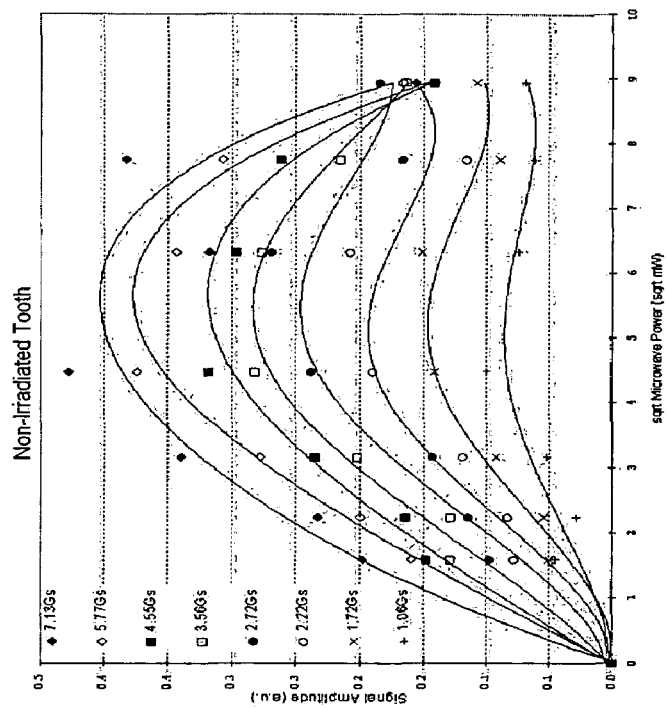
FIGS. 28A and 28B respectively are graphs showing power saturation data for non-irradiated and irradiated teeth.
Figure 28A:
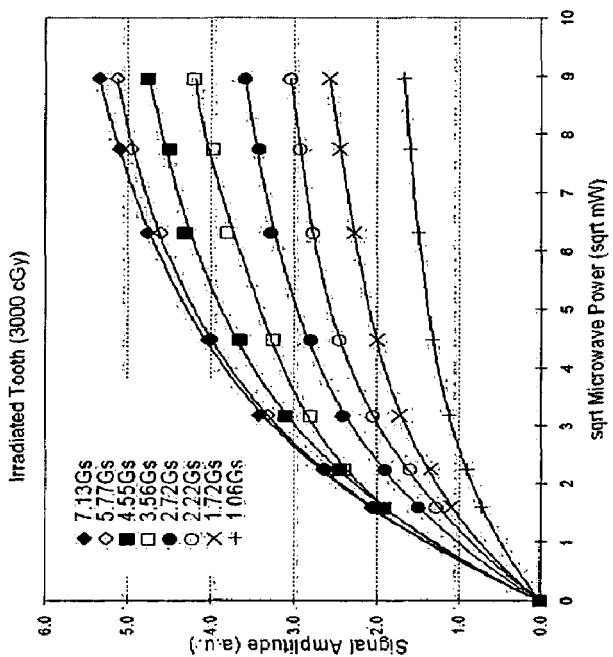
Figure 29A:
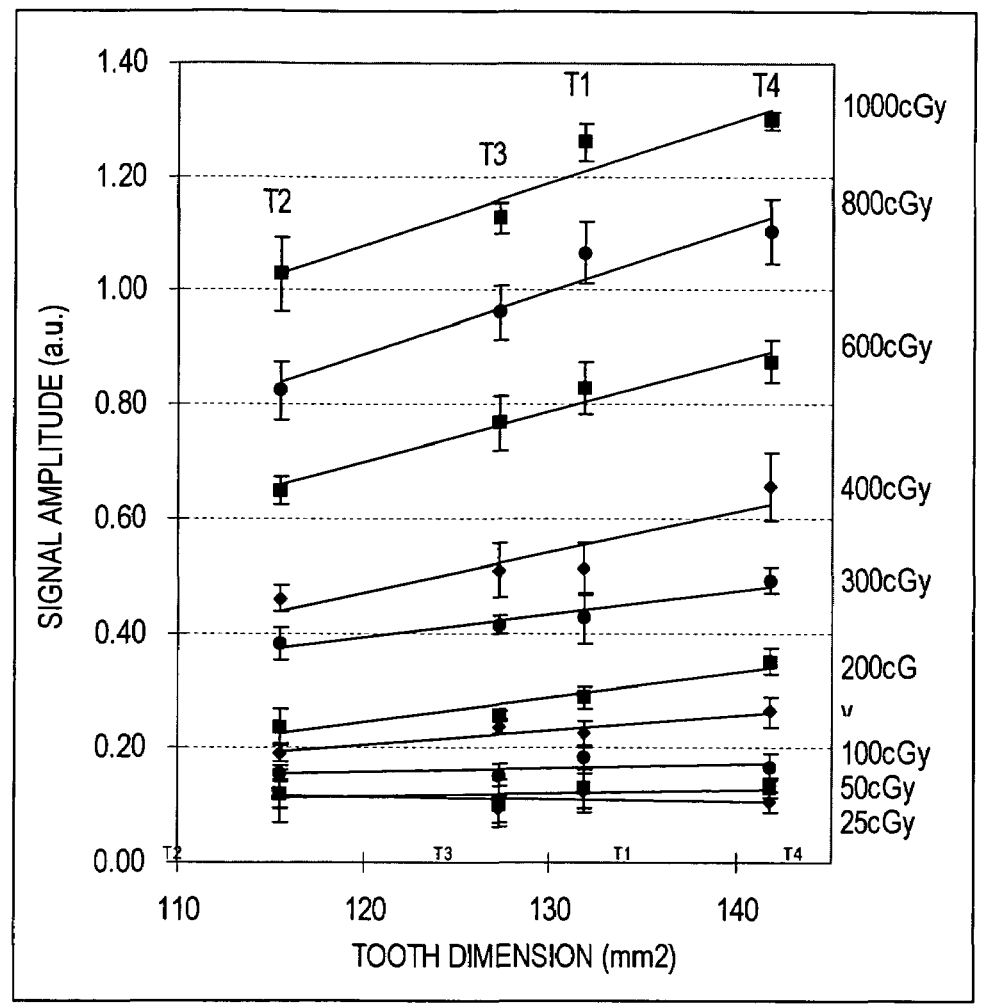
FIGS. 29A–29D respectively are graphs showing the normalization of EPR signal as a function of tooth size.
Figure 29:
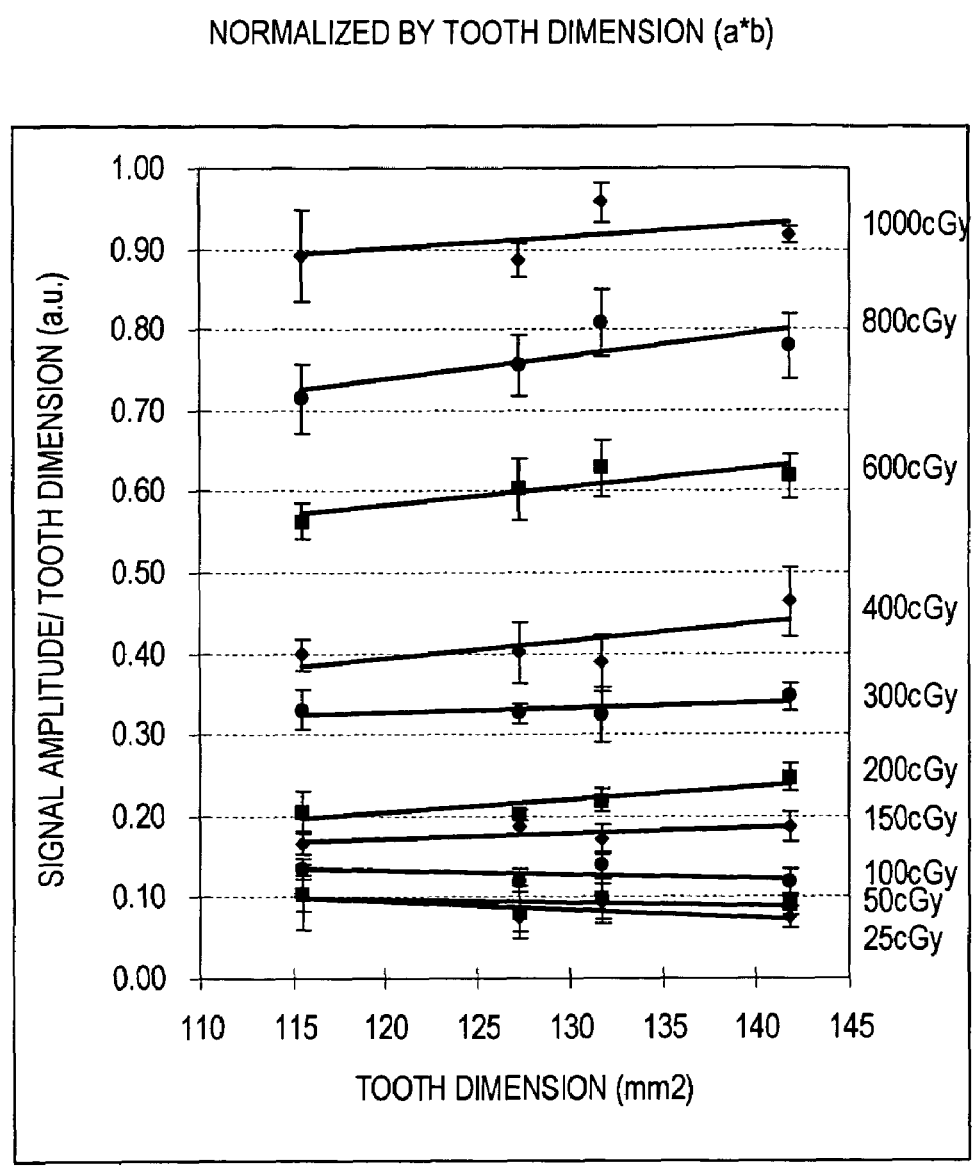
Figure 29C:
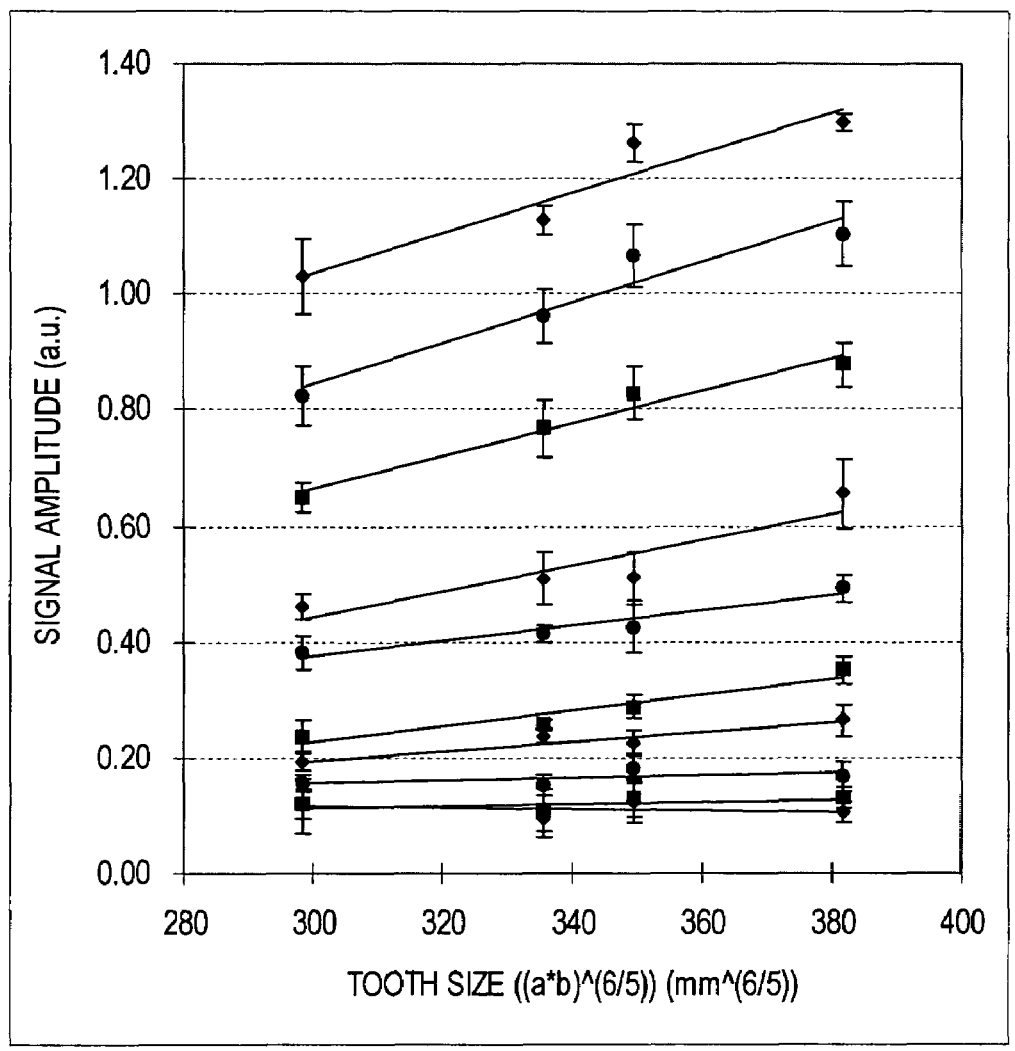
Figure 29D:
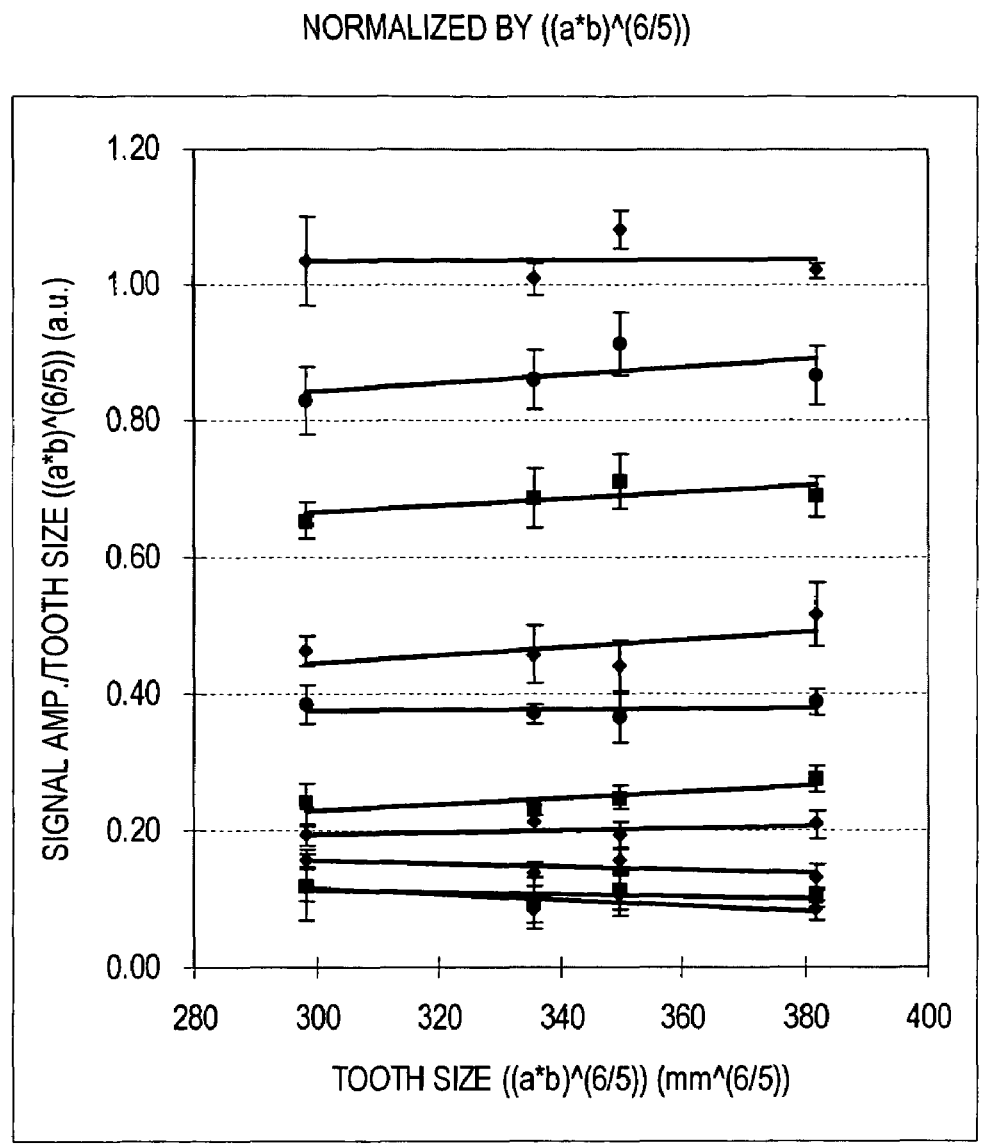
Figure 30A:
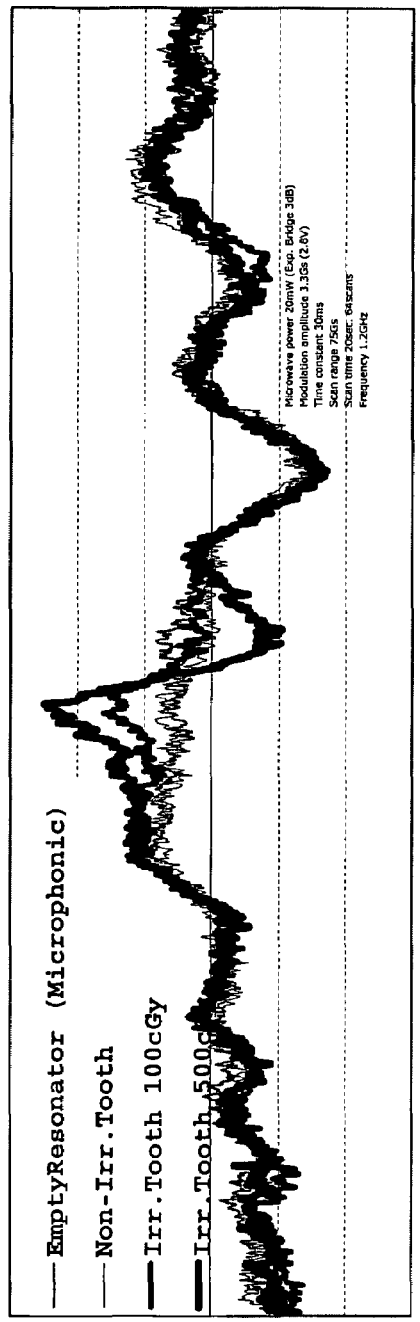
FIGS. 30A and 30B respectively are graphs showing the in-vivo microphonic effects upon EPR spectra of human teeth.
Figure 30B:
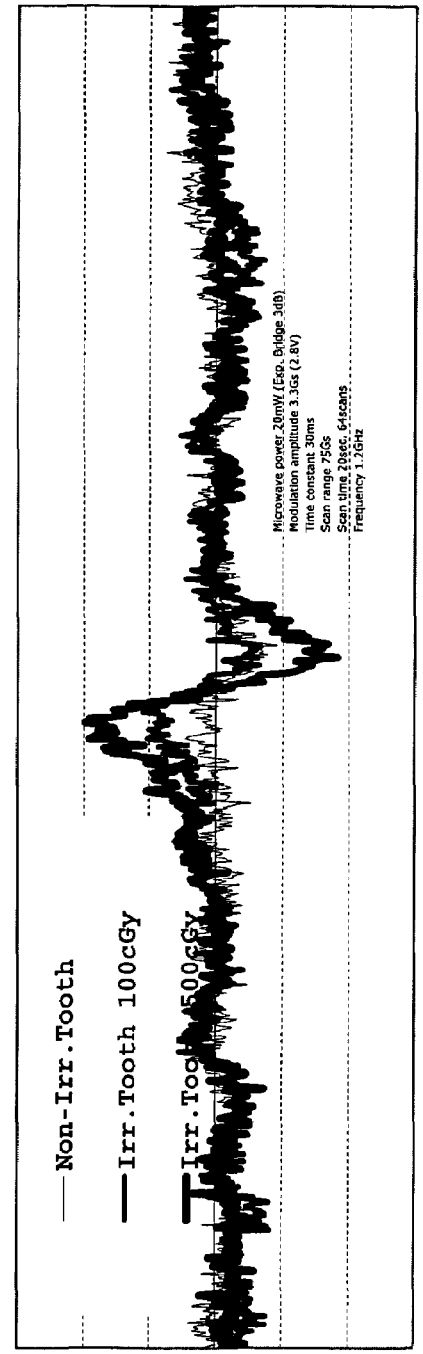
Figure 31A:
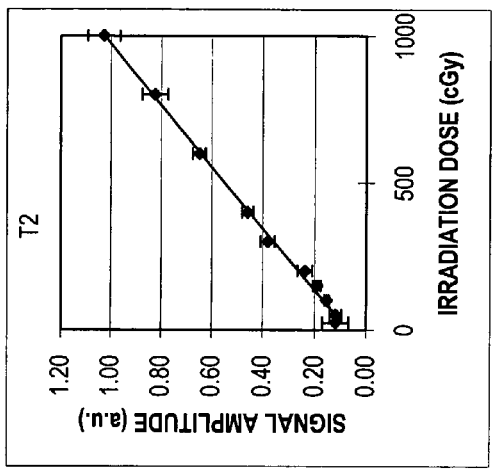
FIGS. 31A–31D respectively are graphs showing the dose response of teeth with amalgam in-vivo.
Figure 31B:
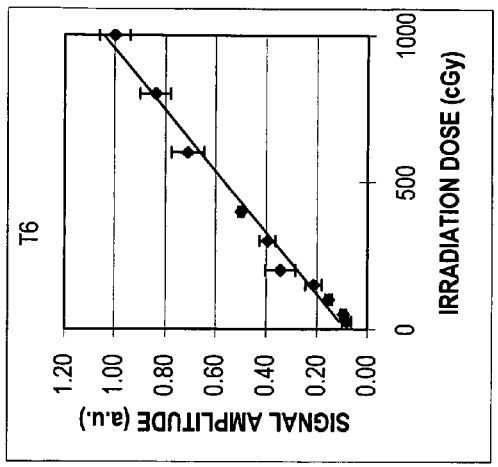
Figure 31C:
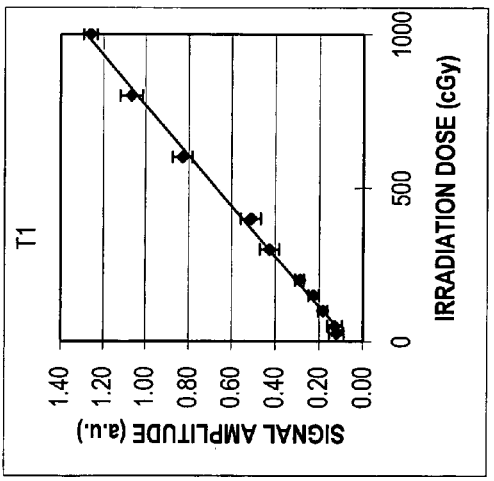
Figure 31D:
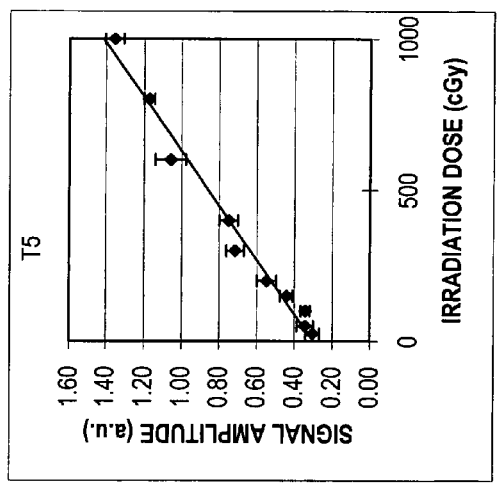

As seen therein, FIG. 25 shows the sensitivity in the human mouth of the methodology, a consideration which is discussed in greater depth below. FIGS. 28A and 28B graphically show the power saturation at various modulations. FIGS. 29A–29D graphically illustrate normalization of empirical values by tooth size. FIGS. 30A and 30B show the microphonic effects of EPR spectra of human teeth. Finally, FIGS. 31A–31D graphically illustrate the dose response patterns of human teeth with amalgam.

Clinical Evaluation 2

The feasibility of making measurements within the human mouth was tested directly, by using the same resonator and the same tooth, in a series of tests. The resonator and tooth were located either extra-orally or within the oral cavity of a living human volunteer. The results are illustrated graphically by FIGS. 25, 26 and 27 respectively.

Figure 26:
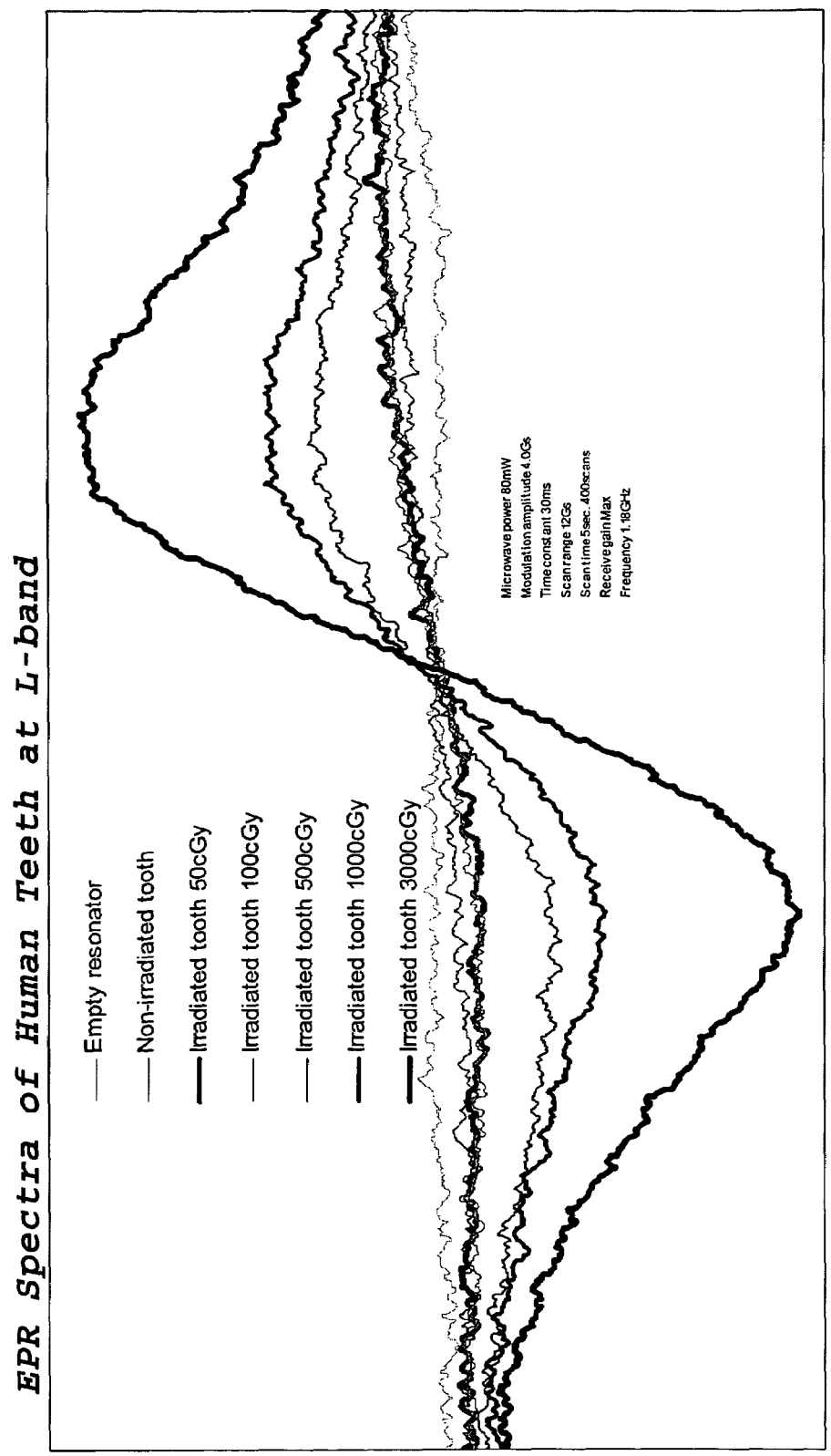
FIG. 26 is a graph showing the in-vivo EPR spectra of human teeth.
Figures 27A, 27B:
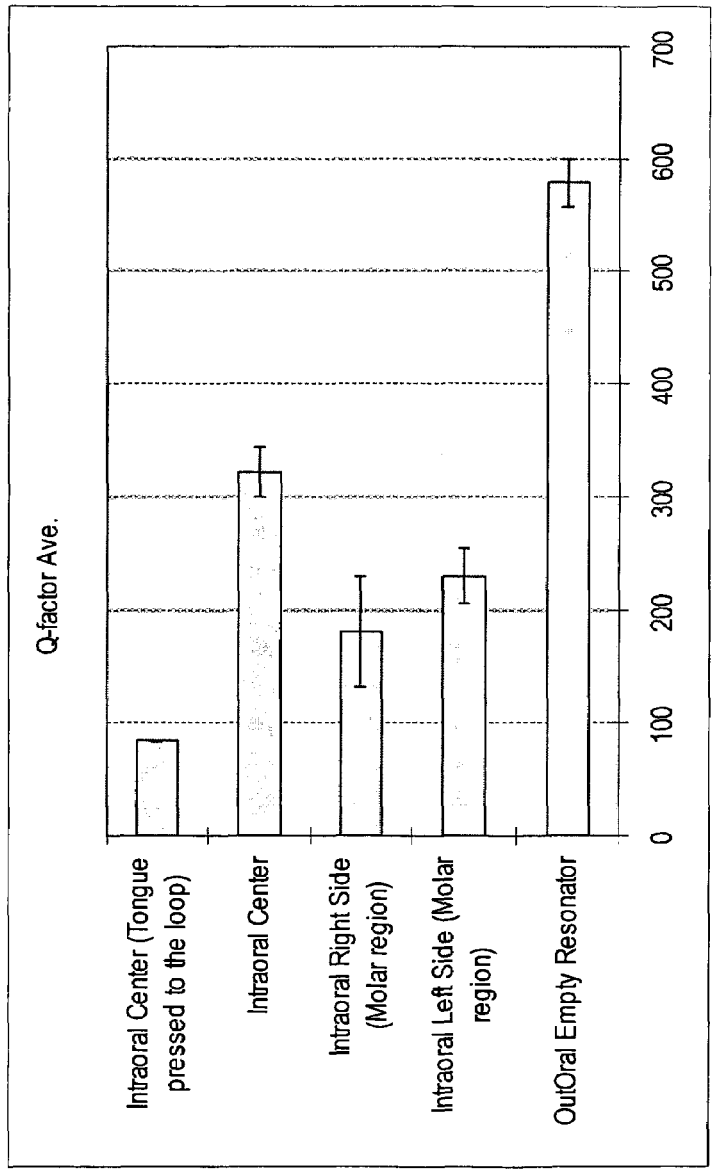
FIG. 27 is a graph and table showing the change of Q-factor in-vivo at different locations of the human mouth.

The data of FIG. 25 show that the EPR spectrum, extra-orally or intra-orally, was essentially identical, with only a modest increase in the background noise of the spectra. FIG. 26 graphically shows the EPR spectra of human teeth at the L-Band; and FIGS. 27A and 27B reveal the change of Q-factor in different regions of the human mouth.

In particular, FIG. 27 as a whole provides data on the effect on the Q factor of positioning at different sites in the mouth. These data, the first EPR measurements ever made within the mouth of a living human subject, confirm fully that the present invention is able to make measurements in the mouth with approximately the same sensitivity as is obtainable under in-vitro conditions. Moreover, because the data of FIG. 27 are from an initial experiment, it is expected that further development of the details comprising the clinical technique will result in an even better sensitivity within the mouth of human subjects.

Conclusions Drawn from and Supported by the Empirical Data

1. The empirical data presented herein clearly show that the methodology of the present invention is capable of meeting its intended goal of being able to detect and measure clinically significant exposures to ionizing radiation. The method provides sufficient accuracy and sensitivity to make fully appropriate clinical decisions in the field as to the necessity of whom to treat and how to treat on an individual basis.

2. The in-vitro empirical data from the experiments with isolated human teeth demonstrate clearly that there are appropriate dose response relationships; that the stability of the radiation induced signals is very good indeed; and that the presence of amalgam fillings will not interfere with the clinical usefulness and applicability of the method.

3. The in-vivo data obtained from the measurements within the human mouth confirm that the properties observed in isolated human teeth are fully applicable to determinations of teeth in-situ within the mouth of a living subject.

4. The method and apparatus of the present invention, therefore, can be used with living patients to determine radiation exposure doses over the entire range of clinical interests—i.e., from less than 100 cGy to more than 2000 cGy.

What we claim is:

1. A dosimetry assessment apparatus for determining the degree of exposure of a living subject to ionizing radiation, wherein said living subject has been previously exposed to an unknown but potentially harmful dose of ionizing radiation, said dosimetry assessment apparatus comprising:
   a detection assembly able to target at least one chosen tooth in the mouth of a living subject and generate a test EPR spectrum from the targeted tooth, said assembly including
   (i) a magnetic field generator of predetermined structure, dimensions and configuration and whose capacities and operating parameters are controlled to generate a stable and substantially uniform magnetic field strength of about 10 to 100 mT with a magnetic filed uniformity of about 0.25% and a selected magnetic modulation field of about +/−0.1 to 0.5 mT with a magnetic field uniformity of about +/−10% over the region of interest,
   (ii) a resonator construct of predetermined dimensions and configuration which is adapted for engagement with at least one chosen tooth in the mouth of the living subject and whose operation allows for the emission of a radiowave of appropriate frequency for EPR measurement which is applied on-demand through the substance of the chosen tooth, and
   (iii) an electron paramagnetic resonance (EPR) spectrometer which is integrated with said magnetic field generator and whose operation generates a test EPR spectrum which can show the presence and absence of a net magnetic moment within said substantially uniform magnetic field occurring in response to a radiowave of appropriate frequency being applied to the chosen tooth in the mouth of the living subject;
   electronic detection equipment able to detect the presence and absence of a net magnetic moment within a test EPR spectrum;
   electronic operating controls coupled to said detection assembly;
   a power supply integrated with said detection assembly; and
   a mathematical model library of predicted EPR spectra for teeth before and after exposure to known doses of ionizing radiation.

2. The dosimetry assessment apparatus as recited in claim 1 further comprising electronic comparison equipment for comparing a test EPR spectrum with said library of EPR spectra.

3. The dosimetry assessment apparatus as recited in claim 2 wherein said comparison of a test EPR spectrum with said library of EPR spectra is viewed as a readable output of ionizing radiation dose exposure.

4. The dosimetry assessment apparatus as recited in claim 1 wherein said magnetic field generator is ergonomically configured.

5. The dosimetry assessment apparatus as recited in claim 1 wherein the direction of said substantially uniform magnetic field is generated perpendicular to a surface of at least one chosen tooth in the mouth of the living subject.

6. The dosimetry assessment apparatus as recited in claim 1 wherein at least a part of said resonance construct is curved in configuration for engagement with a chosen tooth.

7. The dosimetry assessment apparatus as recited in claim 1 wherein at least a part of said resonance construct is oval in configuration for engagement with a chosen tooth.

8. The dosimetry assessment apparatus as recited in claim 1 wherein said magnetic field generator is composed of at least one naturally occurring and intrinsically magnetic material.

9. The dosimetry assessment apparatus as recited in claim 1 wherein said magnetic field generator is a manufactured electromagnetic structure.

10. The dosimetry assessment apparatus as recited in claim 1 wherein said apparatus is transportable on-demand.

11. The dosimetry assessment apparatus as recited in claim 10 wherein said transpotable apparatus weighs less than 100 kilograms.

12. The dosimetry assessment apparatus as recited in claim 1 wherein said resonance construct can emit and apply a radiowave at a frequency ranging from about 0.3–3.0 GHz.

13. A comparative dosimetry assessment method for determining the degree of exposure of a living subject to ionizing radiation, said comparative dosimetry assessment method comprising the steps of:
   identifying at least one living subject who is suspected of having been previously exposed to an unknown but potentially harmful dose of ionizing radiation;
   obtaining a dosimetry apparatus for measuring exposure to ionizing radiation in a living subject, said apparatus being suitable for the targeting of at least one chosen tooth in the mouth of a living subject and comprising
   (i) a magnetic field generator of predetermined structure, dimensions and configuration and whose capacities and operating parameters are controlled to generate a stable and substantially uniform magnetic field strength of about 10 to 100 mT with a magnetic field uniformity of about 0.25% and a selected magnetic modulation field of about +/−0.1 to 0.5 mT with a magnetic field uniformity of about +/−10% over the region of interest,
   (ii) a resonator construct of predetermined dimensions and configuration which is adapted for engagement with at least one chosen tooth in the mouth of the living subject, whose operation allows for the emission of a radiowave of appropriate frequency for EPR measurement which is applied on-demand through the substance of the chosen tooth,
   (iii) an electron paramagnetic resonance (EPR) spectrometer which is integrated with said magnetic field generator and whose operation generates a test EPR spectrum which can show the presence and absence of a net magnetic moment within said substantially uniform magnetic field occurring in response to a radiowave of appropriate frequency being applied to the chosen tooth in the mouth of the living subject, (iv) electronic operating controls, (v) an integrated power supply, (vi) a mathematical model library comprising predicted EPR spectra of teeth before and after exposure to known doses of ionizing radiation, and (vii) comparison equipment for comparing a test EPR spectrum with said mathematical model library of predicted EPR spectra;

targeting said dosimetry apparatus to at least one chosen tooth within the mouth of a living subject;

operating said dosimetry apparatus to obtain a test EPR spectrum from the targeted tooth within the mouth of a living subject; and comparing said test EPR spectrum with said mathematical model library of predicted EPR spectra to detect the presence or absence of a net magnetic moment within said test EPR spectrum, wherein said comparison of EPR spectra provides a measure of the subject's previous exposure to ionizing radiation.

14. The dosimetry assessment method as recited in claim 13 wherein said comparison of a test EPR spectrum with said library of EPR spectra results in a readable output of the exposure to known doses of ionizing radiation.

15. The dosimetry assessment method as recited in claim 13 wherein said magnetic field generator is ergonomically configured.

16. The dosimetry assessment method as recited in claim 13 wherein the direction of said substantially uniform magnetic field is generated perpendicular to a surface of at least one chosen tooth in the mouth of the living subject.

17. The dosimetry assessment method as recited in claim 13 wherein at least a part of said resonance construct is curved in configuration for engagement with a chosen tooth.

18. The dosimetry assessment method as recited in claim 13 wherein at least a part of said resonance construct is oval in configuration for engagement with a chosen tooth.

19. The dosimetry assessment method as recited in claim 13 wherein said magnetic field generator is composed of at least one naturally occurring and intrinsically magnetic material.

20. The dosimetry assessment method as recited in claim 13 wherein said magnetic field generator is a manufactured electromagnetic structure.

21. The dosimetry assessment method as recited in claim 13 wherein said apparatus is transportable on-demand.

22. The dosimetry assessment method as recited in claim 13 wherein said resonance construct can emit and apply a radiowave at a frequency ranging from about 0.3–3.0 GHz.

* * * * *